US010844390B2

(12) United States Patent
Saidi et al.

(10) Patent No.: US 10,844,390 B2
(45) Date of Patent: Nov. 24, 2020

(54) ROOT-PREFERENTIAL AND STRESS INDUCIBLE PROMOTER AND USES THEREOF

(71) Applicant: BASF AGRICULTURAL SOLUTIONS SEED, US LLC, Research Triangle Park, NC (US)

(72) Inventors: Younousse Saidi, De Pinte (BE); Bart Den Boer, Merelbeke (BE); Celine Mouchel, De Pinte (BE); Stephane Pien, Bergisch Gladbach (DE)

(73) Assignee: BASF AGRICULTURAL SOLUTIONS SEED, US LLC, Research Triangle Park, NC (US)

( * ) Notice: Subject to any disclaimer, the term of this patent is extended or adjusted under 35 U.S.C. 154(b) by 147 days.

(21) Appl. No.: 15/750,695

(22) PCT Filed: Jul. 19, 2016

(86) PCT No.: PCT/EP2016/067152

§ 371 (c)(1),
(2) Date: Feb. 6, 2018

(87) PCT Pub. No.: WO2017/025282

PCT Pub. Date: Feb. 16, 2017

(65) Prior Publication Data

US 2020/0056197 A1 Feb. 20, 2020

(30) Foreign Application Priority Data

Aug. 7, 2015 (EP) .................................... 15180269
Sep. 14, 2015 (EP) .................................... 15185056
Sep. 14, 2015 (EP) .................................... 15185057

(51) Int. Cl.
*C12N 15/82* (2006.01)

(52) U.S. Cl.
CPC ..... *C12N 15/8227* (2013.01); *C12N 15/8271* (2013.01)

(58) Field of Classification Search
None
See application file for complete search history.

(56) References Cited

U.S. PATENT DOCUMENTS

| | | | |
|---|---|---|---|
| 4,757,011 A | 7/1988 | Chaleff et al. | |
| 4,769,061 A | 9/1988 | Comai | |
| 4,940,835 A | 7/1990 | Shah et al. | |
| 4,971,908 A | 11/1990 | Kishore et al. | |
| 5,004,863 A | 4/1991 | Umbeck | |
| 5,159,135 A | 10/1992 | Umbeck | |
| 5,459,252 A | 10/1995 | Conkling et al. | |
| 5,466,785 A | 11/1995 | De Framond | |
| 5,491,288 A | 2/1996 | Chaubet et al. | |
| 5,510,471 A | 4/1996 | Lebrun et al. | |
| 5,593,874 A | 1/1997 | Brown et al. | |
| 5,633,363 A | 5/1997 | Colbert et al. | |
| 5,633,448 A | 5/1997 | Lebrun et al. | |
| 5,641,876 A | 6/1997 | McElroy et al. | |
| 5,659,122 A | 8/1997 | Austin | |
| 5,750,386 A | 5/1998 | Conkling et al. | |
| 5,792,930 A | 8/1998 | Chaubet et al. | |
| 5,837,848 A | 11/1998 | Ely et al. | |
| 6,018,099 A | 1/2000 | De Framond | |
| 6,084,153 A | 7/2000 | Good et al. | |
| 6,294,712 B1 | 9/2001 | Kleine et al. | |
| 6,423,885 B1 | 7/2002 | Waterhouse et al. | |
| 6,483,013 B1 | 11/2002 | Reynaerts et al. | |
| 7,390,937 B2 * | 6/2008 | Good | C07K 14/415 800/298 |
| 7,982,093 B2 | 7/2011 | Good et al. | |
| 2005/0044585 A1 | 2/2005 | Good et al. | |
| 2005/0089872 A1 | 4/2005 | Kim et al. | |
| 2005/0144667 A1 | 6/2005 | Stanley et al. | |
| 2010/0170011 A1 | 7/2010 | Lee et al. | |

FOREIGN PATENT DOCUMENTS

| | | | |
|---|---|---|---|
| CN | 102229662 A | 11/2011 | |
| EP | 0242236 A1 | 10/1987 | |
| EP | 0242246 A1 | 10/1987 | |
| EP | 0507698 A1 | 10/1992 | |
| EP | 0508909 A1 | 10/1992 | |
| EP | 1339859 A2 | 9/2003 | |
| WO | WO 92/15675 A1 | 9/1992 | |
| WO | WO 93/18170 A1 | 9/1993 | |
| WO | WO 95/20669 A2 | 8/1995 | |
| WO | WO 96/06932 A1 | 3/1996 | |
| WO | WO 96/30517 A1 | 10/1996 | |
| WO | WO 98/12335 A1 | 3/1998 | |
| WO | WO 99/53050 A1 | 10/1999 | |
| WO | WO 99/60141 A1 | 11/1999 | |

(Continued)

OTHER PUBLICATIONS

An et al., "Strong, constitutive expression of the *Arabidopsis* ACT2/ACT8 actin subclass in vegetative tissues," 1996; Plant J. 10(1): pp. 107-121.
Barta et al., "DoOP: Databases of Orthologous Promoters, collections of clusters of orthologous upstream sequences from chordates and plants," 2005; Nucleic Acids Research, vol. 33, pp. D86-D90.
Barton et al., "Amino acid sequence analysis of the annexin super-gene family of proteins," 1991, Eur. J. Biochem. 198: pp. 749-760.
Buchholz et al., "Cyclophilins are encoded by a small gene family in rice," 1994; Plant. Mol. Biol. 25(5): pp. 837-843.

(Continued)

*Primary Examiner* — Matthew R Keogh
(74) *Attorney, Agent, or Firm* — Arent Fox LLP

(57) ABSTRACT

The present invention relates to the field of agriculture. In particular, the invention provides a promoter, a recombinant gene, plants comprising the recombinant genes and a method to improve yield of a cotton plant under stress conditions.

23 Claims, 5 Drawing Sheets

Specification includes a Sequence Listing.

(56) References Cited

FOREIGN PATENT DOCUMENTS

| | | | |
|---|---|---|---|
| WO | WO 00/71733 | A1 | 11/2000 |
| WO | WO 2001/012824 | A1 | 2/2001 |
| WO | WO 2001/051627 | A2 | 7/2001 |
| WO | WO 2001/55433 | A2 | 8/2001 |
| WO | WO 2003/033651 | A2 | 4/2003 |
| WO | WO 2003/076619 | A1 | 9/2003 |
| WO | WO 2004/073390 | A1 | 9/2004 |
| WO | WO 2005/047505 | A2 | 5/2005 |
| WO | WO 2005/049842 | A2 | 6/2005 |
| WO | WO 2005/052170 | A2 | 6/2005 |
| WO | WO 2006/074400 | A2 | 7/2006 |
| WO | WO 2006/085966 | A2 | 8/2006 |
| WO | WO 2007/080127 | A2 | 7/2007 |
| WO | WO 2007/147029 | A2 | 12/2007 |
| WO | WO 2008/095886 | A1 | 8/2008 |
| WO | WO 2008/095887 | A1 | 8/2008 |
| WO | WO 2008/095888 | A1 | 8/2008 |
| WO | WO 2008/095889 | A1 | 8/2008 |
| WO | WO 2008/095910 | A1 | 8/2008 |
| WO | WO 2008/095911 | A2 | 8/2008 |
| WO | WO 2008/095916 | A1 | 8/2008 |
| WO | WO 2008/095919 | A1 | 8/2008 |
| WO | WO 2008/095969 | A1 | 8/2008 |
| WO | WO 2008/095970 | A1 | 8/2008 |
| WO | WO 2008/095972 | A1 | 8/2008 |
| WO | WO 2008/110522 | A1 | 9/2008 |
| WO | WO 2008/139334 | A2 | 11/2008 |
| WO | WO 2008/152008 | A2 | 12/2008 |
| WO | WO 2010/077858 | A1 | 7/2010 |
| WO | WO 2010/091230 | A1 | 8/2010 |
| WO | WO 2010/102172 | A1 | 9/2010 |
| WO | WO 2010/106163 | A1 | 9/2010 |
| WO | WO 2011/003783 | A1 | 1/2011 |
| WO | WO 2011/014749 | A1 | 2/2011 |
| WO | WO 2011/082217 | A2 | 7/2011 |
| WO | WO 2014/003769 | A1 | 1/2014 |
| WO | WO 2014/150449 | A2 | 9/2014 |
| WO | WO 2014/159113 | A1 | 10/2014 |
| WO | WO 2014/164399 | A1 | 10/2014 |

OTHER PUBLICATIONS

Cantero et al., "Expression profiling of the *Arabidopsis annexin* gene family during germination, de-etiolation and abiotic stress," 2006, Plant Physiology and Biochemistry, 44: pp. 13-24.

Christensen et al., "Maize polyubiquitin genes: structure, thermal perturbation of expression and transcript splicing, and promoter activity following transfer to protoplasts by electroporation," 1992; Plant Mol. Biol. 18: pp. 675-689.

Cominelli et al., "Challenges and perspectives to improve crop drought and salinity tolerance," 2013, New Biotechnology, vol. 30, No. 4, pp. 355-361.

Crossway et al., "Integration of foreign DNA following microinjection of tobacco mesophyll protoplasts," 1986; Mol. Gen. Genet. 202: pp. 179-185.

De Pater et al., "The promoter of the rice gene GOS2 is active in various different monocot tissues and binds rice nuclear factor ASF-1," 1992; Plant. J. 2(6): pp. 837-844.

Divya et al., "Constitutive expression of mustard annexin, AnnBj1 enhances abiotic stress tolerance and fiber quality in cotton under stress," 2010, Plant Mol. Biol. 73: pp. 293-308.

Gibb et al., "Cotton growth responses to water stress," 2013, WATERpak section 3.1, pp. 117-126.

Gilmour, "Variance Structures Available in ASREML," 1999, Proc. Assoc. Advmt. Anim. Breed Genet.; vol. 13, pp. 416-419.

Good et al., "Engineering nitrogen use efficiency with alanine aminotransferase," 2007, Can J. Bot. 85: pp. 252-262.

Gorecka et al., "Peroxidase activity of annexin 1 from *Arabidopsis thaliana*," 2005, Biochem. Biophys. Res. Commun., 336(3), pp. 868-875.

Hu et al., "Genetic Engineering and Breeding of Drought-Resistant Crops," 2014. Annu. Rev. Plant Biol. vol. 65, pp. 715-741.

Hwang et al., "An *Arabidopsis thaliana* root-specific kinase homolog is induced by dehydration, ABA, and NaCl," The Plant Journal, 1995, 8(1), pp. 37-43.

International Search Report and Written Opinion issued in International Patent Application No. PCT/EP2016/067152, dated Oct. 26, 2016 (11 pages).

Ishida et al., "Wheat (*Triticum aestivum* L.) Transformation Using Immature Embryo's," 2015, Methods in Molecular Biology, 1223: pp. 189-198.

Jähne et al., "Genetic engineering of cereal crop plants: a review," 1995, Euphytica 85, pp. 35-44.

Jami et al., "Ectopic expression of an annexin from *Brassica juncea* confers tolerance to abiotic and biotic stress treatments in transgenic tobacco," Plant Physiology and Biochemistry, 2008, 46: pp. 1019-1030.

Jami et al., "Molecular cloning and characterization of five annexin genes from Indian mustard (*Brassica juncea* L. *czern* and *coss*)." 2009, Plant Physiology and Biochemistry 47: pp. 977-990.

Jefferson et al., "GUS fusions: Betta-glucuronidase as a sensitive and versatile gene fusion marker in higher plants," 1987, The EMBO Journal, 6(13), pp. 3901-3907.

Klein et al., "High-velocity microprojectiles for delivering nucleic acids into living cells," 1987, Nature, 327, pp. 70-73.

Konopka-Postupolska et al., "The Role of Annexin 1 in Drought Stress in *Arabidopsis*," 2009, Plant Physiology, 150: pp. 1394-1410.

Köster-Töpfer et al., "A class II patatin promoter is under developmental control in both transgenic potato and tobacco plants," Mol. Gen. Genet., 1989, 219: pp. 390-396.

Krens et al., "In vitro transformation of plant protoplasts with Ti-plasmid DNA," 1982, Nature 296: pp. 72-74.

Kuppa et al., "Water-Deficit Inducible Expression of a Cytokinin Biosynthetic Gene IPT Improves Drought Tolerance in Cotton," 2013, PLoS ONE 8(5): pp. 1-11.

Lagarde et al., "Tissue-specific expression of *Arabidopsis* AKT1 gene is consistent with a role in K+ nutrition," 1996, The Plant Journal, vol. 9(2), pp. 195-203.

Lawlor, "Genetic engineering to improve plant performance under drought: physiological evaluation of achievements, limitations, and possibilities," 2013, Journal of Experimental Botany, vol. 64(1), pp. 83-108.

Lepetit et al., "A plant histone gene promoter can direct both replication-dependent and -independent gene expression in transgenic plants," Mol. Gen. Genet., 1992, 231: pp. 276-285.

Liu et al., "Overexpression of Rice NAC Gene SNAC1 improves Drought and Salt Tolerance by Enhancing Root Development and Reducing Transpiration Rate in Transgenic Cotton," 2014, PLoS ONE 9(1): pp. 1-10.

Maheshwari et al., "In Vitro Culture of Wheat and Genetic Transformation—Retrospect and Prospect," Critical Reviews in Plant Science, 1995, 14(2), pp. 149-178 (Abstract).

Maqbool et al., "Gossypium arboreum GHSP26 Enhances Drought Tolerance in Gossypium Hirsutum," 2010, Biotechnol. Prog. 26(1): pp. 21-25.

McElroy et al., "Isolation of an Efficient Actin Promoter for Use in Rice Transformation," The Plant Cell, vol. 2, 1990, pp. 163-171.

Morran et al., "Improvement of stress tolerance of wheat and barley by modulation of expression of DREB/CBF factors," Plant Biotech. Journal, 2011, vol. 9, pp. 230-249.

Needleman et al., "A General Method Applicable to the Search for Similarities in the Amino Acid Sequence of Two Proteins," J. Mol. Biol., 1970. vol. 48, pp. 443-453.

Negrutiu et al., "Hybrid genes in the analysis of transformation conditions," Plant Molecular Biology, vol. 8, 1987, pp. 363-373.

Nehra et al., "Self-fertile transgenic wheat plants regenerated from isolated scutellar tissues following microprojectile bombardment with two distinct gene constructs," The Plant Journal, 1994, vol. 5(2), pp. 285-297.

Nilsson et al., "The Agrobacterium rhizogenes roIB and roIC promoters are expressed in pericycle cells competent to serve as root initials in transgenic hybrid aspen," 1997; Physiol. Plant. 100: pp. 456-462.

Pasapula et al., "Expression of an *Arabidopsis vacuolar* H+-pyrophosphatase gene (AVP1) in cotton improves drought- and

(56) References Cited

OTHER PUBLICATIONS salt tolerance and increases fibre yield in the field conditions," Plant Biotech. Journal, 2011, vol. 9, pp. 88-99.
Pien et al., "Local expression of expansin induces the entire process of leaf development and modifies leaf shape," 2001 PNAS 98(20): pp. 11812-11817.
Rodrigues et al., "The tonoplast intrinsic aquaporin (TIP) subfamily of Eucalyptus grandis: Characterization of EgTIP2, a root-specific and osmotic stress-responsive gene," Plant Science, 2013, 213: pp. 106-113.
Saad et al., "Promoter of the AISAP gene from the halophyte grass *Aeluropus littoralis* directs developmental-regulated, stress-inducible, and organ-specific gene expression in transgenic tobacco," Transgenic Res., 2011, 20: pp. 1003-1018.
Shillito et al., "High Efficiency Direct Gene Transfer to Plants," 1985; Bio/Technol. 3: pp. 1099-1102.
Takahashi et al., "Isolation and Analysis of the Expression of Two Genes for the 81-Kilodalton Heat-Shock Proteins from *Arabidopsis*," Plant Physiol. 1992, vol. 99, pp. 383-390.
Tardieu et al., "Any trait or trait-related allele can confer drought tolerance: just design the right drought scenario," 2012, J. Exp. Bot, vol. 63(1): pp. 25-31.
Wang et al., "Shoot-Specific Down-Regulation of Protein Farnesyltransferase (alpha-Subunit) for Yield Protection against Drought in Canola," Molecular Plant, vol. 2(1), 2009, pp. 191-200.
Yamaguchi-Shinozaki et al., "Characterization of the expression of a desiccation-responsive rd29 gene of *Arabidopsis thaliana* and analysis of its promoter in transgenic plants," Mol. Gen. Genet, 1993, 236: pp. 331-340.
Yamamoto et al., "Characterization of cis-Acting Sequences Regulating Root-Specific Gene Expression in Tobacco," The Plant Cell, 1991, vol. 3, pp. 371-382.
Yu et al., "*Arabidopsis* EDT1/HDG11 improves drought and salt tolerance in cotton and poplar and increases cotton yield in the field," Plant Biotechnology Journal, 2016, 14: pp. 72-84.
Yue et al., "Overexpression of the AtLOS5 gene increased abscisic acid level and drought tolerance in transgenic cotton," Journal of Experimental Botany, 2012, 63(10): pp. 3741-3748.
Zhang et al., "Overexpression of a cotton annexin gene, GhAnn1, enhances drought and salt stress tolerance in transgenic cotton," Plant Mol. Biol., 2015; 87: pp. 47-67.

* cited by examiner

```
Pbtg-26A10Gh      1 ATCCAAAAAAAGCAC--TTCAGATTATTGGTGATACCAAATGGCCAAACCC---TTCCTGACCAAAACAA
Pbtg-26D10Gh      1 ATGGAATAGAAAAACCATTCAAATCATACATTAATACAAA----CATACTCAAATTTCATTCAAATACAT

Pbtg-26A10Gh     66 TCGTGAAG------AATGTGACAGGAGGGG--------AGATTGAGGTTATCTTT---GAATGGATAGAT
Pbtg-26D10Gh     67 CCATAATGTTCCTTAATTGAGCCCTAGAGGCCCTAAAAATATTAAAGAAACAATTCGGGACTGAATCGAA

Pbtg-26A10Gh    119 GAAATCCTCCATCCAAAGAGTAGGACCTAATATGTAGAAA------------------CTCATGGCAGTT
Pbtg-26D10Gh    137 AACAT-----TTGGAAAATTTAGG----AAAAAGTTGAAAAATTTGGTCTGTAGGGGTCACATGGCCGTG

Pbtg-26A10Gh    171 GCATGAGTTGATTGCATGAGTTGAAGGTCCGATGCTGTTAAATCTATGGCTCTTAAATGTGCATCTTCTA
Pbtg-26D10Gh    198 TCAACATTCGA----AATAGGTACAG--ACAGTCGTGTCTTAGCCCGTGTCCATGCCAGTGTAACTTATT

Pbtg-26A10Gh    241 C-CTAGAAACAATCTTCTAAGCTTTTCATCCCTTCTTTCGCCATTGCATGCGCGACGGTATTTCCTCCTC
Pbtg-26D10Gh    262 GACTTGGGTCACAGGTCTAAGCTTTTCATCCCTTCTTTCGCCATTGCATGTGCGACAGTGTTTCCTCCTC

Pbtg-26A10Gh    310 TGGTTATGAAGTTAAAACGATA-TGTTAAGAAGTTTCGAGATAATGCATTCATATCCCAGGTAATCGGTC
Pbtg-26D10Gh    332 TAGCTATGAATTTAAAACAATAGTGCTAAGAAGCTTTGAGATAATGCTTT--------CA-------C---A

Pbtg-26A10Gh    379 TAATTTCATAATAGTAAAATAGGCGAAAAATTAAATGAAAAACTAAAATAA-TTCTTTTATAAAATTGGA
Pbtg-26D10Gh    386 TAATTTCATAATAGTAAAAGAGGCAAAAAATTAAATGAAAAGCTAAAATAATTTTTTTTATAAAATTGAA

Pbtg-26A10Gh    448 GGGTAAAAAAAATTATTATGCCTAAATATAACACATGTTATAAATACTCATAAGACGAAAAAGTTAAAAA
Pbtg-26D10Gh    456 GGG-CAAAAAAATCATCATGCCTAAATATAAAACATGTTATAAATACTCATAAGACGAAAAAGTTAAAAA

Pbtg-26A10Gh    518 ATTACAAAGGAAAGGACCTGATTGGAGCAATATGATAATATAGGGACTTGTTTAAAATGTTTTAAAGTTT
Pbtg-26D10Gh    525 ATTACAAAGGAAAGGACCTGATTGGAGCAGTATGATAATATAGGGACTTGTTTAAAATGTTTTAAAGTTT
```

FIGURE 1

```
Pbtg-26A10Gh   588 AGGACTTATTTAGAGTATCACCCATGATTTGGTATAATAAATAAAAAATCAGATGAGAGAGCCACCTCAT
Pbtg-26D10Gh   595 AGGACTTATTTAGAGTATCACCCATGATTTGGTATAATAAATAAAAAATCAGATGAGAGAGCCACCTCAT

Pbtg-26A10Gh   658 GAAAAAGACAAGAACATTACGTGTGATCCATTGCAGAAGAGGATAAAGTATGGACAAAATTTATAGATAT
Pbtg-26D10Gh   665 GAAAAAGACAAGAACATTACGTGTGATCCATTGCAGAAGAGGATAAAGTATGGACAAAATTTATAAATAT

Pbtg-26A10Gh   728 AATCTTGTACATCCCCCATACGTCACGGCTCTGTTCAGATCATAGGCCGAAAAGGCCTCCGTCTGTCTCA
Pbtg-26D10Gh   735 AATCTTGTACATCCCCCATACGTCACGGCTCTTTTCAGATCATAGGCCGAAAAGGCCTCAGTCTGTCTCA

Pbtg-26A10Gh   798 GTCCTCTACTTAAGGTACTCTTCTCTCTCTCCTTCCACATCAACTTTAACATTTTACTTCCTCTCTCTAC
Pbtg-26D10Gh   805 GTCCTCTACTTAAGGTACTCTTCTCTCTCTCCTTCGACATCAACTTCAACATATTACTTTCGCTCTCTTC

Pbtg-26A10Gh   868 CTTTGTTACTCAAGAAAAAGCAATGTATTAGAGATCGAGTTCATGATGAATTATTAAAAACCTTTCCTCT
Pbtg-26D10Gh   875 CTTTGGTACTCAAGAAAAAGCAAGGTAATAGAGATCGAGTTCATGATGAATTATTAAAAACCTTTCCTCT

Pbtg-26A10Gh   938 GTTTTTGTATATATTTCGGTTGGATTTTGAAGGAAACGTCTTTTTTT--CCTTTTT-TTTTGTGTGTAA
Pbtg-26D10Gh   945 GTTTTTGTATATATTTTGGTTGGATTTTGAAGGAAACTTCTTTTTTTTCCCTTTTTGTGTGTGTGCAA

Pbtg-26A10Gh  1005 TTGCA(GAG)ATG
Pbtg-26D10Gh  1015 TTGCA(GAG)ATG
```

Fig.1 continued

```
                                              GXGTD
AnnBj1      1 MATLKVSSSVPSPSEDAEQLKSAFDGWGTNEELIISILAHRSAEQRKLIRQTYHESFGEDLLKSLEKELTSDFERAILLW
AtAnn1      1 MATLKVSDSVPAPSDDAEQLRTAFEGWGTNEDLIISILAHRSAEQRKVIRQAYHETYGEDLLKTLDKELSNDFERAILLW
GhAnn1      1 MATLTVPTTVPSVSEDCEQLRKAFSGWGTNEGLIIDILGHRNAEQRNLIRKTYAETYGEDLLKALDKELSNDFERLVLLW
              **** *   **  * * ***  ** ****** *** **:** **** :** :* *::******:*:***: **** :***

AnnBj1     81 TLEPGERDALLVNEATKRWTSSNQVLMEVACTRTSTQLLHARQAYHARFKKSIEEDVAHHTTGDFRKLLVSLVSSYRYEG
AtAnn1     81 TLEPGERDALLANEATKRWTSSNQVLMEVACTRTSTQLLHARQAYHARYKKSLEEDVAHHTTGDFRKLLVSLVTSYRYEG
GhAnn1     81 ALDPAERDALLANEATKRWTSRNQVLMEIACTRSANQLLHARQAYHARYKKSLEEDVAHHTTGDFRKLLLPLVSSYRYEG
              :*:*:****** ********* ******:****:: ***********:***:***************::**:******
                                                        IRI
AnnBj1    161 EEVNMTLAKQEAKLIHEKIKDKHYNDEDFIRILSTRSKAQINATFNRYQDNHGEEILKSLEEGDEDDKFLGLLRSTIQCL
AtAnn1    161 DEVNMTLAKQEAKLVHEKIKDKHYNDEDVIRILSTRSKAQINATFNRYQDDHGEEILKSLEEGDDDDKFLALLRSTIQCL
GhAnn1    161 EEVNMTLAKTEAKLLHEKISNKAYSDDDVIRVLATRSKAQINATLNHYKNEYGNDINKDLK-ADPKDEFLALLRSTVKCL
              :******** ****:**** :* * *:* **:*:********* *:** ::*::* * *  :*  * **:*****: **
                                GXGTD
AnnBj1    241 TRPELYFVDVLRSAINKTGTDEGALTRIVTTRAEIDLKVIGQEYQRRNSIPLEKAITKDTRGDYEKMLIALLGEDDA
AtAnn1    241 TRPELYFVDVLRSAINKTGTDEGALTRIVTTRAEIDLKVIGEEYQRRNSIPLEKAITKDTRGDYEKMLVALLGEDDA
GhAnn1    240 VYPEKYFEKVLRLAINRRGTDEGALTRVVCTRAEVDLKLIADEYQRRNSVPLTRAIVKDTHGDYEKLLLVLAGHVEN
                ** **  *** ***: *********:* ****:***:*::*******:** :** ***:*****:*: * *  :
```

Figure 2

```
AnnBj1      1 ATGGCGACTCTTAAGGTTTCTTCTTCTGTTCCTTCTCCCTCTGAAGATGCTGAGCAATTGAAAAGCGCATTTGATGGATG
AtAnn1      1 ATGGCGACTCTTAAGGTTTCTGATTCTGTTCCTGCTCCTTCTGATGATGCTGAGCAATTGAGAACCGCTTTTGAAGGATG
GhAnn1      1 ATGGCCACTCTTACAGTGCCCACGACAGTTCCTTCAGTGTCTGAAGATTGTGAACAACTAAGAAAAGCCTTTTCAGGATG
              *****:*******::**::*: ;::*:******;*::: *****;***::***:***:*:*.** :** ***::.*****

AnnBj1     81 GGGTACCAACGAGGAATTGATCATATCAATCTTGGCTCACAGAAGTGCTGAACAGAGGAAGCTGATCAGGCAAACATACC
AtAnn1     81 GGGTACGAACGAGGACTTGATCATATCAATCTTGGCTCACAGAAGTGCTGAACAGAGGAAAGTCATCAGGCAAGCATACC
GhAnn1     81 GGGAACTAATGAGGGCTTAATCATAGATATATTGGGTCACAGAAATGCGGAGCAACGAAACTTGATTCGAAAAACCTACG
              ***:** **:****:;**:******:::**:****:*******:***:**:**::*:**  *;**::*::**;*:***:

AnnBj1    161 ATGAATCCTTTGGAGAGGATCTTCTTAAGAGTCTTGAGAAGGAACTTACAAGCGACTTCGAGAGAGCCATCTTGCTCTGG
AtAnn1    161 ACGAAACCTACGGCGAAGACCTTCTCAAGACTCTTGACAAGGAGCTCTCTAACGATTTCGAGAGAGCTATCTTGTTGTGG
GhAnn1    161 CTGAAACCTATGGAGAGGATCTCCTCAAGGCACTAGACAAGGAGCTCTCGAATGACTTTGAGAGGCTGGTTCTGCTTTGG
              :;***.***.;**;**;**;**:**.***:.:**:**.*****.**..* *.:**;**:*****::: :*::**;* ***

AnnBj1    241 ACTCTTGAACCGGGTGAACGTGATGCCTTATTGGTTAATGAAGCTACCAAAAGATGGACTTCAAGCAACCAAGTGCTTAT
AtAnn1    241 ACTCTTGAACCCGGTGAGCGTGATGCTTTATTGGCTAATGAAGCTACAAAAAGATGGACTTCAAGCAACCAAGTTCTTAT
GhAnn1    241 GCTCTTGATCCTGCTGAACGTGATGCCCTTTTGGCTAATGAAGCCACCAAAAGGTGGACTTCAAGAAATCAAGTCCTTAT
              :*******:** *:***;********;:*:****.*********:**;*****:**********:**:***** *****

AnnBj1    321 GGAAGTAGCTTGCACTAGGACCTCTACGCAGCTTCTTCACGCTAGGCAAGCTTACCACGCTCGCTTCAAGAAGTCTATTG
AtAnn1    321 GGAAGTTGCTTGCACAAGGACATCAACGCAGCTGCTTCACGCTAGGCAAGCTTACCATGCTCGCTACAAGAAGTCTCTTG
GhAnn1    321 GGAAATAGCCTGCACAAGGTCTGCCAACCAACTGCTTCACGCAAGGCAGGCTTATCATGCTCGTTATAAGAAGTCGCTTG
              ****:*;**:*****.***:* :* *::**:**.********:*****:*****:**.*****:*.:********:.***

AnnBj1    401 AAGAGGATGTCGCTCACCACACCACCGGTGACTTCAGAAAGCTTTTGGTTTCTCTTGTTAGCTCATACAGGTACGAAGGG
AtAnn1    401 AAGAGGACGTTGCTCACCACACTACCGGTGACTTCAGAAAGCTTTTGGTTTCTCTTGTTACCTCATACAGGTACGAAGGA
GhAnn1    401 AAGAGGACGTTGCTCATCACACGACTGGGGACTTCCGTAAGCTCCTCCTACCTCTAGTGAGTTCATACAGATATGAGGGA
              *******.**.*****:***** **:**:******:*:*****::*::*::****:**:*;:*******:**:**:**.
```

Figure 3

```
AnnBj1      481 GAAGAGGTAAACATGACATTGGCAAAGCAAGAGGCTAAGCTGATTCATGAGAAAATCAAGGACAAGCATTACAATGATGA
AtAnn1      481 GATGAAGTGAACATGACATTGGCTAAGCAAGAAGCTAAGCTGGTCCATGAGAAAATCAAGGACAAGCACTACAATGATGA
GhAnn1      481 GAGGAGGTGAACATGACTCTGGCAAAAACAGAGGCGAAGTTGCTTCATGAGAAAATTTCAAACAAAGCTTACAGTGATGA
                ** **;**.*******::******:::***;**:***:** *;**********::::****:::;****:******

AnnBj1      561 AGATTTCATAAGGATTTTGTCCACAAGGAGCAAAGCACAGATCAATGCTACCTTCAATCGCTATCAAGATAATCACGGCG
AtAnn1      561 GGATGTTATTAGAATCTTGTCCACAAGAAGCAAAGCTCAGATCAATGCTACTTTTAACCGTTACCAAGATGATCATGGCG
GhAnn1      561 CGATGTCATAAGGGTTTTGGCTACAAGAAGCAAGGCACAGATCAATGCAACTCTGAATCACTACAAAAATGAATATGGAA
                 ***.*;**;**;:*;***:*:*****.*****:**;**********:**.:* **;* ***.:**:**.*::*;**::

AnnBj1      641 AGGAAATCCTCAAGAGCCTTGAGGAAGGAGATGAAGACGACAAGTTCCTAGGGCTGTTGAGGTCAACCATTCAATGCTTG
AtAnn1      641 AGGAAATTCTCAAGAGTCTTGAGGAAGGAGATGATGATGACAAGTTCCTTGCACTTTTGAGGTCAACCATTCAGTGCTTG
GhAnn1      641 ATGACATAAACAAGGACTTGAAG---GCTGACCCTAAGGATGAGTTCCTTGCACTACTAAGGTCCACAGTGAAGTGCTTG
                *:**:** ::****:: :*::**:::*::**:::.:* **::*******.*..** :*:*****:**::*::*.******

AnnBj1      721 ACAAGACCTGAGCTTTACTTTGTGGATGTTCTTCGTTCAGCGATCAACAAAACGGGAACAGACGAAGGAGCTCTCACTAG
AtAnn1      721 ACAAGACCAGAGCTTTACTTTGTCGATGTTCTTCGTTCAGCAATCAACAAAACTGGAACTGATGAAGGAGCACTCACTAG
GhAnn1      718 GTCTATCCGGAAAAGTATTTTGAGAAGGTTCTTCGCCTAGCAATCAATAGACGAGGAACGGATGAAGGAGCTCTTACAAG
                ::::::** **::::** ****:::*:********:::***.*****:*:*:: ***** **.********;**:**:**

AnnBj1      801 AATTGTGACCACAAGAGCTGAGATTGACTTGAAAGTCATTGGACAAGAGTACCAAAGAAGGAACAGCATTCCATTGGAGA
AtAnn1      801 AATTGTGACCACAAGAGCTGAGATTGACTTGAAGGTCATTGGAGAGGAGTACCAGCGCAGGAACAGCATTCCTTTGGAGA
GhAnn1      798 AGTTGTTTGCACTAGGGCTGAGGTTGATCTAAAGATCATAGCAGATGAGTATCAGCGAAGGAACAGTGTCCCACTGACTC
                *:****:::***:**:******:****::*:**.:****:*:*.* *****:**..*;*******::*:**;:**::::

AnnBj1      881 AAGCCATTACCAAAGACACTCGTGGAGATTACGAGAAGATGCTCATCGCACTTCTCGGTGAAGATGATGCTTAA
AtAnn1      881 AAGCTATTACCAAAGACACTCGTGGAGATTACGAGAAGATGCTCGTCGCACTTCTCGGTGAAGATGATGCTTAA
GhAnn1      878 GTGCCATTGTCAAGGACACTCATGGAGACTATGAAAAATTGCTGCTGGTACTTGCAGGACATGTGGAGAATTGA
                ::**;***::***:******:*****:**:**:**::****: *:*:****::**::*:*::**:::**:*
```

Figure 3 continued

SEQUENCE LISTING

```
<160> NUMBER OF SEQ ID NOS: 33

<210> SEQ ID NO 1
<211> LENGTH: 4556
<212> TYPE: DNA
<213> ORGANISM: Artificial Sequence
<220> FEATURE:
<223> OTHER INFORMATION: T-DNA Pbtg-26Bn::GUS

<400> SEQUENCE: 1

cggcaggata tattcaattg taaatggctc catggcgatc gctctagagg atctgcgatc     60

tagtaacata gatgacaccg cgcgcgataa tttatcctag tttgcgcgct atattttgtt    120

ttctatcgcg tattaaatgt ataattgcgg gactctaatc ataaaaaccc atctcataaa    180

taacgtcatg cattacatgt taattattac atgcttaacg taattcaaca gaaattatat    240

gataatcatc gcaagaccgg caacaggatt caatcttaag aaactttatt gccaaatgtt    300

tgaacgatct gcttcggatc ctagaacgcg tgatctcaga tctcggtgac gggcaggacc    360

ggacggggcg gtaccggcag gctgaagtcc agctgccaga aacccacgtc atgccagttc    420

ccgtgcttga agccggccgc ccgcagcatg ccgcgggggg catatccgag cgcctcgtgc    480

atgcgcacgc tcgggtcgtt gggcagcccg atgacagcga ccacgctctt gaagccctgt    540

gcctccaggg acttcagcag gtgggtgtag agcgtggagc ccagtcccgt ccgctggtgg    600

cggggggaga cgtacacggt cgactcggcc gtccagtcgt aggcgttgcg tgccttccag    660

gggcccgcgt aggcgatgcc ggcgacctcg ccgtccacct cggcgacgag ccagggatag    720

cgctcccgca gacggacgag gtcgtccgtc cactcctgcg gttcctgcgg ctcggtacgg    780

aagttgaccg tgcttgtctc gatgtagtgg ttgacgatgg tgcagaccgc cggcatgtcc    840

gcctcggtgg cacggcggat gtcggccggg cgtcgttctg ggtccatggt tatagagaga    900

gagatagatt tatagagaga gactggtgat ttcagcgtgt cctctccaaa tgaaatgaac    960

ttccttatat agaggaaggg tcttgcgaag gatagtggga ttgtgcgtca tcccttacgt   1020

cagtggagat gtcacatcaa tccacttgct ttgaagacgt ggttggaacg tcttcttttt   1080

ccacgatgct cctcgtgggt gggggtccat ctttgggacc actgtcggca gaggcatctt   1140

gaatgatagc ctttccttta tcgcaatgat ggcatttgta ggagccacct tccttttcta   1200

ctgtcctttc gatgaagtga cagatagctg ggcaatggaa tccgaggagg tttcccgaaa   1260

ttatcctttg ttgaaaagtc tcaatagccc tttggtcttc tgagactgta tctttgacat   1320

ttttggagta gaccagagtg tcgtgctcca ccatgttgac gaagattttc ttcttgtcat   1380

tgagtcgtaa aagactctgt atgaactgtt cgccagtctt cacggcgagt tctgttagat   1440

cctcgatttg aatcttagac tccatgcatg gccttagatt cagtaggaac taccttttta   1500

gagactccaa tctctattac ttgccttggt ttatgaagca agccttgaat cgtccatact   1560

ggaatagtac ttctgatctt gagaaatatg tctttctctg tgttcttgat gcaattagtc   1620
```

-continued

```
ctgaatcttt tgactgcatc tttaaccttc ttgggaaggt atttgatctc ctggagattg   1680
ttactcgggt agatcgtctt gatgagacct gctgcgtagg aacgcggccg ctgtacaggg   1740
cccgggcata tggcgcgtta gggataacag ggtaattacg tattaattaa ggcgcgtcct   1800
gcaggaagct tgcatgcctg caggtcactg gattttggtt ttaggaatta gaaattttat   1860
tgatagaagt attttacaaa tacaaataca tactaagggt ttcttatatg ctcaacacat   1920
gagcgaaacc ctataagaac cctaattccc ttatctggga actactcaca cattattctg   1980
gagaaaaata gagagagata gatttgtaga gagagactgg tgatttttgc gccgggtacc   2040
gagctcggta gcaattcccg aggctgtagc cgacgatggt gcgccaggag agttgttgat   2100
tcattgtttg cctccctgct gcggtttttc accgaagttc atgccagtcc agcgtttttg   2160
cagcagaaaa gccgccgact tcggtttgcg gtcgcgagtg aagatccctt tcttgttacc   2220
gccaacgcgc aatatgcctt gcgaggtcgc aaaatcggcg aaattccata cctgttcacc   2280
gacgacggcg ctgacgcgat caaagacgcg gtgatacata tccagccatg cacactgata   2340
ctcttcactc cacatgtcgg tgtacattga gtgcagcccg gctaacgtat ccacgccgta   2400
ttcggtgatg ataatcggct gatgcagttt ctcctgccag gccagaagtt ctttttccag   2460
taccttctct gccgtttcca aatcgccgct ttggacatac catccgtaat aacggttcag   2520
gcacagcaca tcaaagagat cgctgatggt atcggtgtga gcgtcgcaga acattacatt   2580
gacgcaggtg atcggacgcg tcgggtcgag tttacgcgtt gcttccgcca gtggcgcgaa   2640
atattcccgt gcaccttgcg gacgggtatc cggttcgttg gcaatactcc acatcaccac   2700
gcttgggtgg tttttgtcac gcgctatcag ctctttaatc gcctgtaagt gcgcttgctg   2760
agtttccccg ttgactgcct cttcgctgta cagttctttc ggcttgttgc ccgcttcgaa   2820
accaatgcct aaagagaggt taaagccgac agcagcagtt tcatcaatca ccacgatgcc   2880
atgttcatct gcccagtcga gcatctcttc agcgtaaggg taatgcgagg tacggtagga   2940
gttggcccca atccagtcca ttaatgcgtg gtcgtgcacc atcagcacgt tatcgaatcc   3000
tttgccacgc aagtccgcat cttcatgacg accaaagcca gtaaagtaga acggtttgtg   3060
gttaatcagg aactgttcgc ccttcactgc cactgaccgg atgccgacgc gaagcgggta   3120
gatatcacac tctgtctggc ttttggctgt gacgcacagt tcatagagat aaccttcacc   3180
cggttgccag aggtgcggat tcaccacttg caaagtcccg ctagtgcctt gtccagttgc   3240
aaccacctgt tgatccgcat cacgcagttc aacgctgaca tcaccattgg ccaccacctg   3300
ccagtcaaca gacgcgtggt tacagtcttg cgcgacatgc gtcaccacgg tgatatcgtc   3360
cacccaggtg ttcggcgtgg tgtagagcat tacgctgcga tggattccgg catagttaaa   3420
gaaatcatgg aagtaagact gctttttctt gccgttttcg tcggtaatca ccattcccgg   3480
cgggatagtc tgccagttca gttcgttgtt cacacaaacg gtgatacctg cacatcaaca   3540
aattttggtc atatattaga aaagttataa attaaaatat acacacttat aaactacaga   3600
aaagcaattg ctatatacta cattctttta ttttgaaaaa aatatttgaa atattatatt   3660
actactaatt aatgataatt attatatata tatcaaaggt agaagcagaa acttacgtac   3720
acttttcccg gcaataacat acggcgtgac atcggcttca aatggcgtat agccgccctg   3780
atgctccatc acttcctgat tattgaccca cactttgccg taatgagtga ccgcatcgaa   3840
acgcagcacg atacgctggc ctgcccaacc tttcggtata aagacttcgc gctgatacca   3900
gacgttgccc gcataattac gaatatctgc atcggcgaac tgatcgttaa aactgcctgg   3960
cacagcaatt gcccggcttt cttgtaacgc gctttcccac caacgctgat caattccaca   4020
```

gttttcgcga tccagactga atgcccacag gccgtcgagt tttttgattt cacgggttgg 4080
ggtttctaca ggacggacca tggcgagatc aactaagacg aagggggcgg cagagcagcg 4140
aggatcctta aggatatcaa acagtgatta aagaatcaat cacctctctt agtattatcg 4200
atggtatcaa agaatggagt tttccgatta tacgtttgat cagagagtct ttataagagg 4260
aagtgagtga gagagagaga gagagagaga gacgtgtacg acttgtaagt aaagttggaa 4320
cagcgattgg accgaaaacg aaagctgagc tgttgtgtca atccccccttt tggcttgatt 4380 cactcggatc atatgaagtt ttgtcacgtg tcctacgttt ctttttccgg gtcgggatat 4440
accccgatta ggatccgttg acctgcaggt cgacatttat cgaattcgag ctcgagttaa 4500
ggcgcgccgt tgcaggtcga cggccgagta ctggcaggat atataccgtt gtaatt 4556

<210> SEQ ID NO 2
<211> LENGTH: 20
<212> TYPE: DNA
<213> ORGANISM: Artificial Sequence
<220> FEATURE:
<223> OTHER INFORMATION: primer KVA07-32

<400> SEQUENCE: 2
tgtagttgac cagctacttg 20

<210> SEQ ID NO 3
<211> LENGTH: 19
<212> TYPE: DNA
<213> ORGANISM: Artificial Sequence
<220> FEATURE:
<223> OTHER INFORMATION: primer KVA07-34

<400> SEQUENCE: 3
ttaacacccg acgtgtttc 19

<210> SEQ ID NO 4
<211> LENGTH: 2164
<212> TYPE: DNA
<213> ORGANISM: Gossypium hirsutum

<400> SEQUENCE: 4
ttagaatata atgattaatt agaaaaaaaa ttataaaact tctatgtaag cataaaatta 60
attctagtaa atataaagca taatgactta tttgaccatt tatttaattt tttacatatt 120
ttagttattg tggtttttttt tgggtcaaat tacctgaata aatgaaaaag tgaacattta 180
attaattttt taaaatttaa aaattaatta aatgctgaca tgccatctat attagaatcc 240
acatgtatgc tatgttagta aagttaataa acatgaactt ttccatccat tttaggatga 300
tttgacaaaa actacaaatt taaggactaa aaaagataat tttttttaaa taatttgttt 360
agtttattat tataggtcta gatcaaaaag tctaataaaa catttgaagc aaaataaaaa 420
aaaacatagc aacaaaaata aaataaaact aaaacaacct ctagaaactt catccaaaaa 480
aagcacttca gattattggt gataccaaat ggccaaaccc ttcctgacca aaacaatcgt 540
gaagaatgtg acaggagggg agattgaggt tatctttgaa tggatagatg aaatcctcca 600
tccaaagagt aggacctaat atgtagaaac tcatggcagt tgcatgagtt gattgcatga 660
gttgaaggtc cgatgctgtt aaatctatgg ctcttaaatg tgcatcttct acctagaaac 720
aatcttctaa gcttttcatc ccttctttcg ccattgcatg cgcgacggta tttcctcctc 780
tggttatgaa gttaaaacga tatgttaaga agtttcgaga taatgcattc atatcccagg 840

-continued

```
taatcggtct aatttcataa tagtaaaata ggcgaaaaat taaatgaaaa actaaaataa    900

ttcttttata aaattggagg gtaaaaaaaa ttattatgcc taaatataac acatgttata    960

aatactcata agacgaaaaa gttaaaaaat tacaaaggaa aggacctgat tggagcaata   1020

tgataatata gggacttgtt taaaatgttt taaagtttag gacttattta gagtatcacc   1080

catgatttgg tataataaat aaaaaatcag atgagagagc cacctcatga aaaagacaag   1140

aacattacgt gtgatccatt gcagaagagg ataaagtatg gacaaaattt atagatataa   1200

tcttgtacat cccccatacg tcacggctct gttcagatca taggccgaaa aggcctccgt   1260

ctgtctcagt cctctactta aggtactctt ctctctctcc ttccacatca actttaacat   1320

tttacttcct ctctctacct ttgttactca agaaaaagca atgtattaga gatcgagttc   1380

atgatgaatt attaaaaacc tttcctctgt ttttgtatat atttcggttg gattttgaag   1440

gaaacttctt tttttccttt ttttttgtg tgtaattgca gagatgggtt tttcaaggaa   1500

agagtacgag ttcttgagcg agatcggatt gagttctggc aatttgggat gttttgtgaa   1560

tggcacctgg aaaggaagtg gccctgtggt ttctactctt aatcctgcca ataatcaggt   1620

tctatttttt agaatgtttt gtttttttcat gctggataag atgggtttat tattaattgt   1680

ggtgagactg atgggattgt ctttctgaga aaataacata cattcaatct catcgtattt   1740

ttccgacttg gatcctcctc tataaatctt taaaataaac caatgttaag acttgcgctt   1800

ttatggagtg gcagtattct tggttttaat ttttagcttt tactcatatg ctgtaggttt   1860

tcttttattt ttgtttctgc attttaaaga tattattaat gttttacaaa cacacttgct   1920

agttgctgag tactaaacta cttgatccag gcatttagaa actattagtt tcttcactcc   1980

tataatttta gtattattta aatgttgctt ttgcagaaaa ttgccgaagt tagtgaggct   2040

tccatccaag actatgagga agggatgcaa gcttgcagtg aagcagcaaa gatttggatg   2100

caggtaagat ggacggatac catactctta aacttaatat ttcggttgga aatttacatt   2160

tctt                                                                2164
```

<210> SEQ ID NO 5
<211> LENGTH: 4086
<212> TYPE: DNA
<213> ORGANISM: Gossypium hirsutum

<400> SEQUENCE: 5

```
tctcgagaaa ggcatgattg aattgtaccg catgtctaga catttctaaa agagaacatt     60

tagaacctca ctttgccaca taccgaaatt atctgtgcca tcgaagatct ccactactga    120

tctcgcccac atggacgatg ttggggctat tgatgttgta gatgtggatc attttggatt    180

ttccaccatt tcagctataa tatttcaata tgctaaagga aatctatgct gatgtggaag    240

attagtttaa actgcaacca tagagcatac ttcgaataac cttcggctct aataccccctt    300

gttgtgcaaa tagggtaaaa aggagtaaat tattgtacta gaaaaccaca ctaggtttag    360

tttccaagaa agattagata ggtcacaaac ggtcctattt aaaacccaac ctcctaaata    420

gaatctccta caatgtaatt taatagcaca atatatcact acaattatac tctataaaaa    480

attgaaagat aaataaaaat aataaagaac acccgaaagt tcacgatgtt cgacaaatta    540

tgcctacgtc atcgaacact accaaatata ttcattataa aagatacaag tgaagaataa    600

aaaaagagaa aaaatttacc ttattaagaa aatgacaatt ttggatgatt caaaggtgga    660

gaaacaaccc tatttatagt agcataaatt ctccacaatc ttgtatctca catctaaaac    720

aaccctattc attgcatatt gaattatagc caagggccaa ttgtgaatta accctttttt    780
```

```
aaactacata caattataaa acttataaaa ttacttaaac atatatttct cttttcgtct    840
atttataaat aaacataaat aaaataggta aaaacttaaa taaatcagta taaattttag    900
ttacaataat ttaattatta aaaattaagt attattaatt aagtatggta aataaatttt    960
tacatttcat gtattataga atttattcat aaatttaaaa agaaaagaaa aagaatttta   1020
taaatttaat ataaatgatt atattttaat aatttaattg ctaaaagtaa tttaaattag   1080
tatagaaatt attatatatt tattgcattt tataaaatta atgcaattaa ataatttcta   1140
attaattata aatcttaaaa gtagtttaat tataaaacca attgttattt agggtaatta   1200
tttgatatat cattagtgga gtttttttaga ctccacaagc gggttgagca tgtgacaagt  1260
gtcatattaa tttatgtaat tagctttttc ttcttttact acatcctata atacactaat   1320
caaatcctta attcacttgt gaagtctaaa acactctatt ggcggtgtat caaataattt   1380
ttctattatt tgtatttatc tataaaaata aagattaaaa tatgccttag gtccctgtac   1440
ttttcataaa tttgaaattt aatctctata tttttatttt caagaattta gtccctctac   1500
tttccagatt ttaaaattca agtccaattg ttaatgctat taattttttg ttaaatttgt   1560
tggtgtgaca ttttgaaata gaaaaaaaat gctcacttga tagaaatgta actaaaaaaa   1620
tatgttataa taaacttgca tttaacagaa taatcttaaa agtgataaca attggacttg   1680
aatttgaaat ctaaaaagta ggaaactaaa ttcctaaaaa ttaaagtaca tagtctaact   1740
tccaaattta ccacgagtac aaggagttaa gacatatttt aaccaaaaat aaatgagtaa   1800
tgaataagaa gaaaaagaac accaattcga aacttagaga taacattatt gggaaggaca   1860
acatcgaacc tcgaactata acatcaatga aaaatataca cgattactat tcgtaaaaca   1920
ttatagaagt ttcatggtta gaggttgaga cgtaaatttt atttatttat tttacttggt   1980
tggtgatcgc ctcttgacgt accaactgta acacccctaa cccgtattac gtcgcctaaa   2040
caaggttaag gagtattacc ggacaaatgg aatagaaaaa ccattcaaat catacattaa   2100
tacaaacata ctcaaatttc attcaaatac atccataatg ttccttaatt gagccctaga   2160
ggccctaaaa atattaaaga aacaattcgg gactgaatcg aaaacatttg gaaaatttag   2220
gaaaaagttg aaaaatttgg tctgtagggg tcacatggcc gtgtcaacat tcgaaatagg   2280
tacagacagt cgtgtcttag cccgtgtcca tgccagtgta acttattgac ttgggtcaca   2340
ggtctaagct tttcatccct tctttcgcca ttgcatgtgc gacagtgttt cctcctctag   2400
ctatgaattt aaaacaatag tgctaagaag ctttgagata atgctttcac ataatttcat   2460
aatagtaaaa gaggcaaaaa attaaatgaa aagctaaaat aatttttttt ataaaattga   2520
agggcaaaaa aaatcatcat gcctaaatat aaaacatgtt ataaatactc ataagacgaa   2580
aaagttaaaa aattacaaag gaaaggacct gattggagca gtatgataat atagggactt   2640
gtttaaaatg ttttaaagtt taggacttat ttagagtatc acccatgatt tggtataata   2700
aataaaaaat cagatgagag agccacctca tgaaaaagac aagaacatta cgtgtgatcc   2760
attgcagaag aggataaagt atggacaaaa tttataaata taatcttgta catcccccat   2820
acgtcacggc tcttttcaga tcataggccg aaaaggcctc agtctgtctc agtcctctac   2880
ttaaggtact cttctctctc tccttcgaca tcaacttcaa catattactt tcgctctctt   2940
cctttggtac tcaagaaaaa gcaaggtaat agagatcgag ttcatgatga attattaaaa   3000
acctttcctc tgtttttgta tatattttgg ttggattttg aaggaaactt cttttttttc   3060
cctttttgtg tgtgtgtgca attgcagaga tgggtttttc aaggaaagag tacgagttct   3120
```

-continued tgagcgagat cggattgagt tctggcaatt tgggatgttt tgtgaatggc acctggaaag 3180
gaagtggccc tgtggtttct actcttaatc ctgcccataa tcaggttcta tttttaagaa 3240
tgttttgttt ttttatgcta gataagatgg gtttattatt aattgtggtg agactgatag 3300
aattgtcttt ctgagaaaat aacttacatt caatctcatc gtatttttcc gacttggatc 3360
ctcctctata aatctttaaa ataaaccaat gttaagactt gctcttctat tgagtggcag 3420
tattcttggt tttaattttt agcttttact catatgctgc aggttttctc ttatttttgc 3480
ttctgcattt taaagataat agtaatgttt tacaaacaca cttgctagtt actgagtact 3540
aaactacttg atccagtcat ttagaaacta ttagtttctt cactcctata attttagtat 3600
tatttcaatg ttgcttttgc agaaaattgc cgaagttagt gaggcttcca tccaagacta 3660
tgaggaaggg atgcaagctt gcagtgaagc agcaaagatt tggatgcagg taagatggac 3720
ggataccata ctcttaaact ttatatttcg gttggaaatt tacatttctt aatgccattt 3780
ttacttctct gaacctttta tgctttattt attgtttcag gttccagccc ctaagagagg 3840
tgacatagtt cgacaaatag gtgatgcatt gagatccaaa ctacagcagc ttggccgcct 3900
tgtttctctt gagatgggaa aaattcttcc cgaaggaatt ggggaagttc aagtatgtta 3960
tgcggccttg tcactgttat cacattggtc tctttgcata taatatgtca taaggcagcc 4020
catattgaac tacatgagcc atttagcatt tggttgagtt agtttaaata ttttcttcaa 4080
tcttca 4086

<210> SEQ ID NO 6
<211> LENGTH: 1009
<212> TYPE: DNA
<213> ORGANISM: Gossypium hirsutum

<400> SEQUENCE: 6
atccaaaaaa agcacttcag attattggtg ataccaaatg gccaaaccct tcctgaccaa 60
aacaatcgtg aagaatgtga caggagggga gattgaggtt atctttgaat ggatagatga 120
aatcctccat ccaaagagta ggacctaata tgtagaaact catggcagtt gcatgagttg 180
attgcatgag ttgaaggtcc gatgctgtta aatctatggc tcttaaatgt gcatcttcta 240
cctagaaaca atcttctaag cttttcatcc cttctttcgc cattgcatgc gcgacggtat 300
ttcctcctct ggttatgaag ttaaaacgat atgttaagaa gtttcgagat aatgcattca 360
tatcccaggt aatcggtcta atttcataat agtaaaatag gcgaaaaatt aaatgaaaaa 420
ctaaaataat tcttttataa aattggaggg taaaaaaaat tattatgcct aaatataaca 480
catgttataa atactcataa gacgaaaaag ttaaaaaatt acaaaggaaa ggacctgatt 540
ggagcaatat gataatatag ggacttgttt aaaatgtttt aaagtttagg acttatttag 600
agtatcaccc atgatttggt ataataaata aaaaatcaga tgagagagcc acctcatgaa 660
aaagacaaga acattacgtg tgatccattg cagaagagga taaagtatgg acaaaattta 720
tagatataat cttgtacatc ccccatacgt cacggctctg ttcagatcat aggccgaaaa 780
ggcctccgtc tgtctcagtc ctctacttaa ggtactcttc tctctctcct tccacatcaa 840
ctttaacatt ttacttcctc tctctacctt tgttactcaa gaaaaagcaa tgtattagag 900
atcgagttca tgatgaatta ttaaaaacct ttcctctgtt tttgtatata tttcggttgg 960
attttgaagg aaacgtcttt ttttcctttt ttttttgtgt gtaattgca 1009

<210> SEQ ID NO 7
<211> LENGTH: 1022

<212> TYPE: DNA
<213> ORGANISM: Gossypium hirsutum

<400> SEQUENCE: 7
atggaataga aaaaccattc aaatcataca ttaatacaaa catactcaaa tttcattcaa 60
atacatccat aatgttcctt aattgagccc tagaggccct aaaaatatta aagaaacaat 120
tcgggactga atcgaaaaca tttggaaaat ttaggaaaaa gttgaaaaat ttggtctgta 180
ggggtcacat ggccgtgtca acattcgaaa taggtacaga cagtcgtgtc ttagcccgtg 240
tccatgccag tgtaacttat tgacttgggt cacaggtcta agcttttcat cccttctttc 300
gccattgcat gtgcgacagt gtttcctcct ctagctatga atttaaaaca atagtgctaa 360
gaagctttga gataatgctt tcacataatt tcataatagt aaaagaggca aaaaattaaa 420
tgaaaagcta aaataatttt ttttataaaa ttgaagggca aaaaaatcat catgcctaaa 480
tataaaacat gttataaata ctcataagac gaaaaagtta aaaaattaca aaggaaagga 540
cctgattgga gcagtatgat aatataggga cttgtttaaa atgttttaaa gtttaggact 600
tatttagagt atcacccatg atttggtata ataaataaaa aatcagatga gagagccacc 660
tcatgaaaaa gacaagaaca ttacgtgtga tccattgcag aagaggataa agtatggaca 720
aaatttataa atataatctt gtacatcccc catacgtcac ggctcttttc agatcatagg 780
ccgaaaaggc ctcagtctgt ctcagtcctc tacttaaggt actcttctct ctctccttcg 840
acatcaactt caacatatta ctttcgctct cttcctttgg tactcaagaa aaagcaaggt 900
aatagagatc gagttcatga tgaattatta aaaacctttc ctctgttttt gtatatattt 960
tggttggatt ttgaaggaaa cttctttttt ttccctttttt gtgtgtgtgt gcaattgcaa 1020
cc 1022

<210> SEQ ID NO 8
<211> LENGTH: 4734
<212> TYPE: DNA
<213> ORGANISM: Artificial Sequence
<220> FEATURE:
<223> OTHER INFORMATION: T-DNA Pbtg-26GhA0.6::GUS

<400> SEQUENCE: 8
cggcaggata tattcaattg taaatggctc catggcgatc gctctagagg atctgcgatc 60
tagtaacata gatgacaccg cgcgcgataa tttatcctag tttgcgcgct atattttgtt 120
ttctatcgcg tattaaatgt ataattgcgg gactctaatc ataaaaaccc atctcataaa 180
taacgtcatg cattacatgt taattattac atgcttaacg taattcaaca gaaattatat 240
gataatcatc gcaagaccgg caacaggatt caatcttaag aaactttatt gccaaatgtt 300
tgaacgatct gcttcggatc ctagaacgcg tgatctcaga tctcggtgac gggcaggacc 360
ggacggggcg gtaccggcag gctgaagtcc agctgccaga aacccacgtc atgccagttc 420
ccgtgcttga agccggccgc ccgcagcatg ccgcgggggg catatccgag cgcctcgtgc 480
atgcgcacgc tcgggtcgtt gggcagcccg atgacagcga ccacgctctt gaagccctgt 540
gcctccaggg acttcagcag gtgggtgtag agcgtggagc ccagtcccgt ccgctggtgg 600
cggggggaga cgtacacggt cgactcggcc gtccagtcgt aggcgttgcg tgccttccag 660
gggcccgcgt aggcgatgcc ggcgacctcg ccgtccacct cggcgacgag ccagggatag 720
cgctcccgca gacggacgag gtcgtccgtc cactcctgcg gttcctgcgg ctcggtacgg 780
aagttgaccg tgcttgtctc gatgtagtgg ttgacgatgg tgcagaccgc cggcatgtcc 840

-continued

```
gcctcggtgg cacggcggat gtcggccggg cgtcgttctg ggtccatggt tatagagaga    900
gagatagatt tatagagaga gactggtgat ttcagcgtgt cctctccaaa tgaaatgaac    960
ttccttatat agaggaaggg tcttgcgaag gatagtggga ttgtgcgtca tcccttacgt   1020
cagtggagat gtcacatcaa tccacttgct ttgaagacgt ggttggaacg tcttcttttt   1080
ccacgatgct cctcgtgggt gggggtccat ctttgggacc actgtcggca gaggcatctt   1140
gaatgatagc ctttccttta tcgcaatgat ggcatttgta ggagccacct tccttttcta   1200
ctgtcctttc gatgaagtga cagatagctg ggcaatggaa tccgaggagg tttcccgaaa   1260
ttatcctttg ttgaaaagtc tcaatagccc tttggtcttc tgagactgta tctttgacat   1320
ttttggagta gaccagagtg tcgtgctcca ccatgttgac gaagattttc ttcttgtcat   1380
tgagtcgtaa aagactctgt atgaactgtt cgccagtctt cacggcgagt tctgttagat   1440
cctcgatttg aatcttagac tccatgcatg gccttagatt cagtaggaac taccttttta   1500
gagactccaa tctctattac ttgccttggt ttatgaagca agccttgaat cgtccatact   1560
ggaatagtac ttctgatctt gagaaatatg tctttctctg tgttcttgat gcaattagtc   1620
ctgaatcttt tgactgcatc tttaaccttc ttgggaaggt atttgatctc ctggagattg   1680
ttactcgggt agatcgtctt gatgagacct gctgcgtagg aacgcggccg ctgtacaggg   1740
cccgggcata tggcgcgtta gggataacag ggtaattacg tattaattaa ggcgcgtcct   1800
gcaggtcact ggattttggt tttaggaatt agaaatttta ttgatagaag tattttacaa   1860
atacaaatac atactaaggg tttcttatat gctcaacaca tgagcgaaac cctataagaa   1920
ccctaattcc cttatctggg aactactcac acattattct ggagaaaaat agagagagat   1980
agatttgtag agagagactg gtgatttttg cgccgggtac cgagctcggt agcaattccc   2040
gaggctgtag ccgacgatgg tgcgccagga gagttgttga ttcattgttt gcctccctgc   2100
tgcggttttt caccgaagtt catgccagtc cagcgttttt gcagcagaaa agccgccgac   2160
ttcggtttgc ggtcgcgagt gaagatccct ttcttgttac cgccaacgcg caatatgcct   2220
tgcgaggtcg caaaatcggc gaaattccat acctgttcac cgacgacggc gctgacgcga   2280
tcaaagacgc ggtgatacat atccagccat gcacactgat actcttcact ccacatgtcg   2340
gtgtacattg agtgcagccc ggctaacgta tccacgccgt attcggtgat gataatcggc   2400
tgatgcagtt tctcctgcca ggccagaagt tctttttcca gtaccttctc tgccgtttcc   2460
aaatcgccgc tttggacata ccatccgtaa taacggttca ggcacagcac atcaaagaga   2520
tcgctgatgg tatcggtgtg agcgtcgcag aacattacat tgacgcaggt gatcggacgc   2580
gtcgggtcga gtttacgcgt tgcttccgcc agtggcgcga aatattcccg tgcaccttgc   2640
ggacgggtat ccggttcgtt ggcaatactc cacatcacca cgcttgggtg gtttttgtca   2700
cgcgctatca gctctttaat cgcctgtaag tgcgcttgct gagtttcccc gttgactgcc   2760
tcttcgctgt acagttcttt cggcttgttg cccgcttcga aaccaatgcc taaagagagg   2820
ttaaagccga cagcagcagt ttcatcaatc accacgatgc catgttcatc tgcccagtcg   2880
agcatctctt cagcgtaagg gtaatgcgag gtacggtagg agttggcccc aatccagtcc   2940
attaatgcgt ggtcgtgcac catcagcacg ttatcgaatc ctttgccacg caagtccgca   3000
tcttcatgac gaccaaagcc agtaaagtag aacggtttgt ggttaatcag gaactgttcg   3060
cccttcactg ccactgaccg gatgccgacg cgaagcgggt agatatcaca ctctgtctgg   3120
cttttggctg tgacgcacag ttcatagaga taaccttcac ccggttgcca gaggtgcgga   3180
ttcaccactt gcaaagtccc gctagtgcct tgtccagttg caaccacctg ttgatccgca   3240
```

```
tcacgcagtt caacgctgac atcaccattg gccaccacct gccagtcaac agacgcgtgg   3300
ttacagtctt gcgcgacatg cgtcaccacg gtgatatcgt ccacccaggt gttcggcgtg   3360
gtgtagagca ttacgctgcg atggattccg gcatagttaa agaaatcatg gaagtaagac   3420
tgctttttct tgccgttttc gtcggtaatc accattcccg gcgggatagt ctgccagttc   3480
agttcgttgt tcacacaaac ggtgatacct gcacatcaac aaattttggt catatattag   3540
aaaagttata aattaaaata tacacactta taaactacag aaaagcaatt gctatatact   3600
acattctttt attttgaaaa aaatatttga aatattatat tactactaat taatgataat   3660
tattatatat atatcaaagg tagaagcaga aacttacgta cacttttccc ggcaataaca   3720
tacggcgtga catcggcttc aaatggcgta tagccgccct gatgctccat cacttcctga   3780
ttattgaccc acactttgcc gtaatgagtg accgcatcga aacgcagcac gatacgctgg   3840
cctgcccaac ctttcggtat aaagacttcg cgctgatacc agacgttgcc cgcataatta   3900
cgaatatctg catcggcgaa ctgatcgtta aaactgcctg gcacagcaat tgcccggctt   3960
tcttgtaacg cgctttccca ccaacgctga tcaattccac agttttcgcg atccagactg   4020
aatgcccaca ggccgtcgag ttttttgatt tcacgggttg ggtttctac aggacggacc   4080
atggttgcaa ttacacacaa aaaaaaaagg aaaaaaagac gtttccttca aaatccaacc   4140
gaaatatata caaaaacaga ggaaaggttt ttaataattc atcatgaact cgatctctaa   4200
tacattgctt tttcttgagt aacaaaggta gagagaggaa gtaaaatgtt aaagttgatg   4260
tggaaggaga gagagaagag taccttaagt agaggactga gacagacgga ggccttttcg   4320
gcctatgatc tgaacagagc cgtgacgtat gggggatgta caagattata tctataaatt   4380
ttgtccatac tttatcctct tctgcaatgg atcacacgta atgttcttgt ctttttcatg   4440
aggtggctct ctcatctgat tttttattta ttataccaaa tcatgggtga tactctaaat   4500
aagtcctaaa ctttaaaaca ttttaaacaa gtccctatat tatcatattg ctccaatcag   4560
gtcctttcct ttgtaatttt ttaacttttt cgtcttatga gtatttataa catgtgttat   4620
atttaggcat aataattttt tttaccctcc gcggccgcag aattcgagct cgagttaagg   4680
cgcgccgttg caggtcgacg gccgagtact ggcaggatat ataccgttgt aatt         4734
```

<210> SEQ ID NO 9
<211> LENGTH: 5177
<212> TYPE: DNA
<213> ORGANISM: Artificial Sequence
<220> FEATURE:
<223> OTHER INFORMATION: T-DNA Pbtg-26GhA10::GUS

<400> SEQUENCE: 9

```
cggcaggata tattcaattg taaatggctc catggcgatc gctctagagg atctgcgatc     60
tagtaacata gatgacaccg cgcgcgataa tttatcctag tttgcgcgct atattttgtt    120
ttctatcgcg tattaaatgt ataattgcgg gactctaatc ataaaaaccc atctcataaa    180
taacgtcatg cattacatgt taattattac atgcttaacg taattcaaca gaaattatat    240
gataatcatc gcaagaccgg caacaggatt caatcttaag aaactttatt gccaaatgtt    300
tgaacgatct gcttcggatc ctagaacgcg tgatctcaga tctcggtgac gggcaggacc    360
ggacggggcg gtaccggcag gctgaagtcc agctgccaga aacccacgtc atgccagttc    420
ccgtgcttga agccggccgc ccgcagcatg ccgcgggggg catatccgag cgcctcgtgc    480
atgcgcacgc tcgggtcgtt gggcagcccg atgacagcga ccacgctctt gaagccctgt    540
```

-continued

```
gcctccaggg acttcagcag gtgggtgtag agcgtggagc ccagtcccgt ccgctggtgg     600
cggggggaga cgtacacggt cgactcggcc gtccagtcgt aggcgttgcg tgccttccag     660
gggcccgcgt aggcgatgcc ggcgacctcg ccgtccacct cggcgacgag ccagggatag     720
cgctcccgca gacggacgag gtcgtccgtc cactcctgcg gttcctgcgg ctcggtacgg     780
aagttgaccg tgcttgtctc gatgtagtgg ttgacgatgg tgcagaccgc cggcatgtcc     840
gcctcggtgg cacggcggat gtcggccggg cgtcgttctg ggtccatggt tatagagaga     900
gagatagatt tatagagaga gactggtgat ttcagcgtgt cctctccaaa tgaaatgaac     960
ttccttatat agaggaaggg tcttgcgaag gatagtggga ttgtgcgtca tcccttacgt    1020
cagtggagat gtcacatcaa tccacttgct ttgaagacgt ggttggaacg tcttcttttt    1080
ccacgatgct cctcgtgggt gggggtccat ctttgggacc actgtcggca gaggcatctt    1140
gaatgatagc ctttccttta tcgcaatgat ggcatttgta ggagccacct tccttttcta    1200
ctgtcctttc gatgaagtga cagatagctg ggcaatggaa tccgaggagg tttcccgaaa    1260
ttatcctttg ttgaaaagtc tcaatagccc tttggtcttc tgagactgta tctttgacat    1320
ttttggagta gaccagagtg tcgtgctcca ccatgttgac gaagattttc ttcttgtcat    1380
tgagtcgtaa aagactctgt atgaactgtt cgccagtctt cacggcgagt tctgttagat    1440
cctcgatttg aatcttagac tccatgcatg gccttagatt cagtaggaac taccttttta    1500
gagactccaa tctctattac ttgccttggt ttatgaagca agccttgaat cgtccatact    1560
ggaatagtac ttctgatctt gagaaatatg tctttctctg tgttcttgat gcaattagtc    1620
ctgaatcttt tgactgcatc tttaaccttc ttgggaaggt atttgatctc ctggagattg    1680
ttactcgggt agatcgtctt gatgagacct gctgcgtagg aacgcggccg ctgtacaggg    1740
cccgggcata tggcgcgtta gggataacag ggtaattacg tattaattaa ggcgcgtcct    1800
gcaggtcact ggattttggt tttaggaatt agaaatttta ttgatagaag tattttacaa    1860
atacaaatac atactaaggg tttcttatat gctcaacaca tgagcgaaac cctataagaa    1920
ccctaattcc cttatctggg aactactcac acattattct ggagaaaaat agagagagat    1980
agatttgtag agagagactg gtgatttttg cgccgggtac cgagctcggt agcaattccc    2040
gaggctgtag ccgacgatgg tgcgccagga gagttgttga ttcattgttt gcctccctgc    2100
tgcggttttt caccgaagtt catgccagtc cagcgttttt gcagcagaaa agccgccgac    2160
ttcggtttgc ggtcgcgagt gaagatccct ttcttgttac cgccaacgcg caatatgcct    2220
tgcgaggtcg caaaatcggc gaaattccat acctgttcac cgacgacggc gctgacgcga    2280
tcaaagacgc ggtgatacat atccagccat gcacactgat actcttcact ccacatgtcg    2340
gtgtacattg agtgcagccc ggctaacgta tccacgccgt attcggtgat gataatcggc    2400
tgatgcagtt tctcctgcca ggccagaagt tctttttcca gtaccttctc tgccgtttcc    2460
aaatcgccgc tttggacata ccatccgtaa taacggttca ggcacagcac atcaaagaga    2520
tcgctgatgg tatcggtgtg agcgtcgcag aacattacat tgacgcaggt gatcggacgc    2580
gtcgggtcga gtttacgcgt tgcttccgcc agtggcgcga aatattcccg tgcaccttgc    2640
ggacgggtat ccggttcgtt ggcaatactc cacatcacca cgcttgggtg gtttttgtca    2700
cgcgctatca gctctttaat cgcctgtaag tgcgcttgct gagtttcccc gttgactgcc    2760
tcttcgctgt acagttcttt cggcttgttg cccgcttcga aaccaatgcc taaagagagg    2820
ttaaagccga cagcagcagt ttcatcaatc accacgatgc catgttcatc tgcccagtcg    2880
agcatctctt cagcgtaagg gtaatgcgag gtacggtagg agttggcccc aatccagtcc    2940
```

-continued

```
attaatgcgt ggtcgtgcac catcagcacg ttatcgaatc ctttgccacg caagtccgca   3000
tcttcatgac gaccaaagcc agtaaagtag aacggtttgt ggttaatcag gaactgttcg   3060
cccttcactg ccactgaccg gatgccgacg cgaagcgggt agatatcaca ctctgtctgg   3120
cttttggctg tgacgcacag ttcatagaga taaccttcac ccggttgcca gaggtgcgga   3180
ttcaccactt gcaaagtccc gctagtgcct tgtccagttg caaccacctg ttgatccgca   3240
tcacgcagtt caacgctgac atcaccattg gccaccacct gccagtcaac agacgcgtgg   3300
ttacagtctt gcgcgacatg cgtcaccacg gtgatatcgt ccacccaggt gttcggcgtg   3360
gtgtagagca ttacgctgcg atggattccg gcatagttaa agaaatcatg gaagtaagac   3420
tgctttttct tgccgttttc gtcggtaatc accattcccg gcgggatagt ctgccagttc   3480
agttcgttgt tcacacaaac ggtgatacct gcacatcaac aaattttggt catatattag   3540
aaaagttata aattaaaata tacacactta taaactacag aaaagcaatt gctatatact   3600
acattctttt attttgaaaa aaatatttga aatattatat tactactaat taatgataat   3660
tattatatat atatcaaagg tagaagcaga aacttacgta cacttttccc ggcaataaca   3720
tacggcgtga catcggcttc aaatggcgta tagccgccct gatgctccat cacttcctga   3780
ttattgaccc acactttgcc gtaatgagtg accgcatcga aacgcagcac gatacgctgg   3840
cctgcccaac ctttcggtat aaagacttcg cgctgatacc agacgttgcc cgcataatta   3900
cgaatatctg catcggcgaa ctgatcgtta aaactgcctg gcacagcaat tgcccggctt   3960
tcttgtaacg cgctttccca ccaacgctga tcaattccac agttttcgcg atccagactg   4020
aatgcccaca ggccgtcgag tttttgatt tcacgggttg ggtttctac aggacggacc   4080
atggttgcaa ttacacacaa aaaaaaaagg aaaaaaagac gtttccttca aaatccaacc   4140
gaaatatata caaaaacaga ggaaaggttt ttaataattc atcatgaact cgatctctaa   4200
tacattgctt tttcttgagt aacaaaggta gagagaggaa gtaaaatgtt aaagttgatg   4260
tggaaggaga gagagaagag taccttaagt agaggactga gacagacgga ggccttttcg   4320
gcctatgatc tgaacagagc cgtgacgtat gggggatgta caagattata tctataaatt   4380
ttgtccatac tttatcctct tctgcaatgg atcacacgta atgttcttgt ctttttcatg   4440
aggtggctct ctcatctgat tttttattta ttataccaaa tcatgggtga tactctaaat   4500
aagtcctaaa ctttaaaaca ttttaaacaa gtccctatat tatcatattg ctccaatcag   4560
gtcctttcct ttgtaatttt ttaacttttt cgtcttatga gtatttataa catgtgttat   4620
atttaggcat aataattttt tttaccctcc aattttataa aagaattatt ttagtttttc   4680
atttaatttt tcgcctattt tactattatg aaattagacc gattacctgg gatatgaatg   4740
cattatctcg aaacttctta acatatcgtt ttaacttcat aaccagagga ggaaataccg   4800
tcgcgcatgc aatggcgaaa gaagggatga aaagcttaga agattgtttc taggtagaag   4860
atgcacattt aagagccata gatttaacag catcggacct tcaactcatg caatcaactc   4920
atgcaactgc catgagtttc tacatattag gtcctactct ttggatggag gatttcatct   4980
atccattcaa agataacctc aatctcccct cctgtcacat tcttcacgat tgttttggtc   5040
aggaagggtt tggccatttg gtatcaccaa taatctgaag tgcttttttt ggatgcggcc   5100
gcgaattcga gctcgagtta aggcgcgccg ttgcaggtcg acggccgagt actggcagga   5160
tatataccgt tgtaatt                                                  5177
```

<210> SEQ ID NO 10

-continued

<211> LENGTH: 4737
<212> TYPE: DNA
<213> ORGANISM: Artificial Sequence
<220> FEATURE:
<223> OTHER INFORMATION: T-DNA Pbtg-26GhD0.6::GUS

<400> SEQUENCE: 10
cggcaggata tattcaattg taaatggctc catggcgatc gctctagagg atctgcgatc 60
tagtaacata gatgacaccg cgcgcgataa tttatcctag tttgcgcgct atattttgtt 120
ttctatcgcg tattaaatgt ataattgcgg gactctaatc ataaaaaccc atctcataaa 180
taacgtcatg cattacatgt taattattac atgcttaacg taattcaaca gaaattatat 240
gataatcatc gcaagaccgg caacaggatt caatcttaag aaactttatt gccaaatgtt 300
tgaacgatct gcttcggatc ctagaacgcg tgatctcaga tctcggtgac gggcaggacc 360
ggacggggcg gtaccggcag gctgaagtcc agctgccaga aacccacgtc atgccagttc 420
ccgtgcttga agccggccgc ccgcagcatg ccgcgggggg catatccgag cgcctcgtgc 480
atgcgcacgc tcgggtcgtt gggcagcccg atgacagcga ccacgctctt gaagccctgt 540
gcctccaggg acttcagcag gtgggtgtag agcgtggagc ccagtcccgt ccgctggtgg 600
cggggggaga cgtacacggt cgactcggcc gtccagtcgt aggcgttgcg tgccttccag 660
gggcccgcgt aggcgatgcc ggcgacctcg ccgtccacct cggcgacgag ccagggatag 720
cgctcccgca gacggacgag gtcgtccgtc cactcctgcg gttcctgcgg ctcggtacgg 780
aagttgaccg tgcttgtctc gatgtagtgg ttgacgatgg tgcagaccgc cggcatgtcc 840
gcctcggtgg cacggcggat gtcggccggg cgtcgttctg ggtccatggt tatagagaga 900
gagatagatt tatagagaga gactggtgat ttcagcgtgt cctctccaaa tgaaatgaac 960
ttccttatat agaggaaggg tcttgcgaag gatagtggga ttgtgcgtca tcccttacgt 1020
cagtggagat gtcacatcaa tccacttgct ttgaagacgt ggttggaacg tcttcttttt 1080
ccacgatgct cctcgtgggt gggggtccat ctttgggacc actgtcggca gaggcatctt 1140
gaatgatagc ctttccttta tcgcaatgat ggcatttgta ggagccacct tccttttcta 1200
ctgtcctttc gatgaagtga cagatagctg ggcaatggaa tccgaggagg tttcccgaaa 1260
ttatcctttg ttgaaaagtc tcaatagccc tttggtcttc tgagactgta tctttgacat 1320
ttttggagta gaccagagtg tcgtgctcca ccatgttgac gaagattttc ttcttgtcat 1380
tgagtcgtaa aagactctgt atgaactgtt cgccagtctt cacggcgagt tctgttagat 1440
cctcgatttg aatcttagac tccatgcatg gccttagatt cagtaggaac taccttttta 1500
gagactccaa tctctattac ttgccttggt ttatgaagca agccttgaat cgtccatact 1560
ggaatagtac ttctgatctt gagaaatatg tctttctctg tgttcttgat gcaattagtc 1620
ctgaatcttt tgactgcatc tttaaccttc ttgggaaggt atttgatctc ctggagattg 1680
ttactcgggt agatcgtctt gatgagacct gctgcgtagg aacgcggccg ctgtacaggg 1740
cccgggcata tggcgcgtta gggataacag ggtaattacg tattaattaa ggcgcgtcct 1800
gcaggtcact ggattttggt tttaggaatt agaaatttta ttgatagaag tattttacaa 1860
atacaaatac atactaaggg tttcttatat gctcaacaca tgagcgaaac cctataagaa 1920
ccctaattcc cttatctggg aactactcac acattattct ggagaaaaat agagagagat 1980
agatttgtag agagagactg gtgatttttg cgccgggtac cgagctcggt agcaattccc 2040
gaggctgtag ccgacgatgg tgcgccagga gagttgttga ttcattgttt gcctccctgc 2100
tgcggttttt caccgaagtt catgccagtc cagcgttttt gcagcagaaa agccgccgac 2160

-continued

```
ttcggtttgc ggtcgcgagt gaagatccct ttcttgttac cgccaacgcg caatatgcct   2220
tgcgaggtcg caaaatcggc gaaattccat acctgttcac cgacgacggc gctgacgcga   2280
tcaaagacgc ggtgatacat atccagccat gcacactgat actcttcact ccacatgtcg   2340
gtgtacattg agtgcagccc ggctaacgta tccacgccgt attcggtgat gataatcggc   2400
tgatgcagtt tctcctgcca ggccagaagt tctttttcca gtaccttctc tgccgtttcc   2460
aaatcgccgc tttggacata ccatccgtaa taacggttca ggcacagcac atcaaagaga   2520
tcgctgatgg tatcggtgtg agcgtcgcag aacattacat tgacgcaggt gatcggacgc   2580
gtcgggtcga gtttacgcgt tgcttccgcc agtggcgcga aatattcccg tgcaccttgc   2640
ggacgggtat ccggttcgtt ggcaatactc cacatcacca cgcttgggtg gtttttgtca   2700
cgcgctatca gctctttaat cgcctgtaag tgcgcttgct gagtttcccc gttgactgcc   2760
tcttcgctgt acagttcttt cggcttgttg cccgcttcga aaccaatgcc taaagagagg   2820
ttaaagccga cagcagcagt ttcatcaatc accacgatgc catgttcatc tgcccagtcg   2880
agcatctctt cagcgtaagg gtaatgcgag gtacggtagg agttggcccc aatccagtcc   2940
attaatgcgt ggtcgtgcac catcagcacg ttatcgaatc ctttgccacg caagtccgca   3000
tcttcatgac gaccaaagcc agtaaagtag aacggtttgt ggttaatcag gaactgttcg   3060
cccttcactg ccactgaccg gatgccgacg cgaagcgggt agatatcaca ctctgtctgg   3120
cttttggctg tgacgcacag ttcatagaga taaccttcac ccggttgcca gaggtgcgga   3180
ttcaccactt gcaaagtccc gctagtgcct tgtccagttg caaccacctg ttgatccgca   3240
tcacgcagtt caacgctgac atcaccattg gccaccacct gccagtcaac agacgcgtgg   3300
ttacagtctt gcgcgacatg cgtcaccacg gtgatatcgt ccacccaggt gttcggcgtg   3360
gtgtagagca ttacgctgcg atggattccg gcatagttaa agaaatcatg gaagtaagac   3420
tgctttttct tgccgttttc gtcggtaatc accattcccg gcgggatagt ctgccagttc   3480
agttcgttgt tcacacaaac ggtgatacct gcacatcaac aaattttggt catatattag   3540
aaaagttata aattaaaata tacacactta taaactacag aaaagcaatt gctatatact   3600
acattctttt attttgaaaa aaatatttga aatattatat tactactaat taatgataat   3660
tattatatat atatcaaagg tagaagcaga aacttacgta cacttttccc ggcaataaca   3720
tacggcgtga catcggcttc aaatggcgta tagccgccct gatgctccat cacttcctga   3780
ttattgaccc acactttgcc gtaatgagtg accgcatcga aacgcagcac gatacgctgg   3840
cctgcccaac ctttcggtat aaagacttcg cgctgatacc agacgttgcc cgcataatta   3900
cgaatatctg catcggcgaa ctgatcgtta aaactgcctg gcacagcaat tgcccggctt   3960
tcttgtaacg cgctttccca ccaacgctga tcaattccac agttttcgcg atccagactg   4020
aatgcccaca ggccgtcgag tttttgatt tcacgggttg gggtttctac aggacggacc   4080
atggttgcaa ttgcacacac acacaaaaag ggaaaaaaaa gaagtttcct tcaaaatcca   4140
accaaaatat atacaaaaac agaggaaagg tttttaataa ttcatcatga actcgatctc   4200
tattaccttg ctttttcttg agtaccaaag gaagagagcg aaagtaatat gttgaagttg   4260
atgtcgaagg agagagagaa gagtacctta agtagaggac tgagacagac tgaggccttt   4320
tcggcctatg atctgaaaag agccgtgacg tatgggggat gtacaagatt atatttataa   4380
attttgtcca tactttatcc tcttctgcaa tggatcacac gtaatgttct tgtctttttc   4440
atgaggtggc tctctcatct gattttttat ttattatacc aaatcatggg tgatactcta   4500
```

aataagtcct aaactttaaa acattttaaa caagtcccta tattatcata ctgctccaat 4560
caggtccttt cctttgtaat tttttaactt tttcgtctta tgagtattta taacatgttt 4620
tatatttagg catgatgatt tttttgccct tcaagcggcc gcgaattcga gctcgagtta 4680
aggcgcgccg ttgcaggtcg acggccgagt actggcagga tatataccgt tgtaatt 4737

<210> SEQ ID NO 11
<211> LENGTH: 5187
<212> TYPE: DNA
<213> ORGANISM: Artificial Sequence
<220> FEATURE:
<223> OTHER INFORMATION: T-DNA Pbtg-26GhD10::GUS

<400> SEQUENCE: 11
cggcaggata tattcaattg taaatggctc catggcgatc gctctagagg atctgcgatc 60
tagtaacata gatgacaccg cgcgcgataa tttatcctag tttgcgcgct atattttgtt 120
ttctatcgcg tattaaatgt ataattgcgg gactctaatc ataaaaaccc atctcataaa 180
taacgtcatg cattacatgt taattattac atgcttaacg taattcaaca gaaattatat 240
gataatcatc gcaagaccgg caacaggatt caatcttaag aaactttatt gccaaatgtt 300
tgaacgatct gcttcggatc ctagaacgcg tgatctcaga tctcggtgac gggcaggacc 360
ggacggggcg gtaccggcag gctgaagtcc agctgccaga aacccacgtc atgccagttc 420
ccgtgcttga agccggccgc ccgcagcatg ccgcgggggg catatccgag cgcctcgtgc 480
atgcgcacgc tcgggtcgtt gggcagcccg atgacagcga ccacgctctt gaagccctgt 540
gcctccaggg acttcagcag gtgggtgtag agcgtggagc ccagtcccgt ccgctggtgg 600
cggggggaga cgtacacggt cgactcggcc gtccagtcgt aggcgttgcg tgccttccag 660
gggcccgcgt aggcgatgcc ggcgacctcg ccgtccacct cggcgacgag ccagggatag 720
cgctcccgca gacggacgag gtcgtccgtc cactcctgcg gttcctgcgg ctcggtacgg 780
aagttgaccg tgcttgtctc gatgtagtgg ttgacgatgg tgcagaccgc cggcatgtcc 840
gcctcggtgg cacggcggat gtcggccggg cgtcgttctg ggtccatggt tatagagaga 900
gagatagatt tatagagaga gactggtgat ttcagcgtgt cctctccaaa tgaaatgaac 960
ttccttatat agaggaaggg tcttgcgaag gatagtggga ttgtgcgtca tcccttacgt 1020
cagtggagat gtcacatcaa tccacttgct ttgaagacgt ggttggaacg tcttcttttt 1080
ccacgatgct cctcgtgggt gggggtccat ctttgggacc actgtcggca gaggcatctt 1140
gaatgatagc ctttccttta tcgcaatgat ggcatttgta ggagccacct tccttttcta 1200
ctgtcctttc gatgaagtga cagatagctg ggcaatggaa tccgaggagg tttcccgaaa 1260
ttatcctttg ttgaaaagtc tcaatagccc tttggtcttc tgagactgta tctttgacat 1320
ttttggagta gaccagagtg tcgtgctcca ccatgttgac gaagattttc ttcttgtcat 1380
tgagtcgtaa aagactctgt atgaactgtt cgccagtctt cacggcgagt tctgttagat 1440
cctcgatttg aatcttagac tccatgcatg gccttagatt cagtaggaac taccttttta 1500
gagactccaa tctctattac ttgccttggt ttatgaagca agccttgaat cgtccatact 1560
ggaatagtac ttctgatctt gagaaatatg tctttctctg tgttcttgat gcaattagtc 1620
ctgaatcttt tgactgcatc tttaaccttc ttgggaaggt atttgatctc ctggagattg 1680
ttactcgggt agatcgtctt gatgagacct gctgcgtagg aacgcggccg ctgtacaggg 1740
cccgggcata tggcgcgtta gggataacag ggtaattacg tattaattaa ggcgcgtcct 1800
gcaggtcact ggattttggt tttaggaatt agaaatttta ttgatagaag tattttacaa 1860

-continued

```
atacaaatac atactaaggg tttcttatat gctcaacaca tgagcgaaac cctataagaa   1920
ccctaattcc cttatctggg aactactcac acattattct ggagaaaaat agagagagat   1980
agatttgtag agagagactg gtgatttttg cgccgggtac cgagctcggt agcaattccc   2040
gaggctgtag ccgacgatgg tgcgccagga gagttgttga ttcattgttt gcctccctgc   2100
tgcggttttt caccgaagtt catgccagtc cagcgttttt gcagcagaaa agccgccgac   2160
ttcggtttgc ggtcgcgagt gaagatccct ttcttgttac cgccaacgcg caatatgcct   2220
tgcgaggtcg caaaatcggc gaaattccat acctgttcac cgacgacggc gctgacgcga   2280
tcaaagacgc ggtgatacat atccagccat gcacactgat actcttcact ccacatgtcg   2340
gtgtacattg agtgcagccc ggctaacgta tccacgccgt attcggtgat gataatcggc   2400
tgatgcagtt tctcctgcca ggccagaagt tctttttcca gtaccttctc tgccgtttcc   2460
aaatcgccgc tttggacata ccatccgtaa taacggttca ggcacagcac atcaaagaga   2520
tcgctgatgg tatcggtgtg agcgtcgcag aacattacat tgacgcaggt gatcggacgc   2580
gtcgggtcga gtttacgcgt tgcttccgcc agtggcgcga aatattcccg tgcaccttgc   2640
ggacgggtat ccggttcgtt ggcaatactc cacatcacca cgcttgggtg gtttttgtca   2700
cgcgctatca gctctttaat cgcctgtaag tgcgcttgct gagtttcccc gttgactgcc   2760
tcttcgctgt acagttcttt cggcttgttg cccgcttcga aaccaatgcc taaagagagg   2820
ttaaagccga cagcagcagt ttcatcaatc accacgatgc catgttcatc tgcccagtcg   2880
agcatctctt cagcgtaagg gtaatgcgag gtacggtagg agttggcccc aatccagtcc   2940
attaatgcgt ggtcgtgcac catcagcacg ttatcgaatc ctttgccacg caagtccgca   3000
tcttcatgac gaccaaagcc agtaaagtag aacggtttgt ggttaatcag gaactgttcg   3060
cccttcactg ccactgaccg gatgccgacg cgaagcgggt agatatcaca ctctgtctgg   3120
cttttggctg tgacgcacag ttcatagaga taaccttcac ccggttgcca gaggtgcgga   3180
ttcaccactt gcaaagtccc gctagtgcct tgtccagttg caaccacctg ttgatccgca   3240
tcacgcagtt caacgctgac atcaccattg gccaccacct gccagtcaac agacgcgtgg   3300
ttacagtctt gcgcgacatg cgtcaccacg gtgatatcgt ccacccaggt gttcggcgtg   3360
gtgtagagca ttacgctgcg atggattccg gcatagttaa agaaatcatg gaagtaagac   3420
tgctttttct tgccgttttc gtcggtaatc accattcccg gcgggatagt ctgccagttc   3480
agttcgttgt tcacacaaac ggtgatacct gcacatcaac aaattttggt catatattag   3540
aaaagttata aattaaaata tacacactta taaactacag aaaagcaatt gctatatact   3600
acattctttt attttgaaaa aaatatttga aatattatat tactactaat taatgataat   3660
tattatatat atatcaaagg tagaagcaga aacttacgta cacttttccc ggcaataaca   3720
tacggcgtga catcggcttc aaatggcgta tagccgccct gatgctccat cacttcctga   3780
ttattgaccc acactttgcc gtaatgagtg accgcatcga aacgcagcac gatacgctgg   3840
cctgcccaac ctttcggtat aaagacttcg cgctgatacc agacgttgcc cgcataatta   3900
cgaatatctg catcggcgaa ctgatcgtta aaactgcctg gcacagcaat tgcccggctt   3960
tcttgtaacg cgctttccca ccaacgctga tcaattccac agttttcgcg atccagactg   4020
aatgcccaca ggccgtcgag ttttttgatt tcacgggttg ggtttctac aggacggacc   4080
atggttgcaa ttgcacacac acacaaaaag ggaaaaaaaa gaagtttcct tcaaaatcca   4140
accaaaatat atacaaaaac agaggaaagg tttttaataa ttcatcatga actcgatctc   4200
```

-continued

```
tattaccttg ctttttcttg agtaccaaag gaagagagcg aaagtaatat gttgaagttg   4260

atgtcgaagg agagagagaa gagtacctta agtagaggac tgagacagac tgaggccttt   4320

tcggcctatg atctgaaaag agccgtgacg tatgggggat gtacaagatt atatttataa   4380

attttgtcca tactttatcc tcttctgcaa tggatcacac gtaatgttct tgtctttttc   4440

atgaggtggc tctctcatct gatttttttat ttattatacc aaatcatggg tgatactcta   4500

aataagtcct aaactttaaa acattttaaa caagtcccta tattatcata ctgctccaat   4560

caggtccttt cctttgtaat tttttaactt tttcgtctta tgagtattta taacatgttt   4620

tatatttagg catgatgatt tttttgccct tcaattttat aaaaaaaaatt attttagctt   4680

ttcatttaat tttttgcctc ttttactatt atgaaattat gtgaaagcat tatctcaaag   4740

cttcttagca ctattgtttt aaattcatag ctagaggagg aaacactgtc gcacatgcaa   4800

tggcgaaaga agggatgaaa agcttagacc tgtgacccaa gtcaataagt tacactggca   4860

tggacacggg ctaagacacg actgtctgta cctatttcga atgttgacac ggccatgtga   4920

cccctacaga ccaaattttt caactttttc ctaaattttc caaatgtttt cgattcagtc   4980

ccgaattgtt tctttaatat ttttagggcc tctagggctc aattaaggaa cattatggat   5040

gtatttgaat gaaatttgag tatgtttgta ttaatgtatg atttgaatgg tttttctatt   5100

ccatgcggcc gcgaattcga gctcgagtta aggcgcgccg ttgcaggtcg acggccgagt   5160

actggcagga tatataccgt tgtaatt                                        5187


<210> SEQ ID NO 12
<211> LENGTH: 954
<212> TYPE: DNA
<213> ORGANISM: Brassica juncea

<400> SEQUENCE: 12

atggcgactc ttaaggtttc ttcttctgtt ccttctccct ctgaagatgc tgagcaattg     60

aaaagcgcat ttgatggatg gggtaccaac gaggaattga tcatatcaat cttggctcac    120

agaagtgctg aacagaggaa gctgatcagg caaacatacc atgaatcctt tggagaggat    180

cttcttaaga gtcttgagaa ggaacttaca agcgacttcg agagagccat cttgctctgg    240

actcttgaac cgggtgaacg tgatgcctta ttggttaatg aagctaccaa aagatggact    300

tcaagcaacc aagtgcttat ggaagtagct tgcactagga cctctacgca gcttcttcac    360

gctaggcaag cttaccacgc tcgcttcaag aagtctattg aagaggatgt cgctcaccac    420

accaccggtg acttcagaaa gcttttggtt tctcttgtta gctcatacag gtacgaaggg    480

gaagaggtaa acatgacatt ggcaaagcaa gaggctaagc tgattcatga gaaaatcaag    540

gacaagcatt acaatgatga agatttcata aggattttgt ccacaaggag caaagcacag    600

atcaatgcta ccttcaatcg ctatcaagat aatcacggcg aggaaatcct caagagcctt    660

gaggaaggag atgaagacga caagttccta gggctgttga ggtcaaccat tcaatgcttg    720

acaagacctg agctttactt tgtggatgtt cttcgttcag cgatcaacaa aacgggaaca    780

gacgaaggag ctctcactag aattgtgacc acaagagctg agattgactt gaaagtcatt    840

ggacaagagt accaaagaag gaacagcatt ccattggaga aagccattac caaagacact    900

cgtggagatt acgagaagat gctcatcgca cttctcggtg aagatgatgc ttaa          954


<210> SEQ ID NO 13
<211> LENGTH: 317
<212> TYPE: PRT
<213> ORGANISM: Brassica juncea
```

<400> SEQUENCE: 13

```
Met Ala Thr Leu Lys Val Ser Ser Ser Val Pro Ser Pro Ser Glu Asp
1               5                   10                  15

Ala Glu Gln Leu Lys Ser Ala Phe Asp Gly Trp Gly Thr Asn Glu Glu
            20                  25                  30

Leu Ile Ile Ser Ile Leu Ala His Arg Ser Ala Glu Gln Arg Lys Leu
        35                  40                  45

Ile Arg Gln Thr Tyr His Glu Ser Phe Gly Glu Asp Leu Leu Lys Ser
    50                  55                  60

Leu Glu Lys Glu Leu Thr Ser Asp Phe Glu Arg Ala Ile Leu Leu Trp
65                  70                  75                  80

Thr Leu Glu Pro Gly Glu Arg Asp Ala Leu Leu Val Asn Glu Ala Thr
                85                  90                  95

Lys Arg Trp Thr Ser Ser Asn Gln Val Leu Met Glu Val Ala Cys Thr
            100                 105                 110

Arg Thr Ser Thr Gln Leu Leu His Ala Arg Gln Ala Tyr His Ala Arg
        115                 120                 125

Phe Lys Lys Ser Ile Glu Glu Asp Val Ala His His Thr Thr Gly Asp
    130                 135                 140

Phe Arg Lys Leu Leu Val Ser Leu Val Ser Ser Tyr Arg Tyr Glu Gly
145                 150                 155                 160

Glu Glu Val Asn Met Thr Leu Ala Lys Gln Glu Ala Lys Leu Ile His
                165                 170                 175

Glu Lys Ile Lys Asp Lys His Tyr Asn Asp Glu Asp Phe Ile Arg Ile
            180                 185                 190

Leu Ser Thr Arg Ser Lys Ala Gln Ile Asn Ala Thr Phe Asn Arg Tyr
        195                 200                 205

Gln Asp Asn His Gly Glu Glu Ile Leu Lys Ser Leu Glu Glu Gly Asp
    210                 215                 220

Glu Asp Asp Lys Phe Leu Gly Leu Leu Arg Ser Thr Ile Gln Cys Leu
225                 230                 235                 240

Thr Arg Pro Glu Leu Tyr Phe Val Asp Val Leu Arg Ser Ala Ile Asn
                245                 250                 255

Lys Thr Gly Thr Asp Glu Gly Ala Leu Thr Arg Ile Val Thr Thr Arg
            260                 265                 270

Ala Glu Ile Asp Leu Lys Val Ile Gly Gln Glu Tyr Gln Arg Arg Asn
        275                 280                 285

Ser Ile Pro Leu Glu Lys Ala Ile Thr Lys Asp Thr Arg Gly Asp Tyr
    290                 295                 300

Glu Lys Met Leu Ile Ala Leu Leu Gly Glu Asp Asp Ala
305                 310                 315
```

<210> SEQ ID NO 14
<211> LENGTH: 951
<212> TYPE: DNA
<213> ORGANISM: Gossypium hirsutum

<400> SEQUENCE: 14

```
atggccactc ttacagtgcc cacgacagtt ccttcagtgt ctgaagattg tgaacaacta      60

agaaaagcct tttcaggatg gggaactaat gagggcttaa tcatagatat attgggtcac     120

agaaatgcgg agcaacgaaa cttgattcga aaaacctacg ctgaaaccta tggagaggat     180

ctcctcaagg cactagacaa ggagctctcg aatgactttg agaggctggt tctgctttgg     240
```

-continued

```
gctcttgatc ctgctgaacg tgatgccctt ttggctaatg aagccaccaa aaggtggact    300

tcaagaaatc aagtccttat ggaaatagcc tgcacaaggt ctgccaacca actgcttcac    360

gcaaggcagg cttatcatgc tcgttataag aagtcgcttg aagaggacgt tgctcatcac    420

acgactgggg acttccgtaa gctcctccta cctctagtga gttcatacag atatgaggga    480

gaggaggtga acatgactct ggcaaaaaca gaggcgaagt tgcttcatga gaaaatttca    540

aacaaagctt acagtgatga cgatgtcata agggttttgg ctacaagaag caaggcacag    600

atcaatgcaa ctctgaatca ctacaaaaat gaatatggaa atgacataaa caaggacttg    660

aaggctgacc ctaaggatga gttccttgca ctactaaggt ccacagtgaa gtgcttggtc    720

tatccggaaa agtattttga gaaggttctt cgcctagcaa tcaatagacg aggaacggat    780

gaaggagctc ttacaagagt tgtttgcact agggctgagg ttgatctaaa gatcatagca    840

gatgagtatc agcgaaggaa cagtgtccca ctgactcgtg ccattgtcaa ggacactcat    900

ggagactatg aaaaattgct gctggtactt gcaggacatg tggagaattg a             951
```

<210> SEQ ID NO 15
<211> LENGTH: 316
<212> TYPE: PRT
<213> ORGANISM: Gossypium hirsutum

<400> SEQUENCE: 15

```
Met Ala Thr Leu Thr Val Pro Thr Thr Val Pro Ser Val Ser Glu Asp
1               5                   10                  15

Cys Glu Gln Leu Arg Lys Ala Phe Ser Gly Trp Gly Thr Asn Glu Gly
            20                  25                  30

Leu Ile Ile Asp Ile Leu Gly His Arg Asn Ala Glu Gln Arg Asn Leu
        35                  40                  45

Ile Arg Lys Thr Tyr Ala Glu Thr Tyr Gly Glu Asp Leu Leu Lys Ala
    50                  55                  60

Leu Asp Lys Glu Leu Ser Asn Asp Phe Glu Arg Leu Val Leu Leu Trp
65                  70                  75                  80

Ala Leu Asp Pro Ala Glu Arg Asp Ala Leu Leu Ala Asn Glu Ala Thr
                85                  90                  95

Lys Arg Trp Thr Ser Arg Asn Gln Val Leu Met Glu Ile Ala Cys Thr
            100                 105                 110

Arg Ser Ala Asn Gln Leu Leu His Ala Arg Gln Ala Tyr His Ala Arg
        115                 120                 125

Tyr Lys Lys Ser Leu Glu Glu Asp Val Ala His His Thr Thr Gly Asp
    130                 135                 140

Phe Arg Lys Leu Leu Leu Pro Leu Val Ser Ser Tyr Arg Tyr Glu Gly
145                 150                 155                 160

Glu Glu Val Asn Met Thr Leu Ala Lys Thr Glu Ala Lys Leu Leu His
                165                 170                 175

Glu Lys Ile Ser Asn Lys Ala Tyr Ser Asp Asp Asp Val Ile Arg Val
            180                 185                 190

Leu Ala Thr Arg Ser Lys Ala Gln Ile Asn Ala Thr Leu Asn His Tyr
        195                 200                 205

Lys Asn Glu Tyr Gly Asn Asp Ile Asn Lys Asp Leu Lys Ala Asp Pro
    210                 215                 220

Lys Asp Glu Phe Leu Ala Leu Leu Arg Ser Thr Val Lys Cys Leu Val
225                 230                 235                 240

Tyr Pro Glu Lys Tyr Phe Glu Lys Val Leu Arg Leu Ala Ile Asn Arg
                245                 250                 255
```

Arg Gly Thr Asp Glu Gly Ala Leu Thr Arg Val Val Cys Thr Arg Ala
260 265 270

Glu Val Asp Leu Lys Ile Ile Ala Asp Glu Tyr Gln Arg Arg Asn Ser
275 280 285

Val Pro Leu Thr Arg Ala Ile Val Lys Asp Thr His Gly Asp Tyr Glu
290 295 300

Lys Leu Leu Leu Val Leu Ala Gly His Val Glu Asn
305 310 315

<210> SEQ ID NO 16
<211> LENGTH: 954
<212> TYPE: DNA
<213> ORGANISM: Arabidopsis thaliana

<400> SEQUENCE: 16
atggcgactc ttaaggtttc tgattctgtt cctgctcctt ctgatgatgc tgagcaattg 60
agaaccgctt ttgaaggatg gggtacgaac gaggacttga tcatatcaat cttggctcac 120
agaagtgctg aacagaggaa agtcatcagg caagcatacc acgaaaccta cggcgaagac 180
cttctcaaga ctcttgacaa ggagctctct aacgatttcg agagagctat cttgttgtgg 240
actcttgaac ccggtgagcg tgatgcttta ttggctaatg aagctacaaa aagatggact 300
tcaagcaacc aagttcttat ggaagttgct tgcacaagga catcaacgca gctgcttcac 360
gctaggcaag cttaccatgc tcgctacaag aagtctcttg aagaggacgt tgctcaccac 420
actaccggtg acttcagaaa gcttttggtt tctcttgtta cctcatacag gtacgaagga 480
gatgaagtga acatgacatt ggctaagcaa gaagctaagc tggtccatga gaaaatcaag 540
gacaagcact acaatgatga ggatgttatt agaatcttgt ccacaagaag caaagctcag 600
atcaatgcta cttttaaccg ttaccaagat gatcatggcg aggaaattct caagagtctt 660
gaggaaggag atgatgatga caagttcctt gcacttttga ggtcaaccat tcagtgcttg 720
acaagaccag agctttactt tgtcgatgtt cttcgttcag caatcaacaa aactggaact 780
gatgaaggag cactcactag aattgtgacc acaagagctg agattgactt gaaggtcatt 840
ggagaggagt accagcgcag gaacagcatt cctttggaga aagctattac caaagacact 900
cgtggagatt acgagaagat gctcgtcgca cttctcggtg aagatgatgc ttaa 954

<210> SEQ ID NO 17
<211> LENGTH: 317
<212> TYPE: PRT
<213> ORGANISM: Arabidopsis thaliana

<400> SEQUENCE: 17

Met Ala Thr Leu Lys Val Ser Asp Ser Val Pro Ala Pro Ser Asp Asp
1 5 10 15

Ala Glu Gln Leu Arg Thr Ala Phe Glu Gly Trp Gly Thr Asn Glu Asp
20 25 30

Leu Ile Ile Ser Ile Leu Ala His Arg Ser Ala Glu Gln Arg Lys Val
35 40 45

Ile Arg Gln Ala Tyr His Glu Thr Tyr Gly Glu Asp Leu Leu Lys Thr
50 55 60

Leu Asp Lys Glu Leu Ser Asn Asp Phe Glu Arg Ala Ile Leu Leu Trp
65 70 75 80

Thr Leu Glu Pro Gly Glu Arg Asp Ala Leu Leu Ala Asn Glu Ala Thr
85 90 95

-continued

```
Lys Arg Trp Thr Ser Ser Asn Gln Val Leu Met Glu Val Ala Cys Thr
            100                 105                 110

Arg Thr Ser Thr Gln Leu Leu His Ala Arg Gln Ala Tyr His Ala Arg
        115                 120                 125

Tyr Lys Lys Ser Leu Glu Glu Asp Val Ala His His Thr Thr Gly Asp
    130                 135                 140

Phe Arg Lys Leu Leu Val Ser Leu Val Thr Ser Tyr Arg Tyr Glu Gly
145                 150                 155                 160

Asp Glu Val Asn Met Thr Leu Ala Lys Gln Glu Ala Lys Leu Val His
                165                 170                 175

Glu Lys Ile Lys Asp Lys His Tyr Asn Asp Glu Asp Val Ile Arg Ile
            180                 185                 190

Leu Ser Thr Arg Ser Lys Ala Gln Ile Asn Ala Thr Phe Asn Arg Tyr
        195                 200                 205

Gln Asp Asp His Gly Glu Glu Ile Leu Lys Ser Leu Glu Glu Gly Asp
    210                 215                 220

Asp Asp Asp Lys Phe Leu Ala Leu Leu Arg Ser Thr Ile Gln Cys Leu
225                 230                 235                 240

Thr Arg Pro Glu Leu Tyr Phe Val Asp Val Leu Arg Ser Ala Ile Asn
                245                 250                 255

Lys Thr Gly Thr Asp Glu Gly Ala Leu Thr Arg Ile Val Thr Thr Arg
            260                 265                 270

Ala Glu Ile Asp Leu Lys Val Ile Gly Glu Glu Tyr Gln Arg Arg Asn
        275                 280                 285

Ser Ile Pro Leu Glu Lys Ala Ile Thr Lys Asp Thr Arg Gly Asp Tyr
    290                 295                 300

Glu Lys Met Leu Val Ala Leu Leu Gly Glu Asp Asp Ala
305                 310                 315
```

<210> SEQ ID NO 18
<211> LENGTH: 6217
<212> TYPE: DNA
<213> ORGANISM: Artificial Sequence
<220> FEATURE:
<223> OTHER INFORMATION: T-DNA P35S::AnnBj1

<400> SEQUENCE: 18

```
aattacaacg gtatatatcc tgccagtact gggccccctc gagggcgatc gctacgtacc      60

tgcaggcccg ggttaattaa gcggccgcaa catggtggag cacgacactc tcgtctactc     120

caagaatatc aaagatacag tctcagaaga ccaaagggct attgagactt ttcaacaaag     180

ggtaatatcg ggaaacctcc tcggattcca ttgcccagct atctgtcact tcatcaaaag     240

gacagtagaa aaggaaggtg gcacctacaa atgccatcat tgcgataaag gaaaggctat     300

cgttcaagat gcccctgccg acagtggtcc caaagatgga cccccaccca cgaggagcat     360

cgtggaaaaa gaagacgttc caaccacgtc ttcaaagcaa gtggattgat gtgatatctc     420

cactgacgta agggatgacg cacaatccca ctatccttcg caagaccctt cctctatata     480

aggaagttca tttcatttgg agaggactcg agctcatttc tctattactt cagccataac     540

aaaagaactc ttttctcttc ttattaaacc aaaaccatgg cgactcttaa ggtttcttct     600

tctgttcctt ctccctctga agatgctgag caattgaaaa gcgcatttga tggatggggt     660

accaacgagg aattgatcat atcaatcttg gctcacagaa gtgctgaaca gaggaagctg     720

atcaggcaaa cataccatga atcctttgga gaggatcttc ttaagagtct tgagaaggaa     780

cttacaagcg acttcgagag agccatcttg ctctggactc ttgaaccggg tgaacgtgat     840
```

gccttattgg ttaatgaagc taccaaaaga tggacttcaa gcaaccaagt gcttatggaa 900
gtagcttgca ctaggacctc tacgcagctt cttcacgcta ggcaagctta ccacgctcgc 960
ttcaagaagt ctattgaaga ggatgtcgct caccacacca ccggtgactt cagaaagctt 1020
ttggtttctc ttgttagctc atacaggtac gaaggggaag aggtaaacat gacattggca 1080
aagcaagagg ctaagctgat tcatgagaaa atcaaggaca agcattacaa tgatgaagat 1140
ttcataagga ttttgtccac aaggagcaaa gcacagatca atgctacctt caatcgctat 1200
caagataatc acggcgagga aatcctcaag agccttgagg aaggagatga agacgacaag 1260
ttcctagggc tgttgaggtc aaccattcaa tgcttgacaa gacctgagct ttactttgtg 1320
gatgttcttc gttcagcgat caacaaaacg ggaacagacg aaggagctct cactagaatt 1380
gtgaccacaa gagctgagat tgacttgaaa gtcattggac aagagtacca aagaaggaac 1440
agcattccat tggagaaagc cattaccaaa gacactcgtg gagattacga gaagatgctc 1500
atcgcacttc tcggtgaaga tgatgcttaa ggcgcgcccc cgatccgcgt ttgtgttttc 1560
tgggtttctc acttaagcgt ctgcgtttta cttttgtatt gggtttggcg tttagtagtt 1620
tgcggtagcg ttcttgttat gtgtaattac gctttttctt cttgcttcag cagtttcggt 1680
tgaaatataa atcgaatcaa gtttcacttt atcagcgttg ttttaaattt tggcattaaa 1740
ttggtgaaaa ttgcttcaat tttgtatcta aatagaagag acaacatgaa attcgacttt 1800
tgacctcaaa tcttcgaaca tttatttcct gatttcacga tggatgagga taacgaaagg 1860
gcggttccta tgtccgggaa agttcccgta gaagacaatg agcaaagcta ctgaaacgcg 1920
gacacgacgt cgcattggta cggatatgag ttaaaccgac tcaattcctt tattaagaca 1980
taaaccgatt ttggttaaag tgtaacagtg agctgatata aaaccgaaac aaaccggtac 2040
aagtttgatt gagcaacttg atgacaaact tcagaatttt ggttattgaa tgaaaatcat 2100
agtctaatcg taaaaaatgt acagaagaaa agctagagca gaacaaagat tctatattct 2160
ggttccaatt tatcatcgct ttaacgtccc tcagatttga tcggggaatt cgatatcatt 2220
accctgttat ccctaaagct tattaatgtt tgtcgaggag aaatatgagt cgaggcatgg 2280
atacactaag ttcccctgaa gtgagcatga tctttgatgc tgagatgatt cccagagcaa 2340
gatagtttgt gctgcaagtg acacaattgt aatgaaacca ccactcaacg aatttacttg 2400
tggctttgac atgtcgtgtg ctctgtttgt atttgtgagt gccggttggt aattattttt 2460
gttaatgtga ttttaaaacc tcttatgtaa atagttactt tatctattga agtgtgttct 2520
tgtggtctat agtttctcaa agggaaatta aaatgttgac atcccattta caattgataa 2580
cttggtatac acaaactttg taaatttggt gatatttatg gtcgaaagaa ggcaataccc 2640
attgtatgtt ccaatatcaa tatcaatacg ataacttgat aatactaaca tatgattgtc 2700
attgtttttc cagtatcaat atacattaag ctactacaaa attagtataa atcactatat 2760
tataaatctt tttcggttgt aacttgtaat tcgtgggttt ttaaaataaa agcatgtgaa 2820
aattttcaaa taatgtgatg gcgcaatttt attttccgag ttccaaaata ttgccgcttc 2880
attaccctaa tttgtggcgc cacatgtaaa acaaaagacg attcttagtg gctatcactg 2940
ccatcacgcg gatcactaat atgaaccgtc gattaaaaca gatcgacggt ttatacatca 3000
ttttattgta cacacggatc gatatctcag ccgttagatt taatatgcga tctgattgct 3060
caaaaaatag actctccgtc tttgcctata aaaacaattt cacatctttc tcacccaaat 3120
ctactcttaa ccgttcttct tcttctacag acatcaattt ctctcgactc tagaggatcc 3180

-continued aagcttatcg atttcgaacc cctcaggcga agaacaggta tgatttgttt gtaattagat 3240
caggggttta ggtctttcca ttacttttta atgtttttc tgttactgtc tccgcgatct 3300
gattttacga caatagagtt tcgggttttg tcccattcca gtttgaaaat aaaggtccgt 3360
cttttaagtt tgctggatcg ataaacctgt gaagattgag tctagtcgat ttattggatg 3420
atccattctt catcgttttt ttcttgcttc gaagttctgt ataaccagat ttgtctgtgt 3480
gcgattgtca ttacctagcc gtgtatcgag aactagggtt ttcgagtcaa ttttgcccct 3540
tttggttata tctggttcga taacgattca tctggattag ggttttaagt ggtgacgttt 3600
agtattccaa tttcttcaaa atttagttat ggataatgaa aatccccaat tgactgttca 3660
atttcttgtt aaatgcgcag atcacaatgg cttcgatctc ctcctcagtc gcgaccgtta 3720
gccggaccgc ccctgctcag gccaacatgg tggctccgtt caccggcctt aagtccaacg 3780
ccgccttccc caccaccaag aaggctaacg acttctccac ccttcccagc aacggtggaa 3840
gagttcaatg tatgcaggtg tggccggcct acggcaacaa gaagttcgag acgctgtcgt 3900
acctgccgcc gctgtctatg gcgcccaccg tgatgatggc ctcgtcggcc accgccgtcg 3960
ctccgttcca ggggctcaag tccaccgcca gcctccccgt cgcccgccgc tcctccagaa 4020
gcctcggcaa cgtcagcaac ggcggaagga tccggtgcat ggccggcgcc gaggagatcg 4080
tgctgcagcc catcaaggag atctccggca ccgtcaagct gccggggtcc aagtcgcttt 4140
ccaaccggat cctcctactc gccgccctgt ccgaggggac aacagtggtt gataacctgc 4200
tgaacagtga ggatgtccac tacatgctcg gggccttgag gactcttggt ctctctgtcg 4260
aagcggacaa agctgccaaa agagctgtag ttgttggctg tggtggaaag ttcccagttg 4320
aggatgctaa agaggaagtg cagctcttct tggggaatgc tggaatcgca atgcggtcct 4380
tgacagcagc tgttactgct gctggtggaa atgcaactta cgtgcttgat ggagtaccaa 4440
gaatgaggga gagacccatt ggcgacttgg ttgtcggatt gaagcagctt ggtgcagatg 4500
ttgattgttt ccttggcact gactgcccac ctgttcgtgt caatggaatc ggagggctac 4560
ctggtggcaa ggtcaagctg tctggctcca tcagcagtca gtacttgagt gccttgctga 4620
tggctgctcc tttggctctt ggggatgtgg agattgaaat cattgataaa ttaatctcca 4680
ttccgtacgt cgaaatgaca ttgagattga tggagcgttt tggtgtgaaa gcagagcatt 4740
ctgatagctg ggacagattc tacattaagg gaggtcaaaa atacaagtcc cctaaaaatg 4800
cctatgttga aggtgatgcc tcaagcgcaa gctatttctt ggctggtgct gcaattactg 4860
gagggactgt gactgtggaa ggttgtggca ccaccagttt gcagggtgat gtgaagtttg 4920
ctgaggtact ggagatgatg ggagcgaagg ttacatggac cgagactagc gtaactgtta 4980
ctggcccacc gcgggagcca tttgggagga aacacctcaa ggcgattgat gtcaacatga 5040
acaagatgcc tgatgtcgcc atgactcttg ctgtggttgc cctctttgcc gatggcccga 5100
cagccatcag agacgtggct tcctggagag taaaggagac cgagaggatg gttgcgatcc 5160
ggacggagct aaccaagctg ggagcatctg ttgaggaagg gccggactac tgcatcatca 5220
cgccgccgga gaagctgaac gtgacggcga tcgacacgta cgacgaccac aggatggcga 5280
tggctttctc ccttgccgcc tgtgccgagg tccccgtcac catccgggac cctgggtgca 5340
cccggaagac cttccccgac tacttcgatg tgctgagcac tttcgtcaag aattaagctc 5400
tagaactagt ggatcccccg atccgcgttt gtgttttctg ggtttctcac ttaagcgtct 5460
gcgttttact tttgtattgg gtttggcgtt tagtagtttg cggtagcgtt cttgttatgt 5520
gtaattacgc tttttcttct tgcttcagca gtttcggttg aaatataaat cgaatcaagt 5580

```
ttcactttat cagcgttgtt ttaaattttg gcattaaatt ggtgaaaatt gcttcaattt   5640

tgtatctaaa tagaagagac aacatgaaat tcgacttttg acctcaaatc ttcgaacatt   5700

tatttcctga tttcacgatg gatgaggata acgaaagggc ggttcctatg tccgggaaag   5760

ttcccgtaga agacaatgag caaagctact gaaacgcgga cacgacgtcg cattggtacg   5820

gatatgagtt aaaccgactc aattccttta ttaagacata aaccgatttt ggttaaagtg   5880

taacagtgag ctgatataaa accgaaacaa accggtacaa gtttgattga gcaacttgat   5940

gacaaacttc agaattttgg ttattgaatg aaaatcatag tctaatcgta aaaaatgtac   6000

agaagaaaag ctagagcaga acaaagattc tatattctgg ttccaattta tcatcgcttt   6060

aacgtccctc agatttgatc gggaaaccaa aacgtcgtga gacagtttgg ttaactataa   6120

cggtcctaag gtagcgatcg aggcattacg gcattacggc actcgcgagg gtccgaattc   6180

gagcatggag ccatttacaa ttgaatatat cctgccg                            6217
```

<210> SEQ ID NO 19
<211> LENGTH: 6751
<212> TYPE: DNA
<213> ORGANISM: Artificial Sequence
<220> FEATURE:
<223> OTHER INFORMATION: T-DNA Pbtg-26GhD10::AnnBj1

<400> SEQUENCE: 19

```
aattacaacg gtatatatcc tgccagtact gggccccctc gagggcgatc gctacgtacc     60

tgcaggcccg ggttaattaa gcggccgcat ggaatagaaa aaccattcaa atcatacatt    120

aatacaaaca tactcaaatt tcattcaaat acatccataa tgttccttaa ttgagcccta    180

gaggccctaa aaatattaaa gaaacaattc gggactgaat cgaaaacatt tggaaaattt    240

aggaaaaagt tgaaaaattt ggtctgtagg ggtcacatgg ccgtgtcaac attcgaaata    300

ggtacagaca gtcgtgtctt agcccgtgtc catgccagtg taacttattg acttgggtca    360

caggtctaag cttttcatcc cttctttcgc cattgcatgt gcgacagtgt ttcctcctct    420

agctatgaat ttaaaacaat agtgctaaga agctttgaga taatgctttc acataatttc    480

ataatagtaa aagaggcaaa aaattaaatg aaaagctaaa ataatttttt ttataaaatt    540

gaagggcaaa aaaatcatca tgcctaaata taaaacatgt tataaatact cataagacga    600

aaaagttaaa aaattacaaa ggaaaggacc tgattggagc agtatgataa tatagggact    660

tgtttaaaat gttttaaagt ttaggactta tttagagtat cacccatgat ttggtataat    720

aaataaaaaa tcagatgaga gagccacctc atgaaaaaga caagaacatt acgtgtgatc    780

cattgcagaa gaggataaag tatggacaaa atttataaat ataatcttgt acatccccca    840

tacgtcacgg ctcttttcag atcataggcc gaaaaggcct cagtctgtct cagtcctcta    900

cttaaggtac tcttctctct ctccttcgac atcaacttca acatattact ttcgctctct    960

tcctttggta ctcaagaaaa agcaaggtaa tagagatcga gttcatgatg aattattaaa   1020

aacctttcct ctgtttttgt atatattttg gttggatttt gaaggaaact tctttttttt   1080

cccttttttgt gtgtgtgtgc aattgcaacc atggcgactc ttaaggtttc ttcttctgtt  1140

ccttctccct ctgaagatgc tgagcaattg aaaagcgcat ttgatggatg gggtaccaac   1200

gaggaattga tcatatcaat cttggctcac agaagtgctg aacagaggaa gctgatcagg   1260

caaacatacc atgaatcctt tggagaggat cttcttaaga gtcttgagaa ggaacttaca   1320

agcgacttcg agagagccat cttgctctgg actcttgaac cgggtgaacg tgatgcctta   1380
```

-continued ttggttaatg aagctaccaa aagatggact tcaagcaacc aagtgcttat ggaagtagct 1440
tgcactagga cctctacgca gcttcttcac gctaggcaag cttaccacgc tcgcttcaag 1500
aagtctattg aagaggatgt cgctcaccac accaccggtg acttcagaaa gcttttggtt 1560
tctcttgtta gctcatacag gtacgaaggg gaagaggtaa acatgacatt ggcaaagcaa 1620
gaggctaagc tgattcatga gaaaatcaag gacaagcatt acaatgatga agatttcata 1680
aggattttgt ccacaaggag caaagcacag atcaatgcta ccttcaatcg ctatcaagat 1740
aatcacggcg aggaaatcct caagagcctt gaggaaggag atgaagacga caagttccta 1800
gggctgttga ggtcaaccat tcaatgcttg acaagacctg agctttactt tgtggatgtt 1860
cttcgttcag cgatcaacaa aacgggaaca gacgaaggag ctctcactag aattgtgacc 1920
acaagagctg agattgactt gaaagtcatt ggacaagagt accaaagaag gaacagcatt 1980
ccattggaga aagccattac caaagacact cgtggagatt acgagaagat gctcatcgca 2040
cttctcggtg aagatgatgc ttaaggcgcg cccccgatcc gcgtttgtgt tttctgggtt 2100
tctcacttaa gcgtctgcgt ttacttttg tattgggttt ggcgtttagt agtttgcggt 2160
agcgttcttg ttatgtgtaa ttacgctttt tcttcttgct tcagcagttt cggttgaaat 2220
ataaatcgaa tcaagtttca ctttatcagc gttgttttaa attttggcat taaattggtg 2280
aaaattgctt caattttgta tctaaataga agagacaaca tgaaattcga cttttgacct 2340
caaatcttcg aacatttatt tcctgatttc acgatggatg aggataacga aagggcggtt 2400
cctatgtccg ggaaagttcc cgtagaagac aatgagcaaa gctactgaaa cgcggacacg 2460
acgtcgcatt ggtacggata tgagttaaac cgactcaatt cctttattaa gacataaacc 2520
gattttggtt aaagtgtaac agtgagctga tataaaaccg aaacaaaccg gtacaagttt 2580
gattgagcaa cttgatgaca aacttcagaa ttttggttat tgaatgaaaa tcatagtcta 2640
atcgtaaaaa atgtacagaa gaaaagctag agcagaacaa agattctata ttctggttcc 2700
aatttatcat cgctttaacg tccctcagat ttgatcgggg aattcgatat cattaccctg 2760
ttatccctaa agcttattaa tgtttgtcga ggagaaatat gagtcgaggc atggatacac 2820
taagttcccc tgaagtgagc atgatctttg atgctgagat gattcccaga gcaagatagt 2880
ttgtgctgca agtgacacaa ttgtaatgaa accaccactc aacgaattta cttgtggctt 2940
tgacatgtcg tgtgctctgt ttgtatttgt gagtgccggt tggtaattat ttttgttaat 3000
gtgattttaa aacctcttat gtaaatagtt actttatcta ttgaagtgtg ttcttgtggt 3060
ctatagtttc tcaaagggaa attaaaatgt tgacatccca tttacaattg ataacttggt 3120
atacacaaac tttgtaaatt tggtgatatt tatggtcgaa agaaggcaat acccattgta 3180
tgttccaata tcaatatcaa tacgataact tgataatact aacatatgat tgtcattgtt 3240
tttccagtat caatatacat taagctacta caaaattagt ataaatcact atattataaa 3300
tctttttcgg ttgtaacttg taattcgtgg gtttttaaaa taaaagcatg tgaaaatttt 3360
caaataatgt gatggcgcaa ttttattttc cgagttccaa aatattgccg cttcattacc 3420
ctaatttgtg gcgccacatg taaaacaaaa gacgattctt agtggctatc actgccatca 3480
cgcggatcac taatatgaac cgtcgattaa aacagatcga cggtttatac atcattttat 3540
tgtacacacg gatcgatatc tcagccgtta gatttaatat gcgatctgat tgctcaaaaa 3600
atagactctc cgtctttgcc tataaaaaca atttcacatc tttctcaccc aaatctactc 3660
ttaaccgttc ttcttcttct acagacatca atttctctcg actctagagg atccaagctt 3720
atcgatttcg aacccctcag gcgaagaaca ggtatgattt gtttgtaatt agatcagggg 3780

-continued

```
tttaggtctt tccattactt tttaatgttt tttctgttac tgtctccgcg atctgatttt   3840
acgacaatag agtttcgggt tttgtcccat tccagtttga aaataaaggt ccgtctttta   3900
agtttgctgg atcgataaac ctgtgaagat tgagtctagt cgatttattg gatgatccat   3960
tcttcatcgt ttttttcttg cttcgaagtt ctgtataacc agatttgtct gtgtgcgatt   4020
gtcattacct agccgtgtat cgagaactag ggttttcgag tcaattttgc cccttttggt   4080
tatatctggt tcgataacga ttcatctgga ttagggtttt aagtggtgac gtttagtatt   4140
ccaatttctt caaaatttag ttatggataa tgaaaatccc caattgactg ttcaatttct   4200
tgttaaatgc gcagatcaca atggcttcga tctcctcctc agtcgcgacc gttagccgga   4260
ccgcccctgc tcaggccaac atggtggctc cgttcaccgg ccttaagtcc aacgccgcct   4320
tccccaccac caagaaggct aacgacttct ccacccttcc cagcaacggt ggaagagttc   4380
aatgtatgca ggtgtggccg gcctacggca acaagaagtt cgagacgctg tcgtacctgc   4440
cgccgctgtc tatggcgccc accgtgatga tggcctcgtc ggccaccgcc gtcgctccgt   4500
tccaggggct caagtccacc gccagcctcc ccgtcgcccg ccgctcctcc agaagcctcg   4560
gcaacgtcag caacggcgga aggatccggt gcatggccgg cgccgaggag atcgtgctgc   4620
agcccatcaa ggagatctcc ggcaccgtca agctgccggg gtccaagtcg ctttccaacc   4680
ggatcctcct actcgccgcc ctgtccgagg ggacaacagt ggttgataac ctgctgaaca   4740
gtgaggatgt ccactacatg ctcggggcct tgaggactct tggtctctct gtcgaagcgg   4800
acaaagctgc caaaagagct gtagttgttg gctgtggtgg aaagttccca gttgaggatg   4860
ctaaagagga agtgcagctc ttcttgggga atgctggaat cgcaatgcgg tccttgacag   4920
cagctgttac tgctgctggt ggaaatgcaa cttacgtgct tgatggagta ccaagaatga   4980
gggagagacc cattggcgac ttggttgtcg gattgaagca gcttggtgca gatgttgatt   5040
gtttccttgg cactgactgc ccacctgttc gtgtcaatgg aatcggaggg ctacctggtg   5100
gcaaggtcaa gctgtctggc tccatcagca gtcagtactt gagtgccttg ctgatggctg   5160
ctcctttggc tcttggggat gtggagattg aaatcattga taaattaatc tccattccgt   5220
acgtcgaaat gacattgaga ttgatggagc gttttggtgt gaaagcagag cattctgata   5280
gctgggacag attctacatt aagggaggtc aaaaatacaa gtcccctaaa aatgcctatg   5340
ttgaaggtga tgcctcaagc gcaagctatt tcttggctgg tgctgcaatt actggaggga   5400
ctgtgactgt ggaaggttgt ggcaccacca gtttgcaggg tgatgtgaag tttgctgagg   5460
tactggagat gatgggagcg aaggttacat ggaccgagac tagcgtaact gttactggcc   5520
caccgcggga gccatttggg aggaaacacc tcaaggcgat tgatgtcaac atgaacaaga   5580
tgcctgatgt cgccatgact cttgctgtgg ttgccctctt tgccgatggc ccgacagcca   5640
tcagagacgt ggcttcctgg agagtaaagg agaccgagag gatggttgcg atccggacgg   5700
agctaaccaa gctgggagca tctgttgagg aagggccgga ctactgcatc atcacgccgc   5760
cggagaagct gaacgtgacg gcgatcgaca cgtacgacga ccacaggatg gcgatggctt   5820
tctcccttgc cgcctgtgcc gaggtccccg tcaccatccg ggaccctggg tgcacccgga   5880
agaccttccc cgactacttc gatgtgctga gcactttcgt caagaattaa gctctagaac   5940
tagtggatcc cccgatccgc gtttgtgttt tctgggtttc tcacttaagc gtctgcgttt   6000
tacttttgta ttgggtttgg cgtttagtag tttgcggtag cgttcttgtt atgtgtaatt   6060
acgctttttc ttcttgcttc agcagtttcg gttgaaatat aaatcgaatc aagtttcact   6120
```

ttatcagcgt tgttttaaat tttggcatta aattggtgaa aattgcttca attttgtatc 6180
taaatagaag agacaacatg aaattcgact tttgacctca aatcttcgaa catttatttc 6240
ctgatttcac gatggatgag gataacgaaa gggcggttcc tatgtccggg aaagttcccg 6300
tagaagacaa tgagcaaagc tactgaaacg cggacacgac gtcgcattgg tacggatatg 6360
agttaaaccg actcaattcc tttattaaga cataaaccga ttttggttaa agtgtaacag 6420
tgagctgata taaaaccgaa acaaaccggt acaagtttga ttgagcaact tgatgacaaa 6480
cttcagaatt ttggttattg aatgaaaatc atagtctaat cgtaaaaaat gtacagaaga 6540
aaagctagag cagaacaaag attctatatt ctggttccaa tttatcatcg ctttaacgtc 6600
cctcagattt gatcgggaaa ccaaaacgtc gtgagacagt ttggttaact ataacggtcc 6660
taaggtagcg atcgaggcat tacggcatta cggcactcgc gagggtccga attcgagcat 6720
ggagccattt acaattgaat atatcctgcc g 6751

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
tgaccacaag agctgagatt g 21

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
ctccacgagt gtctttggta at 22

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
gatccttgtg gaggagtgga 20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
gcgaaacagt tcgacgagat 20

<210> SEQ ID NO 24
<211> LENGTH: 4323
<212> TYPE: DNA
<213> ORGANISM: Bacillus thuringiensis

<400> SEQUENCE: 24
atgacaacaa taaatgaatt atatccggct gtaccttata atgtactggc atatgctcca 60

-continued

```
ccacttaatt tagctgattc gacaccatgg ggtcaaatag ttgttgctga tgcaattaaa    120
gaagcttggg ataattttca aaaatatggt gtattagatt taacagctat aaatcaaggg    180
tttgatgatg caaatacagg ttcttttagt tatcaagctt taatacaaac tgttttgggt    240
attataggta caattggtat gacagttcct gtggctgctc catttgcagc tacagcgcct    300
attattagtt tatttgtagg attttttttgg cctaaaaaag ataagggacc acaattaatc    360
gatataattg ataaagaaat taaaaaatta ttagataagg aattaggaga gcaaaaacgt    420
aatgatttag ttagtgcttt aaatgagatg caagagggag caaatgagtt aagtgatatt    480
atgactaatg cactttttga aggtactata cagggaaatg ttgttactaa tgataaccct    540
caaggtaaaa ggcgaactcc taaagctcca acagttagtg attatgagaa tgtttattcg    600
gcatattttg tggaacatgt ggattttaga aacaaaatat ctacgtttct tactggttct    660
tatgatctta tagcactccc attatatgca ttagcaaaaa caatggagct ttcattgtat    720
caatcattta ttaattttgc taataaatgg atggattttg tatatacaaa agcaattaat    780
gaatcagcaa ctgatgatat gaaaagagat tatcaagcga gatacaatac tcaaaaaagt    840
aatttagctg tacaaaaaac acaattgatt aacaaaatta aagatggtac agatgctgtt    900
atgaaagttt ttaaagatac caataattta ccttcaatag gtactaataa attagcagta    960
aatgctcgta ataagtatat tagggcctta caaataaatt gtttagattt agttgctttg   1020
tggcctggct tatatccaga tgaatatctt ttaccattac aattagataa aacacgtgtt   1080
gtattttctg atacaatggg acctgatgaa acacatgatg gtcaaatgaa agttttaaat   1140
atattagact caactacaag ttataaccat caagatatag gaataagtac aactcaagat   1200
gtaaattctt tattatttta tccaagaaaa gaactgttag aattagattt tgctaaatat   1260
atttcatcta gtagtcgttt ttgggtttat ggatttggct taaaatattc agatgataac   1320
ttttatagat atggtgataa cgatccaagc agtgatttta aacctgcata taagtggttt   1380
acgaaaaatt cccagttcga aaaccttcct acttatggaa atcctactcc tattactaat   1440
ttaaatgcta aaactcaagt aacttcttat cttgatgcat taatatatta tatagacgga   1500
ggaactaatc tatataataa tgcgattctt catgatacag gggttatat tccgggatat   1560
ccaggtgtag aaggatatgg tatgagtaat aatgaacctt tagcaggaca aaaattaaat   1620
gctttatatc ctataaaagt ggaaaatgta agtggttcac aaggaaaatt aggaacaata   1680
gcagcttatg ttcctttaaa tttacaacca gaaaatatta ttggtgatgc tgatccgaat   1740
acaggttttc cccttaatgt aattaaagga tttccatttg aaaaatatgg acctgattat   1800
gagggacgag gaatttcggt tgtaaaagaa tggataaatg gtgcaaatgc tgtaaaattg   1860
tctccaggtc aatcagttgg ggtacaaatt aaaaatataa caaaacaaaa ttatcaaatt   1920
cgtactcgtt atgcaagtaa taacagtaat caagtatatt ttaatgtaga tccaggtgga   1980
tcaccattat ttgcacaatc agtaacattt gaatctacaa caaatgttac aagtggccaa   2040
caaggcgaaa atggtagata tacattaaaa actatttttt ctggtaatga tctacttaca   2100
gtagaaatcc ctgttggaaa tttttatgtg catgttacga ataaaggatc ttctgatatc   2160
tttttagatc gtcttgagtt ttctacagtt ccttcatatg ttatatattc aggtgattat   2220
gatgctacag gtacagatga tgtcttattg tcagatccac atgagtattt ttatgatgtc   2280
atagtgaatg gtactgctag tcattctagt gcagctactt ctatgaattt gctcaataaa   2340
ggaaccgtag taagaagcat tgatattcca ggtcactcaa cgtcttattc tgtacagtat   2400
```

-continued

```
tcagttccag aaggatttga tgaagttaga attctcagtt ctcttccgga tattagtgga   2460
actataagag tagaatctag taaaccacct gtatttaaga atgatggtaa tagtggtgat   2520
ggtggtaata ctgaatataa ttttaatttt gatttatcag gattgcaaga tactgggctt   2580
tattctggta aacttaaatc tggtattcgt gtgcaaggta attacactta cacaggtgct   2640
ccatctttaa atctggttgt ttacagaaat aatagtgttg tatccacttt tccagtaggt   2700
tctccttttg atatcactat aacaacagaa actgataagg ttatcctttc attacaacct   2760
caacatgggt tggcaacagt tactggtact ggcacaataa caattcctaa tgataaatta   2820
gcaattgttt atgataagtt atttaaatta ccacatgatt tagaaaatat aagaatacaa   2880
gtaaatgcat tattcatatc gagtacacaa aatgaattag ctaaagaagt aaatgaccat   2940
gatattgaag aagttgcatt gaaagtagat gcattatcgg atgaagtatt tggaaaagag   3000
aaaaaagaat tacgtaaact ggtcaatcaa gcgaaacgtt taagtaaagc acgaaacctt   3060
ctggtaggag gcaattttga taattgggaa gcttggtata aggaaaaaga agttgcaaga   3120
gtatctgatc atgaattatt gaagagtgat catgtattat taccgcctcc aactatgtat   3180
ccatcctata tatatcaaaa agtagaagaa acaaaattaa agccaaatac tcgttatatg   3240
atttctggtt tcatcgcaca tgcggaagat ttagaaattg tggtttctcg ttatgggcaa   3300
gaagtaagga aaatagtgca agttccatat ggagaagctt tcccattaac atccaatgga   3360
tcaatttgtt gtacaccaag ttttagacgt gatggaaaac tatcagatcc acatttcttt   3420
agttatagta ttgatgtagg tgaactggat atgacggcag gtccaggtat tgaattggga   3480
cttcgtattg tagatcgatt aggaatggcc cgtgtaagta atttagaaat tcgtgaagat   3540
cgttctttaa cagcaaatga aatacgaaaa gtgcaacgta tggcaagaaa ttggagaacc   3600
gaatatgaga aagaacgtgc agaagtaaca gcattaattg aacctgtatt aaaccaaatc   3660
aatgcgttat atgaaaatgg agattggaat ggttctattc gttcagatat ttcgtactac   3720
gatatagaat ctattgtatt accaacatta ccaagattac gtcattggtt tgttcctgat   3780
atgttaactg aacatggaaa tatcatgaat cgattcgaag aagcattaaa tcgtgcttat   3840
acacagctgg aaggaaatac actattgcat aacggtcatt ttacaacaga tgcggtaaat   3900
tggatgatac aaggagatgc acatcaggta atattagaag atggtagacg tgtattacga   3960
ttaccagact ggtcttcgag tgtatcccaa acaattgaaa tcgagaaatt tgatccagat   4020
aaagaataca acttagtatt tcatgcgcaa ggagaaggaa cggttacgtt ggagcatgga   4080
gaaaaaacaa aatatataga aacgcataca catcattttg cgaattttac aacatcacaa   4140
agtcaaggaa ttacgtttga atcgaataag gtgaccgtgg aaatttcttc agaagatggg   4200
gaattattgg tagatcatat cgcacttgtg gaagttccta tgtttaacaa gaatcaaatg   4260
gtcaatgaaa atagagatgt aaatataaat agcaatacaa atatgaataa tagcaataat   4320
caa                                                                 4323
```

```
<210> SEQ ID NO 25
<211> LENGTH: 1024
<212> TYPE: PRT
<213> ORGANISM: Bacillus thuringiensis

<400> SEQUENCE: 25

Met Thr Thr Ile Asn Glu Leu Tyr Pro Ala Val Pro Tyr Asn Val Leu
1               5                   10                  15

Ala Tyr Ala Pro Pro Leu Asn Leu Ala Asp Ser Thr Pro Trp Gly Gln
            20                  25                  30
```

-continued

```
Ile Val Val Ala Asp Ala Ile Lys Glu Ala Trp Asp Asn Phe Gln Lys
        35                  40                  45

Tyr Gly Val Leu Asp Leu Thr Ala Ile Asn Gln Gly Phe Asp Asp Ala
    50                  55                  60

Asn Thr Gly Ser Phe Ser Tyr Gln Ala Leu Ile Gln Thr Val Leu Gly
65                  70                  75                  80

Ile Ile Gly Thr Ile Gly Met Thr Val Pro Val Ala Ala Pro Phe Ala
                85                  90                  95

Ala Thr Ala Pro Ile Ile Ser Leu Phe Val Gly Phe Phe Trp Pro Lys
            100                 105                 110

Lys Asp Lys Gly Pro Gln Leu Ile Asp Ile Ile Asp Lys Glu Ile Lys
        115                 120                 125

Lys Leu Leu Asp Lys Glu Leu Gly Glu Gln Lys Arg Asn Asp Leu Val
    130                 135                 140

Ser Ala Leu Asn Glu Met Gln Glu Gly Ala Asn Glu Leu Ser Asp Ile
145                 150                 155                 160

Met Thr Asn Ala Leu Phe Glu Gly Thr Ile Gln Gly Asn Val Val Thr
                165                 170                 175

Asn Asp Asn Pro Gln Gly Lys Arg Arg Thr Pro Lys Ala Pro Thr Val
            180                 185                 190

Ser Asp Tyr Glu Asn Val Tyr Ser Ala Tyr Phe Val Glu His Val Asp
        195                 200                 205

Phe Arg Asn Lys Ile Ser Thr Phe Leu Thr Gly Ser Tyr Asp Leu Ile
    210                 215                 220

Ala Leu Pro Leu Tyr Ala Leu Ala Lys Thr Met Glu Leu Ser Leu Tyr
225                 230                 235                 240

Gln Ser Phe Ile Asn Phe Ala Asn Lys Trp Met Asp Phe Val Tyr Thr
                245                 250                 255

Lys Ala Ile Asn Glu Ser Ala Thr Asp Asp Met Lys Arg Asp Tyr Gln
            260                 265                 270

Ala Arg Tyr Asn Thr Gln Lys Ser Asn Leu Ala Val Gln Lys Thr Gln
        275                 280                 285

Leu Ile Asn Lys Ile Lys Asp Gly Thr Asp Ala Val Met Lys Val Phe
    290                 295                 300

Lys Asp Thr Asn Asn Leu Pro Ser Ile Gly Thr Asn Lys Leu Ala Val
305                 310                 315                 320

Asn Ala Arg Asn Lys Tyr Ile Arg Ala Leu Gln Ile Asn Cys Leu Asp
                325                 330                 335

Leu Val Ala Leu Trp Pro Gly Leu Tyr Pro Asp Glu Tyr Leu Leu Pro
            340                 345                 350

Leu Gln Leu Asp Lys Thr Arg Val Val Phe Ser Asp Thr Met Gly Pro
        355                 360                 365

Asp Glu Thr His Asp Gly Gln Met Lys Val Leu Asn Ile Leu Asp Ser
    370                 375                 380

Thr Thr Ser Tyr Asn His Gln Asp Ile Gly Ile Ser Thr Thr Gln Asp
385                 390                 395                 400

Val Asn Ser Leu Leu Phe Tyr Pro Arg Lys Glu Leu Leu Glu Leu Asp
                405                 410                 415

Phe Ala Lys Tyr Ile Ser Ser Ser Ser Arg Phe Trp Val Tyr Gly Phe
            420                 425                 430

Gly Leu Lys Tyr Ser Asp Asp Asn Phe Tyr Arg Tyr Gly Asp Asn Asp
        435                 440                 445
```

-continued

```
Pro Ser Ser Asp Phe Lys Pro Ala Tyr Lys Trp Phe Thr Lys Asn Ser
    450                 455                 460

Gln Phe Glu Asn Leu Pro Thr Tyr Gly Asn Pro Thr Pro Ile Thr Asn
465                 470                 475                 480

Leu Asn Ala Lys Thr Gln Val Thr Ser Tyr Leu Asp Ala Leu Ile Tyr
                485                 490                 495

Tyr Ile Asp Gly Gly Thr Asn Leu Tyr Asn Asn Ala Ile Leu His Asp
            500                 505                 510

Thr Gly Gly Tyr Ile Pro Gly Tyr Pro Gly Val Glu Gly Tyr Gly Met
        515                 520                 525

Ser Asn Asn Glu Pro Leu Ala Gly Gln Lys Leu Asn Ala Leu Tyr Pro
    530                 535                 540

Ile Lys Val Glu Asn Val Ser Gly Ser Gln Gly Lys Leu Gly Thr Ile
545                 550                 555                 560

Ala Ala Tyr Val Pro Leu Asn Leu Gln Pro Glu Asn Ile Ile Gly Asp
                565                 570                 575

Ala Asp Pro Asn Thr Gly Phe Pro Leu Asn Val Ile Lys Gly Phe Pro
            580                 585                 590

Phe Glu Lys Tyr Gly Pro Asp Tyr Glu Gly Arg Gly Ile Ser Val Val
        595                 600                 605

Lys Glu Trp Ile Asn Gly Ala Asn Ala Val Lys Leu Ser Pro Gly Gln
    610                 615                 620

Ser Val Gly Val Gln Ile Lys Asn Ile Thr Lys Gln Asn Tyr Gln Ile
625                 630                 635                 640

Arg Thr Arg Tyr Ala Ser Asn Asn Ser Asn Gln Val Tyr Phe Asn Val
                645                 650                 655

Asp Pro Gly Gly Ser Pro Leu Phe Ala Gln Ser Val Thr Phe Glu Ser
            660                 665                 670

Thr Thr Asn Val Thr Ser Gly Gln Gln Gly Glu Asn Gly Arg Tyr Thr
        675                 680                 685

Leu Lys Thr Ile Phe Ser Gly Asn Asp Leu Leu Thr Val Glu Ile Pro
    690                 695                 700

Val Gly Asn Phe Tyr Val His Val Thr Asn Lys Gly Ser Ser Asp Ile
705                 710                 715                 720

Phe Leu Asp Arg Leu Glu Phe Ser Thr Val Pro Ser Tyr Val Ile Tyr
                725                 730                 735

Ser Gly Asp Tyr Asp Ala Thr Gly Thr Asp Asp Val Leu Leu Ser Asp
            740                 745                 750

Pro His Glu Tyr Phe Tyr Asp Val Ile Val Asn Gly Thr Ala Ser His
        755                 760                 765

Ser Ser Ala Ala Thr Ser Met Asn Leu Leu Asn Lys Gly Thr Val Val
    770                 775                 780

Arg Ser Ile Asp Ile Pro Gly His Ser Thr Ser Tyr Ser Val Gln Tyr
785                 790                 795                 800

Ser Val Pro Glu Gly Phe Asp Glu Val Arg Ile Leu Ser Ser Leu Pro
                805                 810                 815

Asp Ile Ser Gly Thr Ile Arg Val Glu Ser Ser Lys Pro Pro Val Phe
            820                 825                 830

Lys Asn Asp Gly Asn Ser Gly Asp Gly Gly Asn Thr Glu Tyr Asn Phe
        835                 840                 845

Asn Phe Asp Leu Ser Gly Leu Gln Asp Thr Gly Leu Tyr Ser Gly Lys
    850                 855                 860

Leu Lys Ser Gly Ile Arg Val Gln Gly Asn Tyr Thr Tyr Thr Gly Ala
```

865 870 875 880

Pro Ser Leu Asn Leu Val Val Tyr Arg Asn Asn Ser Val Val Ser Thr
885 890 895

Phe Pro Val Gly Ser Pro Phe Asp Ile Thr Ile Thr Thr Glu Thr Asp
900 905 910

Lys Val Ile Leu Ser Leu Gln Pro Gln His Gly Leu Ala Thr Val Thr
915 920 925

Gly Thr Gly Thr Ile Thr Ile Pro Asn Asp Lys Leu Ala Ile Val Tyr
930 935 940

Asp Lys Leu Phe Lys Leu Pro His Asp Leu Glu Asn Ile Arg Ile Gln
945 950 955 960

Val Asn Ala Leu Phe Ile Ser Ser Thr Gln Asn Glu Leu Ala Lys Glu
965 970 975

Val Asn Asp His Asp Ile Glu Glu Val Ala Leu Lys Val Asp Ala Leu
980 985 990

Ser Asp Glu Val Phe Gly Lys Glu Lys Lys Glu Leu Arg Lys Leu Val
995 1000 1005

Asn Gln Ala Lys Arg Leu Ser Lys Ala Arg Asn Leu Leu Val Gly
1010 1015 1020

Gly

<210> SEQ ID NO 26
<211> LENGTH: 1024
<212> TYPE: DNA
<213> ORGANISM: Bacillus thuringiensis

<400> SEQUENCE: 26
atggattgta atttacaatc acaacaaaat attccatata atgtattagc aataccagta 60
tctaatgtta attcgttgac tgatacagtt ggagatttaa aaaaagcatg ggaagaattt 120
caaaaaactg gttctttttc attaacagct ttacaacaag gattttctgc ttcacaagga 180
ggaacattca attatttaac attactacaa tcaggaatat cattagctgg ttcttttgtt 240
cctggaggta cttttgtagc acctattatt aatatggtta ttggttggtt atggccacat 300
aaaaacaaaa atgcggatac agaaaattta ataaatttaa ttgattcaga aattcaaaaa 360
caattaaaca aagctttatt agatgcagat agaaatgagt ggagctctta tttagaatct 420
atatttgatt cttcaaataa cctaaatggt gcaattgtag atgcacagtg gtcaggcact 480
gtaaatacta caaatagaac actaagaaat ccaacagaat cagattatac aaatgttgtt 540
acaaatttta ttgcagcgga tggtgacatt gcaaataatg aaaatcacat aatgaatggc 600
aactttgacg tagctgcagc accttatttt gttataggag caacagcacg ttttgcagca 660
atgcaatctt atattaaatt ttgtaatgct tggattgata aagttggatt gagtgacgca 720
cagcttacta cacaaaaggc taatttagat cgcacgaaac aaaatatgcg taatgcaatt 780
cttaactata cacaacaagt tatgaaagtt tttaaagatt ccaaaaaatat gcctacaata 840 ggtactaata aatttagtgt tgatacctat aatgtatata ttaaaggaat gacattaaat 900
gttttagata ttgtagcaat atggccttca ttatatccag atgattatac ttcacaaaca 960
gccttagaac aaacacgtgt cactttttca aatatggttg gccaagaaga aggtacagat 1020
ggaa 1024

<210> SEQ ID NO 27
<211> LENGTH: 1024
<212> TYPE: PRT

<213> ORGANISM: Bacillus thuringiensis

<400> SEQUENCE: 27

Met Asp Cys Asn Leu Gln Ser Gln Gln Asn Ile Pro Tyr Asn Val Leu
1 5 10 15

Ala Ile Pro Val Ser Asn Val Asn Ser Leu Thr Asp Thr Val Gly Asp
20 25 30

Leu Lys Lys Ala Trp Glu Glu Phe Gln Lys Thr Gly Ser Phe Ser Leu
35 40 45

Thr Ala Leu Gln Gln Gly Phe Ser Ala Ser Gln Gly Gly Thr Phe Asn
50 55 60

Tyr Leu Thr Leu Leu Gln Ser Gly Ile Ser Leu Ala Gly Ser Phe Val
65 70 75 80

Pro Gly Gly Thr Phe Val Ala Pro Ile Ile Asn Met Val Ile Gly Trp
85 90 95

Leu Trp Pro His Lys Asn Lys Asn Ala Asp Thr Glu Asn Leu Ile Asn
100 105 110

Leu Ile Asp Ser Glu Ile Gln Lys Gln Leu Asn Lys Ala Leu Leu Asp
115 120 125

Ala Asp Arg Asn Glu Trp Ser Ser Tyr Leu Glu Ser Ile Phe Asp Ser
130 135 140

Ser Asn Asn Leu Asn Gly Ala Ile Val Asp Ala Gln Trp Ser Gly Thr
145 150 155 160

Val Asn Thr Thr Asn Arg Thr Leu Arg Asn Pro Thr Glu Ser Asp Tyr
165 170 175

Thr Asn Val Val Thr Asn Phe Ile Ala Ala Asp Gly Asp Ile Ala Asn
180 185 190

Asn Glu Asn His Ile Met Asn Gly Asn Phe Asp Val Ala Ala Ala Pro
195 200 205

Tyr Phe Val Ile Gly Ala Thr Ala Arg Phe Ala Ala Met Gln Ser Tyr
210 215 220

Ile Lys Phe Cys Asn Ala Trp Ile Asp Lys Val Gly Leu Ser Asp Ala
225 230 235 240

Gln Leu Thr Thr Gln Lys Ala Asn Leu Asp Arg Thr Lys Gln Asn Met
245 250 255

Arg Asn Ala Ile Leu Asn Tyr Thr Gln Gln Val Met Lys Val Phe Lys
260 265 270

Asp Ser Lys Asn Met Pro Thr Ile Gly Thr Asn Lys Phe Ser Val Asp
275 280 285

Thr Tyr Asn Val Tyr Ile Lys Gly Met Thr Leu Asn Val Leu Asp Ile
290 295 300

Val Ala Ile Trp Pro Ser Leu Tyr Pro Asp Asp Tyr Thr Ser Gln Thr
305 310 315 320

Ala Leu Glu Gln Thr Arg Val Thr Phe Ser Asn Met Val Gly Gln Glu
325 330 335

Glu Gly Thr Asp Gly Ser Leu Arg Ile Tyr Asn Thr Phe Asp Ser Phe
340 345 350

Ser Tyr Gln His Ser Pro Ile Pro Asn Asn Asn Val Asn Leu Ile Ser
355 360 365

Tyr Tyr Asn Asp Glu Leu Gln Asn Leu Glu Leu Gly Val Tyr Thr Pro
370 375 380

Pro Lys Lys Gly Ser Gly Tyr Ser Tyr Pro Tyr Gly Phe Val Leu Asn
385 390 395 400

Tyr Ala Asn Ser Lys Tyr Lys Tyr Gly Asp Ser Asn Asp Pro Glu Ser
405 410 415

Leu Gly Gly Leu Ser Thr Leu Ser Ala Pro Ile Gln Gln Val Asn Ala
420 425 430

Ala Thr Gln Asn Ser Lys Tyr Leu Asp Gly Glu Ile Leu Asn Gly Ile
435 440 445

Gly Ala Ser Leu Pro Gly Tyr Cys Thr Thr Gly Cys Ser Pro Thr Glu
450 455 460

Pro Pro Phe Ser Cys Thr Ser Thr Ala Asn Gly Tyr Lys Ala Ser Cys
465 470 475 480

Asn Pro Ser Asp Thr Asn Gln Lys Ile Asn Ala Leu Tyr Pro Phe Thr
485 490 495

Gln Ala Asn Val Lys Gly Asn Thr Gly Lys Leu Gly Val Leu Ala Ser
500 505 510

Leu Val Ser Tyr Asp Leu Asn Pro Lys Asn Val Phe Gly Glu Leu Asp
515 520 525

Ser Asp Thr Asn Asn Val Ile Leu Lys Gly Ile Pro Ala Glu Lys Gly
530 535 540

Tyr Phe Pro Asn Asn Ala Arg Pro Thr Val Val Lys Glu Trp Ile Asn
545 550 555 560

Gly Ala Ser Ala Val Pro Leu Asp Ser Gly Asn Thr Leu Phe Met Thr
565 570 575

Ala Thr Asn Leu Thr Ala Thr Gln Tyr Arg Ile Arg Ile Arg Tyr Ala
580 585 590

Asn Pro Asn Ser Asn Thr Gln Ile Gly Val Arg Ile Thr Gln Asn Gly
595 600 605

Ser Leu Ile Ser Ser Ser Asn Leu Thr Leu Tyr Ser Thr Thr Asp Met
610 615 620

Asn Asn Thr Leu Pro Leu Asn Val Tyr Val Ile Gly Glu Asn Gly Asn
625 630 635 640

Tyr Thr Leu Gln Asp Leu Tyr Asn Thr Thr Asn Val Leu Ser Thr Gly
645 650 655

Asp Ile Thr Leu Gln Ile Thr Gly Gly Asp Gln Lys Ile Phe Ile Asp
660 665 670

Arg Ile Glu Phe Val Pro Thr Met Pro Val Pro Gly Asn Thr Asn Asn
675 680 685

Asn Asn Gly Asn Asn Asn Gly Asn Asn Asn Pro Pro His His Val Cys
690 695 700

Ala Ile Ala Gly Thr Gln Gln Ser Cys Ser Gly Pro Pro Lys Phe Glu
705 710 715 720

Gln Val Ser Asp Leu Glu Lys Ile Thr Thr Gln Val Tyr Met Leu Phe
725 730 735

Lys Ser Ser Pro Tyr Glu Glu Leu Ala Leu Glu Val Ser Ser Tyr Gln
740 745 750

Ile Ser Gln Val Ala Leu Lys Val Met Ala Leu Ser Asp Glu Leu Phe
755 760 765

Cys Glu Glu Lys Asn Val Leu Arg Lys Leu Val Asn Lys Ala Lys Gln
770 775 780

Leu Leu Glu Ala Ser Asn Leu Leu Val Gly Gly Asn Phe Glu Thr Thr
785 790 795 800

Gln Asn Trp Val Leu Gly Thr Asn Ala Tyr Ile Asn Tyr Asp Ser Phe
805 810 815

Leu Phe Asn Gly Asn Tyr Leu Ser Leu Gln Pro Ala Ser Gly Phe Phe

```
            820                 825                 830

Thr Ser Tyr Ala Tyr Gln Lys Ile Asp Glu Ser Thr Leu Lys Pro Tyr
        835                 840                 845

Thr Arg Tyr Lys Val Ser Gly Phe Ile Gly Gln Ser Asn Gln Val Glu
    850                 855                 860

Leu Ile Ile Ser Arg Tyr Gly Lys Glu Ile Asp Lys Ile Leu Asn Val
865                 870                 875                 880

Pro Tyr Ala Gly Pro Leu Pro Ile Thr Ala Asp Ala Ser Ile Thr Cys
                885                 890                 895

Cys Ala Pro Glu Ile Gly Gln Cys Asp Gly Glu Gln Ser Asp Ser His
            900                 905                 910

Phe Phe Asn Tyr Ser Ile Asp Val Gly Ala Leu His Pro Glu Leu Asn
        915                 920                 925

Pro Gly Ile Glu Ile Gly Leu Lys Ile Val Gln Ser Asn Gly Tyr Ile
    930                 935                 940

Thr Ile Ser Asn Leu Glu Ile Ile Glu Glu Arg Pro Leu Thr Glu Met
945                 950                 955                 960

Glu Ile Gln Ala Val Asn Arg Lys Asn Gln Lys Trp Glu Arg Glu Lys
                965                 970                 975

Leu Leu Glu Cys Ala Ser Ile Ser Glu Leu Leu Gln Pro Ile Ile Asn
            980                 985                 990

Gln Ile Asp Ser Leu Phe Lys Asp  Gly Asn Trp Tyr Asn  Asp Ile Leu
        995                 1000                1005

Pro His  Val Thr Tyr Gln Asp  Leu Lys Asn Ile Ile  Ile Pro Glu
    1010                1015                1020

Leu


<210> SEQ ID NO 28
<211> LENGTH: 3549
<212> TYPE: DNA
<213> ORGANISM: Bacillus thuringiensis

<400> SEQUENCE: 28

atggattgta atttacgatc gcaacaaaat attccatata atgtattagc aacacaagca      60

tctaatctta gtcagtttac tgatatagct gaaggtgtaa aaaaagcatg ggcagaattt     120

caaaaaactg gatctttttc attagaagct ttaaaacaag gatttaatgc agcacaggga     180

ggaacattca attatttagc attactacaa tcaggaatat cattagctgg ttcttttgtc     240

cctggaggtt cttttgtagc acccattgtt aatatggtta ttggttggtt atggccaaat     300

aaaaacaaaa cagcggatac agaaaattta ataaaattaa ttgatgaaga aattcaaaaa     360

caattaaaca aagccttatt agaacaagac aaaaacaatt ggacctcttt tttagaaagt     420

atatttgatg tttcaaatac agtgaataat gcaattatag atgcacagtg gtcaggtact     480

gtagatgata caaatagaca actaaaaact ccaacaacat cagattataa aaatgttgtt     540

gaaaaatttg attcagcgga tactgcaatt ataactaatg aaaatcaaat aatgaacggc     600

aactttgacg tagctgcatc atcctatttt gttataggag caacattacg tcttgcatta     660

tttcaatctt atattaaatt ttgtaatcat tggattgata cagttggatt tgattcagat     720

aattataata cacaaaaggc taatttagct cgtacaaaac aaactatgcg tactacaatt     780

aatgattata cacaaaaaat tatgaaagtt tttaaaaatt ccgacaatat gcctacaatg     840

ggtactaata aatttagtgt tgatgcttat aatgcatata ttaaaggaat aacattaaat     900

gttttagata tagtatcaac gtggccctca ttatatccaa atgattatac ttcacaaaca     960
```

-continued

```
aagttagaac aaacacgtat catttttca aatatgattg gacaacaaga agctatagat   1020
ggaaccgtaa caatttacga tacttttgat tctgataatt ataaacataa accaatacct   1080
aataataatg ttaatttact ttcttatttt actgatgaat tacaaaatat acaactcgca   1140
ctatatacag ctcctcctaa acacaaaagt gatactcggg atagctatac gtatccttat   1200
ggatttattt taaattacca aaatagcaaa tataaatatg gcgataacga accagtgatt   1260
tcaaacacaa tatctgcacc tatacaacaa attaatgcag caactcaata cactcaatat   1320
atagatggag aaagtatcaa tggcattggc gcatatttac ctggttattg ttctacagat   1380
tgttcagaaa taactcctcc ttttgcttgc acttctaacg ataaaaataa gagctatgga   1440
gcaagctgta atagcgtata ttctagtcaa aaaatgaatg ctttatatcc ttttacacaa   1500
actaatgtac caggaaacca ggggaaatta ggagtactgg caagttatgt tccatatgat   1560
ttaaatccta aaaatatatt tggtgaagta gatccagata caaataatat tatcttaaaa   1620
ggaattcctg cagaaaaagg ctatttttct aattatacgc gacctactgt tgtaaaagaa   1680
tggattaatg gtgcaaatgc tgtatcactt tattcaggaa atactttatt tatagtcgct   1740
acgaatataa cagctactca atataaaatt agaatacgtt atgcaaatcc aaattcagat   1800
actgaaatca gtgtacaaat tacacaaaat aattctctat tacacagtga tacaataaca   1860
tttcatagta ctactgattc aaatatgaat aataatttat cacaaaatgt atatgttaca   1920
ggggaaaatg gaaattatac acttctagat ttatatgata ctactaatgt tttatcaaca   1980
ggagatatta cattacaaat tacaggagga agtcaagaaa tatttattga tcgaatagaa   2040
tttattccta ctgcgcctgc gcctgctcct actaacgaca ataacaatcc ccctttccac   2100
ggttgtttaa tagctggtga acaacaactt tgttctggac cacctaaatt tgaacaatta   2160
agtgatttag aaaaaattac aacacaagta tatatgttat tcaaatcttc ttcatatgaa   2220
gaattagatc caaaagtttc tagctatcaa attaatcaag tcgcattgaa agttatgtca   2280
ctatctgatg aaatgttttg tgaagaaaaa agattgttac gaaaattagt caataaagca   2340
aaacagttag tagaagcacg taacttacta gtaggtggaa gttttgatac acttcaaaat   2400
tggttacttg gaacaaatgc tactataaat tatgattcgt ttttatttaa tggaaattat   2460
ttattcttac aaccagcaag tggatttttc tcatcttatg cttatcaaaa aataaatgag   2520
tcaaaattaa aatcatatac acgatataaa gtttctggat tcattggaca aagtaatcaa   2580
gtagaactta ttatttctcg ttatggaaaa gaaattaata aaatattaaa tatttcatat   2640
gcagggcctc ttcctattac ttctaataca tcaacaactt gttgtgcacc aaatataggt   2700
caatgtaatg aagagcaatc taattctcat ttcttcagct atagcatcga tgtaggtgaa   2760
ctttaccccg aattaaatcc tggcattgaa tttggtcttc gtattgtgga accaaatagt   2820
tatatgacaa ttagtaattt agaaattatt gaagaacgtt cacttacaga aatggaaatt   2880
caaacaatca aacgaaaaga tcaaaaaatgg aaaaaagaaa tacttcaaga gtgtgcaaat   2940
attaacgaac ttttacaacc aattatagat aaagtcgatt cattattcaa agatgccgac   3000
tggtatggtc agattcttcc tcatatcaca tatcaaaatc taaaaaatat tgtattacct   3060
gaattaccta aattgagaca ttggtttata aacgatcttg caggtgaata ttatgaaatt   3120
gaacaaaaga tccagcaagc tctaaaacat gcatttagac aattagacga aagaaattta   3180
atccacaacg gtcactttac agctaactta atagattggc aaacagaagg taatgcccaa   3240
atgaaaatat tagaaaatgg tgctctcgca gcacaactct tgtcttggga ttctagtatt   3300
```

-continued

```
tcacaatctt taaatatatt agactttgat gaggataaag catataaact tcgtgtatat   3360

gctcaaggaa gcggaacaat ccaatttaaa aactgtgaag atgaaaccat ccaatttaat   3420

acaaactcat tcacatataa agaaaaaata ttctatttcg atactccatc aattaactta   3480

caaatacaat cagaaggttc taatttcgtt ataagtagta tcgagctcat tgaattatca   3540

gcagacgaa                                                           3549
```

<210> SEQ ID NO 29
<211> LENGTH: 1024
<212> TYPE: PRT
<213> ORGANISM: Bacillus thuringiensis

<400> SEQUENCE: 29

```
Met Asp Cys Asn Leu Arg Ser Gln Gln Asn Ile Pro Tyr Asn Val Leu
1               5                   10                  15

Ala Thr Gln Ala Ser Asn Leu Ser Gln Phe Thr Asp Ile Ala Glu Gly
            20                  25                  30

Val Lys Lys Ala Trp Ala Glu Phe Gln Lys Thr Gly Ser Phe Ser Leu
        35                  40                  45

Glu Ala Leu Lys Gln Gly Phe Asn Ala Ala Gln Gly Gly Thr Phe Asn
    50                  55                  60

Tyr Leu Ala Leu Leu Gln Ser Gly Ile Ser Leu Ala Gly Ser Phe Val
65                  70                  75                  80

Pro Gly Gly Ser Phe Val Ala Pro Ile Val Asn Met Val Ile Gly Trp
                85                  90                  95

Leu Trp Pro Asn Lys Asn Lys Thr Ala Asp Thr Glu Asn Leu Ile Lys
            100                 105                 110

Leu Ile Asp Glu Glu Ile Gln Lys Gln Leu Asn Lys Ala Leu Leu Glu
        115                 120                 125

Gln Asp Lys Asn Asn Trp Thr Ser Phe Leu Glu Ser Ile Phe Asp Val
    130                 135                 140

Ser Asn Thr Val Asn Asn Ala Ile Ile Asp Ala Gln Trp Ser Gly Thr
145                 150                 155                 160

Val Asp Asp Thr Asn Arg Gln Leu Lys Thr Pro Thr Thr Ser Asp Tyr
                165                 170                 175

Lys Asn Val Val Glu Lys Phe Asp Ser Ala Asp Thr Ala Ile Ile Thr
            180                 185                 190

Asn Glu Asn Gln Ile Met Asn Gly Asn Phe Asp Val Ala Ala Ser Ser
        195                 200                 205

Tyr Phe Val Ile Gly Ala Thr Leu Arg Leu Ala Leu Phe Gln Ser Tyr
    210                 215                 220

Ile Lys Phe Cys Asn His Trp Ile Asp Thr Val Gly Phe Asp Ser Asp
225                 230                 235                 240

Asn Tyr Asn Thr Gln Lys Ala Asn Leu Ala Arg Thr Lys Gln Thr Met
                245                 250                 255

Arg Thr Thr Ile Asn Asp Tyr Thr Gln Lys Ile Met Lys Val Phe Lys
            260                 265                 270

Asn Ser Asp Asn Met Pro Thr Met Gly Thr Asn Lys Phe Ser Val Asp
        275                 280                 285

Ala Tyr Asn Ala Tyr Ile Lys Gly Ile Thr Leu Asn Val Leu Asp Ile
    290                 295                 300

Val Ser Thr Trp Pro Ser Leu Tyr Pro Asn Asp Tyr Thr Ser Gln Thr
305                 310                 315                 320

Lys Leu Glu Gln Thr Arg Ile Ile Phe Ser Asn Met Ile Gly Gln Gln
```

-continued

```
                325                 330                 335

Glu Ala Ile Asp Gly Thr Val Thr Ile Tyr Asp Thr Phe Asp Ser Asp
            340                 345                 350

Asn Tyr Lys His Lys Pro Ile Pro Asn Asn Asn Val Asn Leu Leu Ser
        355                 360                 365

Tyr Phe Thr Asp Glu Leu Gln Asn Ile Gln Leu Ala Leu Tyr Thr Ala
    370                 375                 380

Pro Pro Lys His Lys Ser Asp Thr Arg Asp Ser Tyr Thr Tyr Pro Tyr
385                 390                 395                 400

Gly Phe Ile Leu Asn Tyr Gln Asn Ser Lys Tyr Lys Tyr Gly Asp Asn
                405                 410                 415

Glu Pro Val Ile Ser Asn Thr Ile Ser Ala Pro Ile Gln Gln Ile Asn
            420                 425                 430

Ala Ala Thr Gln Tyr Thr Gln Tyr Ile Asp Gly Glu Ser Ile Asn Gly
        435                 440                 445

Ile Gly Ala Tyr Leu Pro Gly Tyr Cys Ser Thr Asp Cys Ser Glu Ile
    450                 455                 460

Thr Pro Pro Phe Ala Cys Thr Ser Asn Asp Lys Asn Lys Ser Tyr Gly
465                 470                 475                 480

Ala Ser Cys Asn Ser Val Tyr Ser Ser Gln Lys Met Asn Ala Leu Tyr
                485                 490                 495

Pro Phe Thr Gln Thr Asn Val Pro Gly Asn Gln Gly Lys Leu Gly Val
            500                 505                 510

Leu Ala Ser Tyr Val Pro Tyr Asp Leu Asn Pro Lys Asn Ile Phe Gly
        515                 520                 525

Glu Val Asp Pro Asp Thr Asn Asn Ile Ile Leu Lys Gly Ile Pro Ala
    530                 535                 540

Glu Lys Gly Tyr Phe Ser Asn Tyr Thr Arg Pro Thr Val Val Lys Glu
545                 550                 555                 560

Trp Ile Asn Gly Ala Asn Ala Val Ser Leu Tyr Ser Gly Asn Thr Leu
                565                 570                 575

Phe Ile Val Ala Thr Asn Ile Thr Ala Thr Gln Tyr Lys Ile Arg Ile
            580                 585                 590

Arg Tyr Ala Asn Pro Asn Ser Asp Thr Glu Ile Ser Val Gln Ile Thr
        595                 600                 605

Gln Asn Asn Ser Leu Leu His Ser Asp Thr Ile Thr Phe His Ser Thr
    610                 615                 620

Thr Asp Ser Asn Met Asn Asn Asn Leu Ser Gln Asn Val Tyr Val Thr
625                 630                 635                 640

Gly Glu Asn Gly Asn Tyr Thr Leu Leu Asp Leu Tyr Asp Thr Thr Asn
                645                 650                 655

Val Leu Ser Thr Gly Asp Ile Thr Leu Gln Ile Thr Gly Gly Ser Gln
            660                 665                 670

Glu Ile Phe Ile Asp Arg Ile Glu Phe Ile Pro Thr Ala Pro Ala Pro
        675                 680                 685

Ala Pro Thr Asn Asp Asn Asn Asn Pro Pro Phe His Gly Cys Leu Ile
    690                 695                 700

Ala Gly Glu Gln Gln Leu Cys Ser Gly Pro Pro Lys Phe Glu Gln Leu
705                 710                 715                 720

Ser Asp Leu Glu Lys Ile Thr Thr Gln Val Tyr Met Leu Phe Lys Ser
                725                 730                 735

Ser Ser Tyr Glu Glu Leu Asp Pro Lys Val Ser Ser Tyr Gln Ile Asn
            740                 745                 750
```

```
Gln Val Ala Leu Lys Val Met Ser Leu Ser Asp Glu Met Phe Cys Glu
        755                 760                 765

Glu Lys Arg Leu Leu Arg Lys Leu Val Asn Lys Ala Lys Gln Leu Val
    770                 775                 780

Glu Ala Arg Asn Leu Leu Val Gly Gly Ser Phe Asp Thr Leu Gln Asn
785                 790                 795                 800

Trp Leu Leu Gly Thr Asn Ala Thr Ile Asn Tyr Asp Ser Phe Leu Phe
                805                 810                 815

Asn Gly Asn Tyr Leu Phe Leu Gln Pro Ala Ser Gly Phe Phe Ser Ser
            820                 825                 830

Tyr Ala Tyr Gln Lys Ile Asn Glu Ser Lys Leu Lys Ser Tyr Thr Arg
        835                 840                 845

Tyr Lys Val Ser Gly Phe Ile Gly Gln Ser Asn Gln Val Glu Leu Ile
    850                 855                 860

Ile Ser Arg Tyr Gly Lys Glu Ile Asn Lys Ile Leu Asn Ile Ser Tyr
865                 870                 875                 880

Ala Gly Pro Leu Pro Ile Thr Ser Asn Thr Ser Thr Thr Cys Cys Ala
                885                 890                 895

Pro Asn Ile Gly Gln Cys Asn Glu Glu Gln Ser Asn Ser His Phe Phe
            900                 905                 910

Ser Tyr Ser Ile Asp Val Gly Glu Leu Tyr Pro Glu Leu Asn Pro Gly
        915                 920                 925

Ile Glu Phe Gly Leu Arg Ile Val Glu Pro Asn Ser Tyr Met Thr Ile
    930                 935                 940

Ser Asn Leu Glu Ile Ile Glu Glu Arg Ser Leu Thr Glu Met Glu Ile
945                 950                 955                 960

Gln Thr Ile Lys Arg Lys Asp Gln Lys Trp Lys Lys Glu Ile Leu Gln
                965                 970                 975

Glu Cys Ala Asn Ile Asn Glu Leu Leu Gln Pro Ile Ile Asp Lys Val
            980                 985                 990

Asp Ser Leu Phe Lys Asp Ala Asp  Trp Tyr Gly Gln Ile  Leu Pro His
        995                 1000                 1005

Ile Thr  Tyr Gln Asn Leu Lys  Asn Ile Val Leu Pro  Glu Leu Pro
    1010                 1015                 1020

Lys


<210> SEQ ID NO 30
<211> LENGTH: 3094
<212> TYPE: DNA
<213> ORGANISM: Bacillus thuringiensis

<400> SEQUENCE: 30

tccgacgacg ttgcagtttc caacatggca tcagcaccat acgctatcac gggcattcca      60

actaccagag cccctgatgg agccctcccg cttcgtcaag agattgatgc ttggtctgcg     120

aacccagcca atgttgacca ggtgaactta tatctccagg cgcttgctgc tttccaacag     180

ttgcctgcga cagataagct ctcttacttc cagattgctg ggattcatgg ggagcctttt     240

atcccgtggg atgagaatac cagtcctaat ccaagatcta ggtggagagg atattgtaca     300

catgcatcaa tcctcttccc aacatggcat cggccgtatc tcgctgtctt cgagcaaatc     360

cttcattcga ttatgcagcg aattgcggca gcatatccag accaagagct tcgaacccga     420

tatcagactg ccgcagaagc attccgtatt ccatactggg acagtgcaca acttaaggaa     480

cgtgggggca gaagatcctt gaacgttcct tacctttgca ccttgcctac tgttcaagtc     540
```

-continued

```
ttcactccta cttccgctgg agatactatc aggccttttg aaactattga taatcccttg    600
tacagctaca aatttgtcac cacacaagga attactagtt tccaagacca ggatggaaat    660
ttctttccat tcgcaaacgc gatgggaact tcccgctatc caccacaata caattctcgc    720
gaccccaccg tttcttctca gtggaccaat ggattcgttg ataacgactc gatcacggag    780
gcactacgga atctgagttc tcttggtgag gacgtttacc gatcattcac gaccagcaat    840
tatgcctggt actctagcac ccaacaatca aatcccccag cgcccaacag ctaccaatct    900
ctcgaatcga ttcacaatga aatccacggc atcacaggag ggggtggaca tatgagctgg    960
aatacagttt catcttttga tcctattttc tggctccacc actgcaacgt ggatcgtctg   1020
tttgccatct ggcaagctat ctacgctgat accggccgat atcctgatgc ttggtttaat   1080
gcacaatcag cacaacttcg agacgaacga ggaacttggt cgattgctgc aggttctcgc   1140
gaaaatgctg acactccact agctccattc cataaggacg acagaggcag cgtctacaat   1200
tccaatgacg tccgcaattg gactaggttt ggctcttcgt accctgaatt gcaaccatgg   1260
cttcctcaat accgagattc cactggtgaa tttaacgcaa cgctatatcg taacgatgtt   1320
gttgcacagg tcaccgactt gtattcgcga gtcagaaggc gtgtccagaa cactcaagtt   1380
ccacgaaatc gcctttttgc tgccacccag accggcaccc agacattcca aggcagttcc   1440
gctactgcag gcgggtcgtt tgcggcccca ccgacaacac aagggcccgg tcagcagttg   1500
caatttggtc cccctccttc cggcgggcaa caggccttcg cccctccacc aacagtccaa   1560
gcccaagccc agtctcaagg acaaccattc accccgccaa cgacgctgcc cactcaggga   1620
cagcaattta cctctcctcc tcctcaaact gctcagggcc aacagttccc acccccgccg   1680
actcagcagc aacagttctc gccgccgccg actcatcagc agcaattcgc ccctcctcct   1740
acgcaggagc acggacaggc ggttacgtca ccacctgcac agacacaatt ctcccctccg   1800
ccaactcagg cattctcgcc gccaccgact ggtgattccc acggacagca gtttactcca   1860
cagccgcaac agcaattcac tccacaaccg caacagcaac agcaacagca atttgcgcct   1920
ccccagcaag gaccaggcgg ccatacccca cagggacagc atagctctcc accacccaag   1980
aaaagcggcc tcagtggcct tatgtcctct gctaaactgc actttggtga agcccttact   2040
gcaggccgtg aagccgctca aggccaccag cagcctgtac aacagcatca acagcccact   2100
cacactccag gaaaccctgg cagcagtggt actgctcttg ctactaaatt tggtggtatt   2160
attggaggcg gtattcatat ggcccaagaa cgtcttggtt ctaagaagca gccgggccaa   2220
cctggaaccc gtggtattga tgacgaacct ggtcaagaag gagaattgag ccgtggattc   2280
ggtgatatga gcttgggcca acaaagtttc ggctcaggag agtcgcttac ttaccacgaa   2340
tacgatgcaa acatccgatt tgagagattc gacctcggtg gtcgtccatt cacagtccac   2400
atcttccttg gagacttcaa cccggaccca gcaacttgga tgtgggacaa gaatcgtgtc   2460
ggtggaatct ataactttgt cgccggtgtt cagcgtggag acggaagcgc ttgctccaac   2520
tgcgaaactc aatcccagga ccacactatc gttacgggtc aggtgtctct cactaacgcc   2580
cttcttgacg acgttgaaga ctcagcaaat ggcttgaata gcctgattcc cgaggaggtt   2640
atcccgtatt tgcaacgaca tctgcactgg cgtatcactg acccgaatgg aagggagatc   2700
ccacgccaga gcctcaatac cttaaagatc tctgttgttg aatgttccgc caccatttca   2760
aacaaccccg gcgagctcac ccaatatggg gatcacagag tcttggacat agttactgaa   2820
ggtcgtccgg ctggcaaagc ggctggcgat ggttactaaa aaaaatctag tgaacccttt   2880
```

-continued

```
cagcatattg cacgcagatt gctgttttgt ttgttttatg tagggcattc gaattcgacg   2940

accctgaaat ttgcttcacg agcattaaat cagagaggga aatagtgaat attaaccgct   3000

gggcgagcgt cttttcatgt ttatgtactt aggcagttgc ctgtttttgc tggaatatat   3060

tttaattgag tcccaaaaaa aaaaaaaaaa aaaa                               3094


<210> SEQ ID NO 31
<211> LENGTH: 360
<212> TYPE: PRT
<213> ORGANISM: Bacillus thuringiensis

<400> SEQUENCE: 31

Met Arg Ile Arg Arg Asn Gln Ser Thr Leu Ser His Asn Glu Arg Leu
1               5                   10                  15

Ala Phe Thr Asn Ala Val Leu Glu Leu Lys Arg Arg Pro Ser Arg Leu
            20                  25                  30

Pro Met Ser Leu Gly Ser Thr Ser Arg Tyr Asp Asp Tyr Val Tyr Trp
        35                  40                  45

His Leu Gln Ser Met Glu Asn Gln Thr Ser Thr Thr Pro Gly Trp Ala
    50                  55                  60

His Arg Gly Pro Ala Phe Leu Pro Trp His Arg Tyr Tyr Leu Asn Gln
65                  70                  75                  80

Phe Glu Glu Asp Leu Gln Arg Ile Asp His Thr Val Thr Leu Pro Tyr
                85                  90                  95

Trp Asp Trp Thr Val Asp Asn Ser Thr Asp Ser Ser Val Pro Gly Ser
            100                 105                 110

Pro Trp Thr Asp Asp Phe Met Gly Gly Asp Gly Asp Pro Thr Gln Glu
        115                 120                 125

Tyr Thr Val Thr Thr Gly Pro Phe Thr Gly Asp Asn Trp Lys Leu Thr
    130                 135                 140

Leu Phe Asp His His Glu Asn Glu Pro His Asn Ala Arg Leu Arg Arg
145                 150                 155                 160

Gln Leu Gly Thr Thr Leu Asn Ala Ser Gly Asn Thr Ile Ser Ile Asn
                165                 170                 175

Leu Pro Thr Asp Ser Glu Val Gln Asn Cys Leu Leu Glu Thr Pro Tyr
            180                 185                 190

Tyr Val Ser Pro Trp Arg Ala Gly Gln Asp Val Asn Gln Pro Ala Leu
        195                 200                 205

Asn Pro Thr Lys Pro Ser Phe Cys Asn Arg Leu Glu Gly Trp Tyr Gly
    210                 215                 220

Ala Gly Ser Ile His Asn Lys Val His Val Trp Val Ala Gly Ala Thr
225                 230                 235                 240

Glu Gly Ser Met Ile Trp Met Ser Ser Pro Asn Asp Pro Val Phe Phe
                245                 250                 255

Leu His His Ala Asn Ile Asp Arg Leu Trp Val Gln Trp Gln Ala Asn
            260                 265                 270

Asn Pro Asn Glu Gly Tyr His Pro Thr Gly Asn Gly Asn Glu Val Gly
        275                 280                 285

Pro Thr Gly His Asn Leu Asn Asp Ser Met Asn Pro Trp Gly Arg Lys
    290                 295                 300

Val Thr Pro Asn Asn Val Leu Asn His Tyr Ser Leu Gly Tyr Thr Tyr
305                 310                 315                 320

Asp Thr Asp Ser Thr Pro Leu Ser Glu Ile Phe Met His Thr Phe Asn
                325                 330                 335
```

-continued

```
Leu Lys Ile Arg Lys Glu Lys Gln Ile Lys Asp Gly His Phe Gly Leu
            340                 345                 350

Ser Gln Glu Asp Leu Asp Lys Leu
        355                 360


<210> SEQ ID NO 32
<211> LENGTH: 17
<212> TYPE: PRT
<213> ORGANISM: Artificial Sequence
<220> FEATURE:
<223> OTHER INFORMATION: degenerate sequence
<220> FEATURE:
<221> NAME/KEY: misc_feature
<222> LOCATION: (8)..(9)
<223> OTHER INFORMATION: Xaa can be any naturally occurring amino acid

<400> SEQUENCE: 32

Lys Gly His Gly Thr Asp Glu Xaa Xaa Leu Ile Pro Ile Leu Ala Pro
1               5                   10                  15

Arg


<210> SEQ ID NO 33
<211> LENGTH: 5
<212> TYPE: PRT
<213> ORGANISM: Artificial Sequence
<220> FEATURE:
<223> OTHER INFORMATION: GXGTD motif
<220> FEATURE:
<221> NAME/KEY: misc_feature
<222> LOCATION: (2)..(2)
<223> OTHER INFORMATION: Xaa can be any naturally occurring amino acid

<400> SEQUENCE: 33

Gly Xaa Gly Thr Asp
1               5
```

ROOT-PREFERENTIAL AND STRESS INDUCIBLE PROMOTER AND USES THEREOF

CROSS REFERENCE TO RELATED APPLICATIONS

This application is a 35 U.S.C. 371 National Phase of PCT Application No. PCT/EP2016/067152 filed Jul. 19, 2016, which claims benefit to EP Application Nos. 15180269.1 filed Aug. 7, 2015, 15185057.5 filed Sep. 14, 2015, and 15185056.7 filed Sep. 14, 2015, the disclosure of each of which is hereby incorporated by reference in its entirety.

FIELD OF THE INVENTION

The present invention relates to the field of agricultural biotechnology, more specifically to the use of a transgene to improve plant yield under stress conditions. In particular, a method is provided to express a gene encoding an Annexin from *Brassica juncea* in plants to improve yield under drought stress condition. A stress induced root-preferential promoter is provided as well as an expression cassette for regulating the expression of Annexin preferentially in the roots under stress conditions.

BACKGROUND OF THE INVENTION

In recent years the phenomenon of global warming and its effect on crop plant production has become a crucial issue. Solving this problem at the plant level is almost exclusively a question of coping with plant stress. International agricultural and environmental research institutions as well as companies now re-discover plant stress as a major component of the effect of global warming on local and global food production. Research to meet these challenges involves widely diverging disciplines such as atmospheric sciences, soil science, plant physiology, biochemistry, genetics, plant breeding, molecular biology and agricultural engineering.

Abiotic plant environmental stress constitutes a major limitation to crop production. The major plant environmental stresses of contemporary economic importance worldwide are water stress including drought and flooding, cold (chilling and freezing), heat, salinity, water logging, soil mineral deficiency, soil mineral toxicity and oxidative stress. These factors are not isolated but also interrelated and influencing each other.

A major challenge in agriculture practice and research today is thus how to cope with plant environmental stress in an economical and an environmentally sustainable approach. In view of the already existing regions exposed to abiotic stress conditions in the world and the ongoing climate change, the provision of transgenic plants conferring resistance on at least one kind of abiotic stress is still a major goal in order to achieve a satisfying nutritional situation also in regions exposed to such abiotic stress in the world.

Cotton (*Gossypium* spp.) is the world's most important natural textile fiber and is also a significant oilseed crop. Cotton production provides income for approximately 250 million families, and approximately 150 countries are involved in cotton import and export. Its economic impact is estimated to be approximately $500 billion/year worldwide. World consumption of cotton fiber is approximately 115 million bales or approximately 27 million metric tons per year (National Cotton Council, www.cotton.org, 2006). The genus *Gossypium* is relatively complex and includes approximately 45 diploid (2n=2x=26) and five tetraploid (2n=4x=52) species, all exhibiting disomic patterns of inheritance. Diploid species (2n=26) fall into eight genomic groups (A-G, and K). The African clade, comprising the A, B, E, and F genomes, occurs naturally in Africa and Asia, while the D genome clade is indigenous to the Americas. A third diploid clade, including C, G, and K, is found in Australia. All 52 chromosome species, including *Gossypium hirsutum* and *Gossypium barbadense*, are classic natural allotetraploids that arose in the New World from interspecific hybridization between an A genome-like ancestral African species and a D genome-like American species. The closest extant relatives of the original tetraploid progenitors are the A genome species *Gossypium herbaceum* (A1) and *Gossypium arboreum* (A2) and the D genome species *Gossypium raimondii* (D5) 'Ulbrich'. Polyploidization is estimated to have occurred 1 to 2 million years ago, giving rise to five extant allotetraploid species. Interestingly, the A genome species produce spinnable fiber and are cultivated on a limited scale, whereas the D genome species do not. More than 95% of the annual cotton crop worldwide is *G. hirsutum*, Upland or American cotton, and the extra-long staple or Pima cotton (*G. barbadense*) accounts for less than 2% (National Cotton Council, www.cotton.org, 2006).

In addition to its importance for the textile industry, cotton agriculture also provides cottonseed to feed livestock, dairy cattle and poultry while cottonseed oil is used for food products like cooking oil (National Cotton Council, www.cotton.org, 2016).

Although cotton plants are naturally very drought tolerant compared to other crops and are mostly grown without irrigation (Cotton Today) cotton yield is severely affected by periods of drought especially at peak flowering, with each day of drought stress reducing lint yield by more than 18 kg/ha (Gibb et al. 2013, WATERpak section 3.1, p 117-126).

Soybean (*Glycine max* (L.) Merrill) is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board and American Soybean Association Special Report 92S, May 1990). Changes in fatty acid composition for improved oxidative stability and nutrition are constantly sought after. Industrial uses of soybean oil which is subjected to further processing include ingredients for paints, plastics, fibers, detergents, cosmetics, lubricants and biodiesel fuel. Soybean oil may be split, inter-esterified, sulfurized, epoxidized, polymerized, ethoxylated, or cleaved. Designing and producing soybean oil derivatives with improved functionality and improved oliochemistry is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein. For human consumption soybean meal is made into soybean flour which is processed to protein concentrates used for meat extenders or specialty pet foods. Production of edible protein ingredients from soybean offers a healthier, less expensive replacement for animal protein in meats as well as in dairy-type products. Whole soybeans are an excellent source of protein and dietary fiber. Soy protein is the only vegetable with a complete protein as it contains all eight amino acids essential for human health. Most soybeans are processed, or "crushed" into soybean meal and oil. Most of the soybean meal that is crushed is further processed into animal feed with the balance used to make soy flour and proteins. Of the oil fraction, most is consumed as edible oil, the rest is used for industrial products such as fatty acids, soaps, inks, hydraulic oil, grease, biodiesel, solvent, plastics and other products. Food uses of soybeans include traditional soy-foods such as tofu and soymilk as well as meat analogs and soy-based yogurts.

Soybeans grow on a variety of soils and a wide range of climates, and most soybeans are produced in the United States, Brazil, Argentina, China and India. A given area of land planted with soybeans can produce much more protein than land planted with other crops, or if the land were used to raise cattle. Soybean is however particularly sensitive to pests like nematodes which can cause yield losses of more than 30% in heavily infested field. Combined with drought the impact of the nematode infection increases dramatically and can lead to complete yield loss.

Many genes involved in stress response mechanisms in plants have been described in the art and some were demonstrated to confer some level of stress tolerance to the plant. For example, such genes encode antioxidant enzymes, synthetic genes of osmolytes, molecular chaperones like HSPs, enzymes involved in the production of plant hormones like abscisic acid (reviewed for example in Hu et al. 2014. Annu. Rev. Plant Biol. 65:715-41).

Despite the numerous reports of genes conferring abiotic stress tolerance in plants, few actually report a yield improvement in field condition. This limited success, reviewed for example in Cominelli et al. 2012, New Biotechnol, dx.doi.org/10.1016/j.nbt.2012.11.001, Lawlor 2013, J Exp Bot, Vol 64(1):83-108 and Tardieu 2012, J. Exp. Bot, Vol 63(1):25-31, is mainly attributed to agronomically unrealistic stress conditions and timing of stress application. Furthermore growth conditions are well controlled in laboratory or greenhouse experiments while field grown plants experience varying conditions and rarely a single stress. Genes conferring actual yield improvement under stress in field conditions are thus limited and the transferability of stress tolerance identified in laboratories or greenhouse experiments to field conditions is not straightforward.

To date, genes known to confer drought, salt or osmotic stress tolerance in cotton are the *Arabidopsis* vacuolar $H^+$ pyrophosphatase gene AVP1 (Pasapula et al. 2011, Plant Biotechnology Journal 9:88-99), the *Arabidopsis* EDT1 HDG11 gene involved in ABA signaling (Yu et al., 2016, Plant Biotechnol J, 14(1):72-84), the *Arabidopsis* LOS5 gene involved in ABA biosynthesis (Yue et al., 2012, J. Exp Bot, 63(10): 3741-3748), IPT gene involved in cytokinin biosynthesis (Kuppu et al. 2013, PLoS ONE 8(5): e64190), the rice SNAC1 gene (Liu et al. 2014, PLoS ONE 9(1): e86895), the annexin 1 gene from *Brassica juncea* AnnBj1 or *Gossypium hirsutum* GhAnn1 (Divya et al. 2010, Plant Mol. Biol. 73:293-308 and Zhang et al. 2015, Plant Mol. Biol., 87: 47-67 respectively) and the heat shock protein gene GHSP26 from *Gossypium arboreum* (Maqbool et al. 2009, Biotechnol. Prog. 26(1): 21-25). Of those, only AVP1 was shown to confer a yield increase under stress in the field.

Annexins (ANN) form a multigene family and have been so far identified in both plant and animal kingdom. They encode calcium-dependent membrane binding proteins involved in the calcium dependent polar growth of cells like root hairs, pollen and cotton fibers. Annexins are defined by their highly conserved fold consisting of four or more repeats of a so-called annexin-repeat domain signature sequence (Barton et al. 1991, Eur. J. Biochem. 198: 749-760).

Annexins are ubiquitously expressed and their expression level is modulated by environmental stimuli like light, gravity, abiotic stresses and wounding suggesting a role in mediating stress response. Such role is supported by the discovery that ANN s from *Arabidopsis thaliana* and *Brassica juncea* were found to have peroxidase activity (Gorecka et al., 2005, Biochem Biophys Res Commun, 336(3):868-875, Divya et al., 2010, Plant Mol. Biol. 73:293-308), therefore able to act as cellular antioxidant.

The involvement of ANN1 in stress response was studied in *Arabidopsis*, tobacco, and cotton. Loss of function analysis of Atann1 and Atann4 mutants indicated an increased sensitivity to salt and osmotic stress as well as a reduced germination rate and growth following abscisic acid treatment (US application 2005/089872). Cantero et al. (2006, Plant Physiology and Biochemistry, 44: 13-24) showed that AtANN1 is upregulated by cold, heat, drought and salt stress. The *Arabidopsis* Atann1 knockout mutant accumulates more reactive oxygen species and is more sensitive to severe drought stress than wild type. *Arabidopsis* plants overexpressing AtANN1 were found more drought tolerant as they could resurrect from a severe desiccation (Konopka-Postupolska et al., 2009, Plant Physiology, 150: 1394-1410). Furthermore, rice plants expressing AtANN1 constitutively or preferentially in the green tissues had an increased yield under both optimal and drought stress conditions (US application 2010/0170011).

*Arabidopsis* lines engineered to overexpress the Lotus Annexin1 (NnAnn1) were found to have an improved germination rate under heat stress (patent application CN102229662).

The Annexin1 gene of *Brassica juncea* (AnnBj1) is induced by ABA, salt and peroxide treatments (Jami et al., 2009, Plant Physiology and Biochemistry 47: 977-990). Tobacco plants constitutively expressing AnnBj1 were shown to be more tolerant to drought (mannitol), salt and oxidative stress in survival assays at the seedling stage (Jami et al., 2008, Plant Physiology and Biochemistry, 46: 1019-1030). Similarly cotton plants constitutively expressing AnnBj1 had increased tolerance to salt, osmotic and oxidative stress at the seedling stage (Divya et al., 2010, Plant Mol. Biol. 73: 293-308). Furthermore, these transgenic plants were shown to maintain normal seed development and fiber quality when grown under salt stress (Divya et al., 2010, Plant Mol. Biol. 73:293-308).

In cotton, GhAnn1 expression is induced upon treatment with ABA, peroxide, salt and PEG (Zhang et al., 2015, Plant Mol. Biol. 87: 47-67). Germination and seedling growth of cotton plants overexpressing GhAnn1 was studied under various stresses. Overexpressing lines germinated faster and showed better seedling growth than wild type when subjected to salt or drought (PEG) stress, indicating a better stress tolerance (Zhang et al., 2015, Plant Mol. Biol. 87: 47-67).

Even though the prior art described an improved germination and early growth in cotton under various abiotic stresses, and yield increase in rice, the prior art does not reveal an increase of cotton fiber yield. There remains thus a need to increase cotton yield (lint yield and seed yield) under drought stress in field condition. To that end, appropriate expression (spatial, temporal) is also required. There also remains a need to obtain a more consistent increase in yield in plants, particularly under drought conditions, particularly in field conditions.

Genetic modification of plants to alter and/or improve phenotypic characteristics (such as productivity or quality) relies on the availability of a means to drive and to control gene expression as required. Indeed, genetic modification relies on the availability and use of suitable promoters which are effective in plants and which regulate transcription so as to give the desired effect(s) in the transgenic plant.

For numerous applications in plant biotechnology it is required to express the transgenes in a tissue-preferential and/or an inducible manner to avoid the undesirable effects the transgene expression could cause in other tissues or at times it is not required.

Root-preferential promoters are useful for expressing or down-regulating genes preferentially in the roots to get the desired function or effect, such as improving the resistance to soil-borne pathogens or root pathogens, improving tolerance to abiotic stress, such as temperature, water or salt stress, broadening the range of soils in which the plant may grow, altering root architecture, such as root density, or root strength, altering or improving nutrient uptake and/or nutrient use, modifying the interaction between the roots and above-ground biomass, or modifying metabolic pathways in the root.

Examples of root-preferential promoters include the RB7 promoter from *Nicotiana tabacum* (U.S. Pat. Nos. 5,459,252 and 5,750,386); the ARSK1 promoter from *Arabidopsis thaliana* (Hwang and Goodman (1995) Plant J 8:37-43), the MR7 promoter from *Zea mays* (U.S. Pat. No. 5,837,848), the ZRP2 promoter of *Zea mays* (U.S. Pat. No. 5,633,363), and the MTL promoter from *Zea mays* (U.S. Pat. Nos. 5,466,785 and 6,018,099), the pLTP and TIP2-3 promoters from *Sorghum bicolor* (WO2014/164399A1 and WO2014/159113A1 respectively), Class-H-Patatin-Promotor (Köster-Töpfer et al., Mol. Gen. Genet. 219 (1989), 390-396), Agropinsynthase-Promotor (ags) (Inoguchi et al., Plant Phys. 149 (1996), 73-78), AKT1 promoter (Lagarde et al., Plant J. 9 (1996), 195-203), and TobRB7 promoter (Yamamoto et al., Plant Cell 3 (1991), 371-382).

Stress-inducible promoters are useful for expressing or down-regulating genes specifically in stressful conditions to get the desired function or effect, such as improving the tolerance to abiotic stress, such as temperature, water or salt stress.

Examples of abiotic stress inducible promoters include the drought-inducible rd29a promoter from *Arabidopsis thaliana* (Yamaguchi-Shinozaki et al. 1993, Mol. Gen. Genet., 236: 331-340), the heat-inducible HSP81.1 from *Arabidopsis thaliana* (Takahashi et al., 1992, Plant Physiol., 99: 383-390), and the drought-inducible rab17 promoter from *Zea mays* (Morran et al., 2011, Plant Biotechnology Journal, 9: 230-249).

Few promoters combining both the tissue specificity and the stress inducibility have been isolated. Examples of such promoters include the shoot specific and drought stress inducible HPR1 promoter of *Arabidopsis* (Wang et al., 2009, Molecular Plant, 2(1): 191-200), the shoot specific and salt and drought stress inducible AlSAP promoter from *Aeluropus littoralis* (Saad et al., 2011, Transgenic Res, 20: 1003-1018), the root specific and osmotic stress responsive EgTIP2 promoter of *Eucalyptus grandis* (Rodrigues et al., 2013, Plant Science, 213: 106-113) and the salt-inducible and root epidermis specific btg-26 promoter from *Brassica napus* (WO 2001/055433, US2005044585A1), also demonstrated to be functional in barley (Good et al., 2007, Can J. Bot. 85: 252-262) and the promoter of its orthologous gene from rice OsANT1 (U.S. Pat. No. 7,982,093).

There is a need for further promoters conferring tissue-specificity, stress-inducibility or both, particularly promoters controlling stress-induced and/or root-preferential expression in plants, such as *Gossypium* plants, *Glycine* plants and *Triticum* plants.

It is an objective of the present invention to increase yield in plants, such as increasing cotton yield including lint yield or seed yield under drought stress in field condition. It is another objective to obtain a more consistent increase in yield in plants, such as cotton lint yield or cotton seed yield. These and other problems are solved as hereinafter described, particularly in the different embodiments, examples and claims. Also provided is a *Gossypium* promoter for stress-induced and/or root-preferential expression of genes of interest in plants.

SUMMARY OF THE INVENTION

In one aspect, the invention provides an isolated nucleic acid comprising root-preferential and stress-inducible promoter activity selected from the group consisting of (a) a nucleic acid comprising a nucleotide sequence of SEQ ID NO: 7 or a functional fragment thereof; (b) a nucleic acid comprising a nucleotide sequence having at least about 95% sequence identity to SEQ ID NO: 7 or a functional fragment thereof; and (c) the nucleic acid of a functional promoter hybridizing under stringent conditions to the nucleotide sequence of SEQ ID NO: 7, or a functional fragment thereof; wherein said functional fragment comprises at the 400 bp sequence upstream of the transcription start of SEQ ID NO: 7.

A further embodiment provides a recombinant gene comprising the nucleic acid according to the invention operably linked to a heterologous nucleic acid sequence encoding an expression product of interest, and optionally a transcription termination and polyadenylation sequence, preferably a transcription termination and polyadenylation region functional in plant cells. In a further embodiment, said expression product of interest is an RNA capable of modulating the expression of a gene or is a protein.

Yet another embodiment provides a host cell, such as an *E. coli* cell, an *Agrobacterium* cell, a yeast cell, or a plant cell, comprising the isolated nucleic acid according to the invention, or the recombinant gene according to the invention.

In a further embodiment, a plant is provided comprising the recombinant gene according to the invention. A further embodiment provides plant parts and seeds obtainable from the plant according to the invention. These plant parts and seeds comprise the recombinant gene described above. In another embodiment, the plants, plant parts or seeds according to the invention are cotton, soybean or wheat plants, plant parts or seeds. It can also be expected that this promoter would be functional in other dicotyledonous and monocotyledonous plants.

Yet another embodiment provides a method of producing a transgenic plant comprising the steps of (a) introducing or providing the recombinant gene according to the invention to a plant cell to create transgenic cells; and (b) regenerating transgenic plants from said transgenic cell.

Further provided are methods of effecting root-preferential, stress-inducible, and combined root-preferential and stress-inducible expression of a nucleic acid comprising introducing the recombinant gene according to the invention into the genome of a plant, or providing the plant according to the invention. Also provided is a method for altering biotic or abiotic stress tolerance, root architecture, nutrient use efficiency, or yield of a plant, said method comprising introducing the recombinant gene according to the invention into the genome of a plant, or providing the plant according to the invention. In another embodiment, said plant is a cotton, a soybean or a wheat plant.

Also provided is the use of the isolated nucleic acid according to the invention to regulate expression of an operably linked nucleic acid in a plant, and the use of the isolated nucleic acid according to the invention, or the recombinant gene according to the invention to alter biotic or abiotic stress tolerance, root architecture, nutrient use efficiency, or yield of a plant. In a further embodiment, said plant is a cotton, a soybean or a wheat plant.

Yet another embodiment provides a method of producing food, feed, or an industrial product comprising (a) obtaining the plant or a part thereof, according to the invention; and (b) preparing the food, feed or industrial product from the plant or part thereof. In another embodiment, said food or feed is oil, meal, ground or crushed seeds, soybean flakes, grain, starch, flour or protein, or said industrial product is biofuel, fiber, industrial chemicals, a pharmaceutical or a nutraceutical. Such food, feed or industrial products contain the root-preferential, stress-inducible and stress-induced root-preferential promoter described herein.

In another aspect, the invention provides a recombinant gene comprising (a) a plant expressible promoter selected from the group consisting of i) root-preferential promoter, ii) stress-inducible promoter and iii) stress-induced root-preferential promoter, (b) a nucleic acid sequence encoding an Annexin protein (c) and optionally, a transcription termination and polyadenylation sequence, preferably a transcription termination and polyadenylation region functional in plants.

In a further embodiment the root preferential promoter is the Pbtg-26GhD10 promoter.

In another embodiment the nucleic acid sequence encoding an Annexin protein comprises (a) a nucleotide sequence of SEQ ID NO: 12 or SEQ ID NO: 14; (b) a nucleotide sequence at least 80% identical to SEQ ID NO: 12 or SEQ ID NO: 14 (c) a nucleotide sequence of a nucleic acid capable of hybridizing under stringent conditions to the nucleotide sequence of SEQ ID NO: 12 or SEQ ID NO: 14, (d) a nucleotide sequence encoding the amino acid sequence of SEQ ID NO: 13 or SEQ ID NO: 15 (e) a nucleotide sequence encoding the amino acid sequence having at least 80% identity with SEQ ID NO: 13 or SEQ ID NO: 15, (f) a nucleotide sequence encoding a protein comprising four or more annexin-repeated domains.

In yet another aspect, the invention provides a method to increase the yield, such as fiber yield and seed yield, of a plant, such as a cotton, a soybean or a wheat plant, compared to a control plant under stress condition comprising (a) providing to cells of said plant a recombinant gene comprising (i) a heterologous plant expressible promoter, (ii) a nucleic acid sequence encoding an Annexin protein (iii) and optionally, a transcription termination and polyadenylation sequence, preferably a transcription termination and polyadenylation region functional in plants, and (b) regenerating said plant.

In a further embodiment the heterologous plant expressible promoter is selected from the group consisting of a) a root-preferential promoter, b) a stress-inducible promoter and c) a stress-induced root-preferential promoter. In another embodiment said promoter is the Pbtg26-GhD10 promoter.

In a further embodiment the heterologous plant expressible promoter is a constitutive promoter. In another embodiment said promoter is the Cauliflower Mosaic Virus CaMV35S promoter.

In another embodiment the nucleic acid sequence encoding an Annexin protein comprises (a) a nucleotide sequence of SEQ ID NO: 12 or SEQ ID NO: 14; (b) a nucleotide sequence at least 80% identical to SEQ ID NO: 12 or SEQ ID NO: 14 (c) a nucleotide sequence of a nucleic acid capable of hybridizing under stringent conditions to the nucleotide sequence of SEQ ID NO: 12 or SEQ ID NO: 14, (d) a nucleotide sequence encoding an amino acid sequence of SEQ ID NO: 13 or SEQ ID NO: 15 (e) a nucleotide sequence encoding an amino acid sequence having at least 80% identity with SEQ ID NO: 13 or SEQ ID NO: 15, (f) a nucleotide sequence encoding a protein comprising four or more annexin-repeated domains.

Further embodiments disclose the stress as a drought stress, occurring during the plant reproductive stage, on field-grown plants.

Another embodiment provides a method to increase yield of a plant. In a further embodiment, said plant is a cotton, a soybean or a wheat plant.

The present invention provides a method to increase lint yield and a method to increase seed yield. In a further embodiment the increased yield compared to a control plant is at least 5%.

According to the present invention, the method provided more consistently increased yield when the promoter used is selected from the group of root-preferential, stress-inducible or stress-induced root-preferential promoters, preferentially the Pbtg-26GhD10 promoter, compared to when the promoter used is a constitutive plant expressible promoter, preferentially the CaMV35S promoter.

The invention further provides plants, plant parts or plants cells comprising the provided recombinant gene. In a specific embodiment, the plant, plant part or plant cell is cotton, soybean or wheat.

BRIEF DESCRIPTION OF THE FIGURES

FIG. 1: alignment of promoter regions of the btg-26 gene from subgenome A and from subgenome D of *Gossypium hirsutum*. The nucleotide sequence of the promoter of subgenome A (upper sequence) corresponds to the nucleotide sequence of SEQ ID NO: 4 from position 472 to position 1486. The nucleotide sequence of promoter of subgenome D (lower sequence) corresponds to the nucleotide sequence of SEQ ID NO: 5 from position 2067 to position 3089. Differences in nucleotide sequence are indicated by gray boxes. Nucleotides which do not have a corresponding nucleotide in the other promoter region are indicated by dashes in the nucleotide sequence missing the nucleotides. The first nucleotide of each promoter fragment of ca. 0.6kb is underlined. The predicted TATA box is double underlined while the transcription initiation start is wave-underlined. Predicted ABA-responsive element-like binding site motifs (ABRE-like motifs) are framed. Nucleotides between brackets are replaced by the sequence ACC in the T-DNAs due to the creation of a NcoI restriction site required for the cloning of the promoters. The translation START codon is indicated in bold. Overall identity between the two promoter regions is of about 78% sequence identity. Sequence identity between the ca. 600 bp upstream of the translation start of the two promoters is about 94%.

FIG. 2: Alignment of the amino acid sequence of different Annexin proteins. Amino acid residues conserved in all proteins are indicated by an asterisk. Conserved amino-acid substitutions are indicated by a column. Annexin-repeat domains are underlined. The 17 aminoacid endonexin fold region with its characteristic KGhGTDEXXLIpILApR motifs (SEQ ID NO: 32) are framed. The conserved Histidine residue for peroxidase activity is indicated in bold on a grey background. The conserved phospholipid binding sites (Tryptophan residues) are indicated in bold on a yellow background. The type II calcium binding sequences (GXGTD motifs; SEQ ID NO: 33) are highlighted in green. AnnBj1: Annexin1 protein from Brassicajuncea (SEQ ID NO: 13); AtAnn1: Annexin1 protein from *Arabidopsis thaliana* (SEQ ID NO: 17); GhAnn1: Annexin1 protein from *Gossypium hirsutum* (SEQ ID NO: 15). Amino-acids which do not have a corresponding nucleotide in the other protein sequence are indicated by dashes in the amino-acid sequence missing the amino-acids. Overall identity between AnnBj1 and AtAnn1 is about 91%, between AnnBj1 and GhAnn1 about 70% and between AtAnn1 and GhAnn1 about 72%.

FIG. 3: Alignment of the nucleotide sequence of different Annexin coding sequences. AnnBj1: Annexin1 coding sequence from *Brassica juncea* (SEQ ID NO: 12); AtAnn1: Annexin1 coding sequence from *Arabidopsis thaliana* (SEQ ID NO: 16); GhAnn1: Annexin1 coding sequence from *Gossypium hirsutum* (SEQ ID NO: 14). Nucleotides conserved in all three sequences are indicated with an asterisk. Nucleotides conserved only between the AnnBj1 and AtAnn1 sequences are indicated with a column. Nucleotides conserved only between the AnnBj1 and GhAnn1 sequences are indicated with a semi-column. Nucleotides conserved only between the AtAnn1 and GhAnn1 sequences are indicated with a point. Nucleotides which do not have a corresponding nucleotide in the other nucleotide sequence are indicated by dashes in the nucleotide sequence missing the nucleotides. Overall identity between the coding sequences is about 70% between AtAnn1 and GhAnn1 and between AnnBj1 and GhAnn1 and is about 89% between AnnBj1 and AtAnn1.

DETAILED DESCRIPTION OF THE INVENTION

The present invention is based on the surprising discovery that the expression of an Annexin in a plant lead to an increased yield under stress condition in the field compared to their respective control plants. Furthermore, the promoter sequence from the D genome of *Gossypium hirsutum* Pbtg-26GhD10 was found to exhibit stress-induced root-preferential promoter activity in plants. It was moreover discovered that the yield increase obtained when expressing an Annexin is more consistently obtained when the Annexin is expressed under control of a stress-induced root-preferential promoter than when the expression of the same Annexin is under control of a constitutive promoter.

In a first aspect, the invention provides an isolated nucleic acid comprising root-preferential and stress-inducible promoter activity selected from the group consisting of (a) a nucleic acid comprising a nucleotide sequence of SEQ ID NO: 7 or a functional fragment thereof; (b) a nucleic acid comprising a nucleotide sequence having at least about 95% sequence identity to SEQ ID NO: 7, or a functional fragment thereof; and (c) the nucleic acid of a functional promoter capable of hybridizing under stringent conditions to the nucleotide sequence of SEQ ID NO: 7, or a functional fragment thereof; wherein said functional fragment comprises at least the 400 bp sequence upstream of the transcription start of SEQ ID NO: 7.

Promoter

SEQ ID NO: 7 represents the ca. 1 kb long sequence of the btg-26Gh-D promoter upstream of the translation start of *Gossypium hirsutum*. SEQ ID NO: 7 is a preferred promoter fragment in this invention, however alternative functional fragments may be used. Such functional fragment would preferably be longer than 600, longer than 700, longer than 800 or even longer than 900 consecutive nucleotides upstream of the transcription start site (SEQ ID No 7 nucleotide position 755) or be longer than 700, longer than 800, longer than 900 or even longer than 1000 consecutive nucleotides upstream of the translation start site (FIG. 1 nucleotide positions 1022-1024) and promote transcription of an operably linked nucleic acid preferentially in the roots and in a stress-inducible manner. A promoter fragment according to the invention may thus comprise a nucleotide sequence of SEQ ID No: 7 from the nucleotide at position 351 to the nucleotide at position 755. Alternatively, a promoter fragment according to the invention may thus comprise a nucleotide sequence of SEQ ID No: 7 from the nucleotide at position 251 to the nucleotide at position 755. Yet another promoter fragment according to the invention may thus comprise a nucleotide sequence of SEQ ID No: 7 from the nucleotide at position 151 to the nucleotide at position 755. Still another promoter fragment according to the invention may thus comprise a nucleotide sequence of SEQ ID No: 7 from the nucleotide at position 51 to the nucleotide at position 755. Yet another promoter fragment according to the invention may thus comprise a nucleotide sequence of SEQ ID No: 7 from the nucleotide at position 1 to the nucleotide at position 755.

The nucleic acid comprising the stress-induced root-preferential promoter activity according to the invention may also be comprised in a larger DNA molecule.

"Root-preferential promoter activity" in the context of this invention means the promoter activity is at least 2 times, or at least 5 times, or at least 10 times, or at least 20 times or even at least 100 times higher in roots than in other tissues. In other words, in root-preferential promoter activity, transcription of the nucleic acid operably linked to the promoter of the invention in the roots is at least 2 times, or at least 5 times, or at least 10 times, or at least 20 times or even at least 100 times higher than in other tissues. In other words, the root-preferential promoter controls root-preferential expression of the nucleic acid operably linked to the root-preferential promoter. "Root-preferential promoter activity" encompasses "stress-induced root-preferential promoter activity".

"Stress-inducible promoter activity" means the promoter activity is at least 2 times, or at least 5 times, or at least 10 times, or at least 20 times or even at least 100 times higher when the plant or plant part is subjected to environmental stress than in control condition. In other words, in stress-inducible promoter activity, transcription of the nucleic acid operably linked to the promoter of the invention is at least 2 times, or at least 5 times, or at least 10 times, or at least 20 times or even at least 100 times higher when the plant or plant part is subjected to stress than in control condition. In other words, the stress-inducible promoter controls stress-inducible expression of the nucleic acid operably linked to the stress-inducible promoter. "Stress-inducible promoter activity" encompasses "stress-induced root-preferential promoter activity".

"Stress induced root-preferential promoter activity" means the promoter activity is at least 2 times, or at least 5 times, or at least 10 times, or at least 20 times or even at least 100 times higher in the roots compared to other plant tissues when the plant or plant part is subjected to environmental stress. In other words, in stress-induced root-preferential promoter activity, transcription of the nucleic acid operably linked to the promoter of the invention is at least 2 times, or at least 5 times, or at least 10 times, or at least 20 times or even at least 100 times higher in the root tissues than in other plant tissues when the plant or plant part is subjected to stress. In other words, the stress-induced root-preferential promoter controls stress-induced root-preferential expression of the nucleic acid operably linked to the stress-induced root-preferential promoter.

As used herein, "promoter" means a region of DNA sequence that is essential for the initiation of transcription of DNA, resulting in the generation of an RNA molecule that is complementary to the transcribed DNA; this region may also be referred to as a "5' regulatory region". Promoters are usually located upstream of the coding sequence to be transcribed and have regions that act as binding sites for RNA polymerase II and other proteins such as transcription factors (trans-acting protein factors that regulate transcription) to initiate transcription of an operably linked gene. Promoters may themselves contain sub-elements (i.e. promoter motifs) such as cis-elements or enhancer domains that regulate the transcription of operably linked genes. The promoters of this invention may be altered to contain "enhancer DNA" to assist in elevating gene expression. As is known in the art, certain DNA elements can be used to enhance the transcription of DNA. These enhancers often are found 5' to the start of transcription in a promoter that functions in eukaryotic cells, but can often be inserted upstream (5') or downstream (3') to the coding sequence. In some instances, these 5' enhancer DNA elements are introns. Among the introns that are useful as enhancer DNA are the 5' introns from the rice actin 1 gene (see U.S. Pat. No. 5,641,876), the rice actin 2 gene, the maize alcohol dehydrogenase gene, the maize heat shock protein 70 gene (see U.S. Pat. No. 5,593,874), the maize shrunken 1 gene, the light sensitive 1 gene of *Solanum tuberosum*, the *Arabidopsis* histone 4 intron and the heat shock protein 70 gene of *Petunia hybrida* (see U.S. Pat. No. 5,659,122). Thus, as contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed.

A promoter as used herein may thus include sequences downstream of the transcription start, such as sequences coding the 5' untranslated region (5' UTR) of the RNA or introns located downstream of the transcription start. A promoter fragment according to the invention may comprise its own 5'UTR comprising the nucleotide sequence of SEQ ID No: 7 from nucleotide 756 to nucleotide 1022. As experimentally demonstrated the last three nucleotides from the 5'UTR of the herein described promoters can be exchanged for other nucleotides to create a convenient restriction enzyme recognition site. Thus a promoter fragment according to the invention may comprise its own 5'UTR comprising the nucleotide sequence of SEQ ID No: 7 from nucleotide 756 to nucleotide 1019. In combination with the above described promoter fragments, a promoter fragment according to the invention may thus comprise the nucleotide sequence of SEQ ID No: 7 from the nucleotide at position 351 to the nucleotide at position 1019, or the nucleotide sequence of SEQ ID No: 7 from the nucleotide at position 251 to the nucleotide at position 1019 or the nucleotide sequence of SEQ ID No: 7 from the nucleotide at position 151 to the nucleotide at position 1019, or the nucleotide sequence of SEQ ID No: 7 from the nucleotide at position 51 to the nucleotide at position 1019, or the nucleotide sequence of SEQ ID No: 7 from the nucleotide at position 1 to the nucleotide at position 1019 such as the nucleotide sequence of SEQ ID No: 7 from the nucleotide at position 351 to the nucleotide at position 1022, or the nucleotide sequence of SEQ ID No: 7 from the nucleotide at position 251 to the nucleotide at position 1022 or the nucleotide sequence of SEQ ID No: 7 from the nucleotide at position 151 to the nucleotide at position 1022, or the nucleotide sequence of SEQ ID No: 7 from the nucleotide at position 51 to the nucleotide at position 1022, or the nucleotide sequence of SEQ ID No: 7 from the nucleotide at position 1 to the nucleotide at position 1022. Alternatively, 5'UTR fragments from other genes may be used.

Promoter activity for a functional promoter fragment in roots and promoter activity for a functional promoter fragment under stress may be determined by those skilled in the art, for example using analysis of RNA accumulation produced from the nucleic acid which is operably linked to the promoter as described herein, whereby the nucleic acid which is operably linked to the promoter can be the nucleic acid which is naturally linked to the promoter, i.e. the endogenous gene of which expression is controlled by the promoter.

The RNA accumulation, or levels of RNA, such as mRNA, can be measured either at a single time point or at multiple time points and as such the fold increase can be average fold increase or an extrapolated value derived from experimentally measured values. As it is a comparison of levels, any method that measures mRNA levels can be used. In a preferred aspect, the tissue or organs compared are root tissues with other tissues of the organism. In another preferred aspect, multiple tissues or organs are compared. A preferred multiple comparison is root tissue compared with 1 or 2 tissues or organs selected from the group consisting of leaves and stems or leaf tissue under stress. Another preferred multiple comparison is tissues or organs under stress condition compared with tissues or organs under control condition. As used herein, examples of plant organs are fiber, leaf, root, etc. and example of tissues are leaf primordia, shoot apex, vascular tissue, etc.

The root-preferential, stress-inducible or stress-induced root-preferential expression capacity of the identified or generated fragment of the promoter can be conveniently tested by operably linking such DNA molecules to a nucleotide sequence encoding an easy scorable marker, e.g. a beta-glucuronidase gene, introducing such a recombinant gene into a plant and analyzing the expression pattern of the marker in roots as compared with the expression pattern of the marker in other parts of the plant. Other candidates for a marker (or a reporter gene) are chloramphenicol acetyl transferase (CAT) and proteins with fluorescent properties, such as green fluorescent protein (GFP) from *Aequora victoria*. To define a minimal promoter region, a DNA segment representing the promoter region is removed from the 5' region of the gene of interest and operably linked to the coding sequence of a marker (reporter) gene by recombinant DNA techniques well known to the art. The reporter gene is linked downstream of the promoter, so that transcripts initiating at the promoter proceed through the reporter gene. Reporter genes generally encode proteins, which are easily measured, including, but not limited to, chloramphenicol acetyl transferase (CAT), beta-glucuronidase (GUS), green fluorescent protein (GFP), beta-galactosidase (beta-GAL), and luciferase. The expression cassette containing the reporter gene under the control of the promoter can be introduced into an appropriate cell type by transfection techniques well known to the art. To assay for the reporter protein, cell lysates are prepared and appropriate assays, which are well known in the art, for the reporter protein are performed. The level of enzyme activity corresponds to the amount of enzyme that was made, which in turn reveals the level of expression and the root-specific functionality from the promoter or promoter fragment of interest. This level of expression can also be compared to other promoters to determine the relative strength of the promoter under study. Once activity and functionality is confirmed, additional mutational and/or deletion analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then again introduced in cells and their activity and/or functionality determined.

The activity or strength of a promoter may be measured in terms of the amount of mRNA or protein accumulation it specifically produces, relative to the total amount of mRNA or protein. The promoter preferably expresses an operably linked nucleic acid sequence at a level greater than about 0.1%, about 0.2%, about 0.5%, more preferably greater than about 1% of the total mRNA. Alternatively, the activity or strength of a promoter may be expressed relative to a well-characterized promoter (for which transcriptional activity was previously assessed).

It will herein further be clear that equivalent root-preferential, stress-inducible and stress-induced root-preferential promoters can be isolated from other *Gossypium* plants carrying the D genome like for example *Gossypium raimondii, Gossypium barbadense* and *Gossypium darwinii*. To this end, orthologous promoter fragments may be isolated from other plants using SEQ ID NO: 7 or a functional fragment having at least 600 consecutive nucleotides thereof as a probe and identifying nucleotide sequences from these other plants which hybridize under the herein described hybridization conditions. By way of example, a promoter of the invention may be used to screen a genomic library of a crop or plant of interest to isolate corresponding promoter sequences according to techniques well known in the art. Thus, a promoter sequence of the invention may be used as a probe for hybridization with a genomic library under medium to high stringency conditions. As an alternative equivalent promoters can be isolated using the coding sequences of the genes controlled by the promoters of SEQ ID NO: 7 to screen a genomic library (e.g. by hybridization or in silico) of a crop of interest. When sufficient identity between the coding sequences is obtained (for example, higher than 95% identity), promoter regions can be isolated upstream of the orthologous genes.

Suitable to the invention are nucleic acids comprising root-preferential, stress-inducible or stress-induced root-preferential promoter activity which comprise a nucleotide sequence having at least 95%, or at least 98% or at least 99% sequence identity to the herein described promoters and promoter regions or functional fragments thereof and are also referred to as variants. The term "variant" with respect to the transcription regulating nucleotide sequence SEQ ID NO: 7 of the invention is intended to mean substantially similar sequences. Naturally occurring allelic variants such as these can be identified with the use of well-known molecular biology techniques, as, for example, with polymerase chain reaction (PCR) and hybridization techniques as herein outlined before. Variant nucleotide sequences also include synthetically derived nucleotide sequences, such as those generated, for example, by using site-directed mutagenesis of SEQ ID NO: 7. Generally, nucleotide sequence variants of the invention will have generally at least 80%, e.g. 81%, 82%, 83%, 84%, at least 85%, e.g. 86%, 87%, 88%, 89%, 90%, 91%, 92%, 93%, 94%, 95%, 96%, 97%, to 98% and 99% nucleotide sequence identity to the native (wild type or endogenous) nucleotide sequence or a functional fragment thereof. Derivatives of the DNA molecules disclosed herein may include, but are not limited to, deletions of sequence, single or multiple point mutations, alterations at a particular restriction enzyme site, addition of functional elements, or other means of molecular modification which may enhance, or otherwise alter promoter expression. Techniques for obtaining such derivatives are well-known in the art (see, for example, J. F. Sambrook, D. W. Russell, and N. Irwin (2000) Molecular Cloning: A Laboratory Manual, $3^{rd}$ edition Volumes 1, 2, and 3. Cold Spring Harbor Laboratory Press). For example, one of ordinary skill in the art may delimit the functional elements within the promoters disclosed herein and delete any non-essential elements. Functional elements may be modified or combined to increase the utility or expression of the sequences of the invention for any particular application. Those of skill in the art are familiar with the standard resource materials that describe specific conditions and procedures for the construction, manipulation, and isolation of macromolecules (e.g., DNA molecules, plasmids, etc.), as well as the generation of recombinant organisms and the screening and isolation of DNA molecules.

As used herein, the term "percent sequence identity" refers to the percentage of identical nucleotides between two segments of a window of optimally aligned DNA. Optimal alignment of sequences for aligning a comparison window are well-known to those skilled in the art and may be conducted by tools such as the local homology algorithm of Smith and Waterman (Waterman, M. S. Introduction to Computational Biology: Maps, sequences and genomes. Chapman & Hall. London (1995), the homology alignment algorithm of Needleman and Wunsch (J. Mol. Biol., 48:443-453 (1970), the search for similarity method of Pearson and Lipman (Proc. Natl. Acad. Sci., 85:2444 (1988), and preferably by computerized implementations of these algorithms such as GAP, BESTFIT, FASTA, and TFASTA available as part of the GCG (Registered Trade Mark), Wisconsin Package (Registered Trade Mark from Accelrys Inc., San Diego, Calif.). An "identity fraction" for aligned segments of a test sequence and a reference sequence is the number of identical components that are shared by the two aligned sequences divided by the total number of components in the reference sequence segment, i.e., the entire reference sequence or a smaller defined part of the reference sequence. Percent sequence identity is represented as the identity fraction times 100. The comparison of one or more DNA sequences may be to a full-length DNA sequence or a portion thereof, or to a longer DNA sequence.

A nucleic acid comprising a nucleotide sequence having at least about 95% sequence identity to SEQ ID NO: 7 can thus be a nucleic acid comprising a nucleotide sequence having at least about 95%, or at least about 98%, 99% or 100% sequence identity to SEQ ID NO: 7.

A "functional fragment" of a nucleic acid comprising root-preferential and stress-inducible promoter denotes a nucleic acid comprising a stretch of the nucleic acid sequences of SEQ ID NO: 7, or of the nucleic acid having at least 95% sequence identity to SEQ ID NO: 7 which is at least 400 bp and still exerts the desired function, i.e. which has root-preferential and stress inducible promoter activity. Assays for determining root-preferential promoter activity are provided herein. Preferably, the functional fragment of the root-preferential and stress-inducible promoter contains the conserved promoter motifs, such as, for example, conserved promoter motifs as described in DoOP (doop.abc.hu, databases of Orthologous Promoters, Barta E. et al. (2005) Nucleic Acids Research Vol. 33, D86-D90). A functional fragment may be a fragment of at least about 400 bp, at least about 500 bp, at least about 600 bp, at least about 700 bp, at least about 800 bp, at least about 900 bp from the transcription start site or at least about 600 bp, at least about 700 bp, at least about 800 bp, at least about 900 bp, at least about 1000 bp from the translation start site.

A nucleic acid comprising the nucleotide sequence of SEQ ID NO: 7 which further comprises insertion, deletion, substitution of at least 1 nucleotide up to 20 nucleotides, at least 1 nucleotide up to 15 nucleotides, at least 1 nucleotide up to 10 nucleotides, at least 1 nucleotide up to 5 nucleotides, at least 1 nucleotide up to 4 nucleotides, at least 1 nucleotide up to 3 nucleotides, or even at least 1 nucleotide up to 2 nucleotides may cover at least about 600 bp, at least about 700 bp, at least about 800 bp, at least about 900 bp from the transcription start site or at least about 800 bp, at least about 900 bp, at least about 1000 bp from the translation start site.

A number of putative response elements were identified on the promoter sequence disclosed herein. The search was limited to stress-responsive elements. Four ABA-responsive element-like (ABRE-like) motifs were identified at the nucleotide positions 186 to 193, 192 to 199, 223 to 230 and 235 to 242 in SEQ ID NO: 7.

Variants of the promoter described herein include those which comprise the identified ABRE-like motifs, but have otherwise been modified to delete nucleotide stretches within the sequence which are not needed for the promoter to be functional in root-preferential and stress-inducible manner. For example, any nucleotide stretch located between the motifs and/or between the transcriptional start and the first motif may be at least partially deleted to result in a shorter nucleotide sequence than the about 1 kb sequence of SEQ ID NO: 7.

Other nucleic acids comprising root-preferential, stress-inducible or stress-induced root-preferential promoter activity can be identified using methods known in the art. Such nucleotide sequence may be identified and isolated by hybridization under stringent conditions using as probes a nucleic acid comprising the nucleotide sequences of SEQ ID NO: 7 or part thereof. Other nucleic acids comprising root-preferential, stress-inducible or stress-induced root-preferential promoter activity may also be obtained by DNA amplification using oligonucleotides specific for the sequences according to the invention as primers, such as but not limited to oligonucleotides comprising or consisting of about 20 to about 50 consecutive nucleotides from any one of the nucleotide sequences of SEQ ID NO: 7 or its complement. Other nucleic acids comprising root-preferential, stress-inducible or stress-induced root-preferential promoter activity can be identified in silico using Basic Local Alignment Search Tool (BLAST) homology search with other nucleotide or amino acid sequences. Functionality of the identified nucleic acids comprising root-preferential, stress-inducible or stress-induced root-preferential promoter activity can be validated using the methods described herein. Other nucleic acids comprising root-preferential, stress-inducible or stress-induced root-preferential promoter activity may also be identified by identification of gene sequences orthologous to the gene sequences of the endogenous coding sequences of the genes controlled by the promoters of the invention, and isolating and testing the promoter sequences upstream of these orthologous homologous coding sequences.

The promoters according to the invention can further be used to create hybrid promoters, i.e. promoters containing (parts of) one or more of the promoters(s) of the current invention and (parts of) other promoter which can be newly identified or known in the art. Such hybrid promoters may have optimized tissue specificity or expression level.

As used herein, "plant-expressible promoter" means a region of DNA sequence that is essential for the initiation of transcription in a plant cell. This includes any promoter of plant origin, but also any promoter of non-plant origin which is capable of directing transcription in a plant cell, i.e. certain promoters of viral or bacterial origin such as the CaMV35S, the subterranean clover virus promoter No 4 or No 7 (WO9606932) or T-DNA gene promoters and the like.

In a further embodiment the plant expressible promoter is a constitutive promoter. In another embodiment the promoter is the Cauliflower Mosaic Virus CaMV35S promoter.

Other examples of constitutive promoters include the promoter from the actin gene (McElroy et al. (1990) Plant Cell 2: 163-171), the CaMV19S promoter (Nilsson et al. (1997) Physiol. Plant. 100: 456-462), the GOS2 promoter (de Pater et al. (1992) Plant. J. 2(6): 837-44), the promoter from ubiquitin gene (Christensen et al. (1992) Plant Mol. Biol. 18: 675-689), the promoter from rice cyclophilin gene (Buchholz et al. (1994) Plant. Mol. Biol. 25(5): 837-43), the promoter from the maize H3 histone gene (Lepetit et al. (1992) Mol. Gen. Genet. 231: 276-285) or the promoter from the actin 2 gene (An et al. (1996) Plant J. 10(1): 107-121).

Recombinant Genes

A further embodiment provides a recombinant gene comprising the nucleic acid having stress-induced root-preferential promoter activity described above operably linked to a heterologous nucleic acid sequence encoding an expression product of interest, and optionally a transcription termination and polyadenylation sequence, preferably a transcription termination and polyadenylation region functional in *Gossypium* plant cells. In a further embodiment, said expression product of interest an RNA capable of modulating the expression of a gene or is a protein.

The phrase "operably linked" refers to the functional spatial arrangement of two or more nucleic acid regions or nucleic acid sequences. For example, a promoter region may be positioned relative to a nucleic acid sequence such that transcription of a nucleic acid sequence is directed by the promoter region. Thus, a promoter region is "operably linked" to the nucleic acid sequence. "Functionally linked" is an equivalent term.

The term "expression product" refers to a product of transcription. Said expression product can be the transcribed RNA. It is understood that the RNA which is produced is a biologically active RNA. Said expression product can also be a peptide, a polypeptide, or a protein, when said biologically active RNA is an mRNA and said protein is produced by translation of said mRNA.

Alternatively, the heterologous nucleic acid, operably linked to the promoters of the invention, may also code for an RNA capable of modulating the expression of a gene. Said RNA capable of modulating the expression of a gene can be an RNA which reduces expression of a gene. Said RNA can reduce the expression of a gene for example through the mechanism of RNA-mediated gene silencing.

Said RNA capable of modulating the expression of a gene can be a silencing RNA downregulating expression of a target gene. As used herein, "silencing RNA" or "silencing RNA molecule" refers to any RNA molecule, which upon introduction into a plant cell, reduces the expression of a target gene. Such silencing RNA may e.g. be so-called "antisense RNA", whereby the RNA molecule comprises a sequence of at least 20 consecutive nucleotides having 95% sequence identity to the complement of the sequence of the target nucleic acid, preferably the coding sequence of the target gene. However, antisense RNA may also be directed to regulatory sequences of target genes, including the promoter sequences and transcription termination and polyadenylation signals. Silencing RNA further includes so-called "sense RNA" whereby the RNA molecule comprises a sequence of at least 20 consecutive nucleotides having 95% sequence identity to the sequence of the target nucleic acid. Other silencing RNA may be "unpolyadenylated RNA" comprising at least 20 consecutive nucleotides having 95% sequence identity to the complement of the sequence of the target nucleic acid, such as described in WO01/12824 or U.S. Pat. No. 6,423,885 (both documents herein incorporated by reference). Yet another type of silencing RNA is an RNA molecule as described in WO03/076619 (herein incorporated by reference) comprising at least 20 consecutive nucleotides having 95% sequence identity to the sequence of the target nucleic acid or the complement thereof, and further comprising a largely-double stranded region as described in WO03/076619 (including largely double stranded regions comprising a nuclear localization signal from a viroid of the Potato spindle tuber viroid-type or comprising CUG trinucleotide repeats). Silencing RNA may also be double stranded RNA comprising a sense and antisense strand as herein defined, wherein the sense and antisense strand are capable of base-pairing with each other to form a double stranded RNA region (preferably the said at least 20 consecutive nucleotides of the sense and antisense RNA are complementary to each other). The sense and antisense region may also be present within one RNA molecule such that a hairpin RNA (hpRNA) can be formed when the sense and antisense region form a double stranded RNA region. hpRNA is well-known within the art (see e.g WO99/53050, herein incorporated by reference). The hpRNA may be classified as long hpRNA, having long, sense and antisense regions which can be largely complementary, but need not be entirely complementary (typically larger than about 200 bp, ranging between 200-1000 bp). hpRNA can also be rather small ranging in size from about 30 to about 42 bp, but not much longer than 94 bp (see WO04/073390, herein incorporated by reference). Silencing RNA may also be artificial micro-RNA molecules as described e.g. in WO2005/052170, WO2005/047505 or US 2005/0144667, or ta-siRNAs as described in WO2006/074400 (all documents incorporated herein by reference). Said RNA capable of modulating the expression of a gene can also be an RNA ribozyme.

Said RNA capable of modulating the expression of a gene can modulate, preferably downregulate, the expression of other genes (i.e. target genes) comprised within the roots or even of genes present within a pathogen or pest that feeds upon the roots of the transgenic plant such as a virus, fungus, insect, nematode, bacteria. An example of pest control using gene silencing is described, for example, in WO2007/080127.

The nucleic acid sequence heterologous to the promoters according to the invention may generally be any nucleic acid sequence effecting increased, altered (e.g. in a different organ) or reduced level of transcription of a gene for which such expression modulation is desired. The nucleic acid sequence can for example encode a protein of interest. Exemplary genes for which an increased or reduced level of transcription may be desired in the roots are e.g. nucleic acids that can provide an agriculturally or industrially important feature in roots. Suitable heterologous nucleic acid sequences of interest include nucleic acids modulating expression of genes conferring resistance to root pests, like nematodes, and diseases, stress tolerance genes, genes encoding proteins involved in cell expansion and cell division genes involved in nutrient uptake, genes involved in metabolism or nutrient assimilation, genes encoding transport proteins, such as nitrate transporters including NRT transport proteins, ammonium transporters including AMT proteins, and the like.

Examplary genes for which an increased or reduced level of transcription may be desired upon stress are e.g. genes encoding protection factors of macromolecules (LEA proteins, chaperones), key enzymes for osmolyte biosynthesis (proline, sugars), detoxification enzymes (e.g. Super Oxide Dismutase), water channels or transporters, transcription factors (for example DREB2, AREB, MYC, bZIP, NAC) or genes involved in hormone signaling or biosynthesis (examples of relevant hormones are ABA, brassinosteroid, cytokinin, ethylene). Genes for nematode resistance are also of relevance (e.g., WO 1995/020669, WO 2001/051627, WO 2008/139334, WO 2008/095972, WO 2006/085966, WO 2003/033651, WO 1999/060141, WO 1998/012335, WO 1996/030517, WO 1993/018170, WO2008/095886, WO2008/095887, WO2008/095888, WO2008/095889, WO2008/095910, WO2008/095911, WO2008/095916, WO2008/095919, WO2008/095969, WO2008/095970, WO2008/095972, WO2008/110522, WO2008/139334, WO2008/152008, WO2010/077858, WO 2010/091230, WO 2010/102172, WO 2010/106163, WO2011/082217, WO2011/003783, WO 2011/014749, WO 2007/147029, WO 2014/003769, WO 2010/077858.

A "transcription termination and polyadenylation region" as used herein is a sequence that controls the cleavage of the nascent RNA, whereafter a poly(A) tail is added at the resulting RNA 3' end, functional in plant cells. Transcription termination and polyadenylation signals functional in plant cells include, but are not limited to, 3'nos, 3'35S, 3'his and 3'g7.

The term "protein" interchangeably used with the term "polypeptide" as used herein describes a group of molecules consisting of more than 30 amino acids, whereas the term "peptide" describes molecules consisting of up to 30 amino acids. Proteins and peptides may further form dimers, trimers and higher oligomers, i.e. consisting of more than one (poly)peptide molecule. Protein or peptide molecules forming such dimers, trimers etc. may be identical or non-identical. The corresponding higher order structures are, consequently, termed homo- or heterodimers, homo- or heterotrimers etc. The terms "protein" and "peptide" also refer to naturally modified proteins or peptides wherein the modification is effected e.g. by glycosylation, acetylation, phosphorylation and the like. Such modifications are well known in the art.

The term "heterologous" refers to the relationship between two or more nucleic acid or protein sequences that are derived from different sources. For example, a promoter is heterologous with respect to an operably linked DNA region, such as a coding sequence if such a combination is not normally found in nature. In addition, a particular sequence may be "heterologous" with respect to a cell or organism into which it is inserted (i.e. does not naturally occur in that particular cell or organism). For example, the recombinant gene disclosed herein is a heterologous nucleic acid.

The term "recombinant gene" refers to any artificial gene that contains: a) DNA sequences, including regulatory and coding sequences that are not found together in nature, or b) sequences encoding parts of proteins not naturally adjoined, or c) parts of promoters that are not naturally adjoined. Accordingly, a recombinant gene may comprise regulatory sequences and coding sequences that are derived from different sources, or comprise regulatory sequences, and coding sequences derived from the same source, but arranged in a manner different from that found in nature.

In another aspect, the invention provides a recombinant gene comprising (a) a plant expressible promoter selected from the group consisting of i. root-preferential promoter, ii. stress-inducible promoter and iii. Stress-induced root-preferential promoter, (b) a nucleic acid sequence encoding an Annexin protein (c) and optionally, a transcription termination and polyadenylation sequence, preferably a transcription termination and polyadenylation region functional in plants.

Any of the promoters and heterologous nucleic acid sequences described above may be provided in a recombinant vector. A recombinant vector typically comprises, in a 5' to 3' orientation: a promoter to direct the transcription of a nucleic acid sequence and a nucleic acid sequence. The recombinant vector may further comprise a 3' transcriptional terminator, a 3' polyadenylation signal, other untranslated nucleic acid sequences, transit and targeting nucleic acid sequences, selectable markers, enhancers, and operators, as desired. The wording "5' UTR" refers to the untranslated region of DNA upstream, or 5' of the coding region of a gene and "3' UTR" refers to the untranslated region of DNA downstream, or 3' of the coding region of a gene. Means for preparing recombinant vectors are well known in the art. Methods for making recombinant vectors particularly suited to plant transformation are described in U.S. Pat. Nos. 4,971,908, 4,940,835, 4,769,061 and 4,757,011. Typical vectors useful for expression of nucleic acids in higher plants are well known in the art and include vectors derived from the tumor-inducing (Ti) plasmid of *Agrobacterium tumefaciens*. One or more additional promoters may also be provided in the recombinant vector. These promoters may be operably linked, for example, without limitation, to any of the nucleic acid sequences described above. Alternatively, the promoters may be operably linked to other nucleic acid sequences, such as those encoding transit peptides, selectable marker proteins, or antisense sequences. These additional promoters may be selected on the basis of the cell type into which the vector will be inserted. Also, promoters which function in bacteria, yeast, and plants are all well taught in the art. The additional promoters may also be selected on the basis of their regulatory features. Examples of such features include enhancement of transcriptional activity, inducibility, tissue specificity, and developmental stage-specificity.

The recombinant vector may also contain one or more additional nucleic acid sequences. These additional nucleic acid sequences may generally be any sequences suitable for use in a recombinant vector. Such nucleic acid sequences include, without limitation, any of the nucleic acid sequences, and modified forms thereof, described above. The additional structural nucleic acid sequences may also be operably linked to any of the above described promoters. The one or more structural nucleic acid sequences may each be operably linked to separate promoters. Alternatively, the structural nucleic acid sequences may be operably linked to a single promoter (i.e. a single operon).

Annexins

Suitable for the invention are nucleic acids, encoding an Annexin protein, which comprise a nucleotide sequence having at least 40%, at least 50%, or at least 60%, or at least 70%, or at least 80%, or at least 85%, or at least 90%, or at least 95%, or at least 98% sequence identity to the herein described gene and are also referred to as variants. The term "variant" with respect to the nucleotide sequences SEQ ID NO: 12 and SEQ ID NO: 14 of the invention is intended to mean substantially similar sequences. Naturally occurring allelic variants such as these can be identified with the use of well-known molecular biology techniques, as, for example, with polymerase chain reaction (PCR) and hybridization techniques as herein outlined before. Variant nucleotide sequences also include synthetically derived nucleotide sequences, such as those generated, for example, by using site-directed mutagenesis of any one of SEQ ID NOs 12 or 14. Generally, nucleotide sequence variants of the invention will have at least 40%, 50%, 60%, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence. Derivatives of the DNA molecules disclosed herein may include, but are not limited to, deletions of sequence, single or multiple point mutations, alterations at a particular restriction enzyme site, addition of functional elements, or other means of molecular modification. Techniques for obtaining such derivatives are well-known in the art (see, for example, J. F. Sambrook, D. W. Russell, and N. Irwin (2000) Molecular Cloning: A Laboratory Manual, $3^{rd}$ edition Volumes 1, 2, and 3. Cold Spring Harbor Laboratory Press). Those of skill in the art are familiar with the standard resource materials that describe specific conditions and procedures for the construction, manipulation, and isolation of macromolecules (e.g., DNA molecules, plasmids, etc.), as well as the generation of recombinant organisms and the screening and isolation of DNA molecules.

The term "percent sequence identity" is used in this section as defined above.

A nucleic acid comprising a nucleotide sequence having at least 80% sequence identity to SEQ ID NO: 12 or SEQ ID NO: 14 can thus be a nucleic acid comprising a nucleotide sequence having at least 80%, or at least 85%, or at least 90%, or at least 95%, or at least 98%, or 100% sequence identity to SEQ ID NO: 12 or SEQ ID NO: 14 respectively.

In a preferred embodiment, the nucleic acid sequence, encoding an Annexin protein, comprises (a) a nucleotide sequence of SEQ ID NO: 12 or SEQ ID NO: 14; (b) a nucleotide sequence at least 80% identical to SEQ ID NO: 12 or SEQ ID NO: 14 (c) a nucleotide sequence of a nucleic acid capable of hybridizing under stringent conditions to the nucleotide sequence of SEQ ID NO: 12 or SEQ ID NO: 14, (d) a nucleotide sequence encoding the amino acid sequence of SEQ ID NO: 13 or SEQ ID NO: 15 (e) a nucleotide sequence encoding an amino acid sequence having 80% identity with SEQ ID NO: 13 or SEQ ID NO: 15, (f) a nucleotide sequence encoding a protein comprising four or more annexin-repeat domains.

SEQ ID NO: 12 represents the nucleotide sequence of the AnnBj1 gene, SEQ ID NO: 14 represents the nucleotide sequence of the GhAnn1 gene, SEQ ID NO: 13 represents the amino-acid sequence of the AnnBj1 protein and SEQ ID NO: 15 represents the amino-acid sequence of the GhAnn1 protein.

Annexins are defined by their highly conserved fold consisting of four or more repeats of a so-called annexin-repeat domain signature sequence. The annexin-repeat domains are known in the Pfam database as PF00191, in the Interpro database as IPR001464, and in the smart database as SM00335. Each repeat consists of a five-helix bundle. An endonexin fold can be identified at the start of each repeat. Calcium binding occurs in type II binding sites established in the endonexin fold regions of the first and fourth repeats. Further particular amino-acid are essential to the Annexin function: a tryptophan and a histidine in the first endonexin fold, a tryptophan at the end of the first annexin repeat domain and an isoleucine-arginine-isoleucine in the third endonexin fold (FIG. 2).

Though the invention preferably uses nucleic acid encoding the AnnBj1 from *Brassica juncea*, nucleic acids encoding other Annexins can be used. Examples of such proteins are: Q67EX8, E0ZQA2, D2JYA7, A0A078HJR9, X2JGY9, A0A078CEH0, D9J167, M4F009, D7KLX8, Q9SYT0, D2JYA6, R0GQT5, A0A078HYS1, M4F6Q4, A0A087G1V1, A0A078DR00, V4LGL7, A0A061FNB4, A0A067GQH6, V4T729, M4N630, O82090, S5GFP3, P93157, A9PA39, G3E7M9, M4MZ02, M5XRZ4, A9PH68, A0A059BS83, A0A067KYU4, M4FEQ6, K9JGF9, I3SZS2, A0A067LQJ4, B9RJJ1, O22341, S5G971, A0A059B7W7, A0A061DJJ7, A5BTZ8, G7KB73, A0A059B7M2, A0A059B7C5, Q9XEN8, A0A068TXQ7, K4BSR4, A0A059B8A3, A0A059B8Z0, Q42657, M5W098, Q9SB88, Q9ZRU7, P93158, A0A059BRT1, O24131, B9HFG8, M0ZNV9, B9H529, C6TFT8, I3RZY7, M4MX74, Q69DC2, L0AU94, L0ASQ7, V7B5V0, Q9M3H3, O81536, O24132, M4MX50, A0A068TYU6, R0G7S3, O81535, A0A022R8D3, A0A067ERS2, A0A078FJE4, M4E6E2, I3Y171, Q2XTE7, V7CRX1, A5B479, Q9XEE2, Q42922, A9X4R2, D7MT72, A0A072TF84, V4MJ15, A0A078H8V3, W9QYY2, M4ESW0, A0A087GE86, X2JPM6, Q9LX07, V4VZP8, B3TLY9, Q4ABP7, A0A078BZL8, A9X4R1, V4KSN9, B7U9R9.

Furthermore, it is clear that variants of Annexin proteins, wherein one or more amino acid residues have been deleted, substituted or inserted, can also be used to the same effect in the methods according to the invention, provided that the Annexin repeat domains are not affected by the deletion, substitution or insertion of amino-acid. These variant Annexin proteins may have about 95% sequence identity to any one of the herein mentioned Annexin proteins.

Examples of substitutions are the conservative substitutions, i.e. substitutions of one amino-acid by another having similar physiochemical properties. These substitutions are known not to affect the structure of a protein. Such substitutions are achieved by replacing one amino acid by another amino acid belonging to the same group as follows:

Group 1: Cysteine (C);

Group 2: Phenylalanine (F), Tryptophan (W) and Tyrosine (Y);

Group 3: Histidine (H), Lysing K) and Arginine (R);

Group 4: Aspartic acid (D), Glutamic acid (E), Asparagine (N) and Glutamine (Q);

Group 5: Isoleucine (I), Leucine (L), Methionine (M) and Valine (V);

Group 6: Alanine (A), Glycine (G), Proline (P), Serine (S) and Threonine (T).

Host Cells and Plants

Yet other embodiments provide a host cell, such as an *E. coli* cell, an *Agrobacterium* cell, a yeast cell, or a plant cell, comprising the isolated nucleic acid according to the invention, or the recombinant genes according to the invention.

Other nucleic acid sequences may also be introduced into the host cell along with the promoter and structural nucleic acid sequence, e.g. also in connection with the vector of the invention. These other sequences may include 3' transcriptional terminators, 3' polyadenylation signals, other untranslated nucleic acid sequences, transit or targeting sequences, selectable markers, enhancers, and operators. Preferred nucleic acid sequences of the present invention, including recombinant vectors, structural nucleic acid sequences, promoters, and other regulatory elements, are described above.

In further embodiments, a plant is provided comprising any of the recombinant genes according to the invention. A further embodiment provides plant parts and seeds obtainable from the plant according to the invention. These plant parts and seeds comprise the recombinant genes described above. In another embodiment, the plants, plant parts or seeds according to the invention are cotton, soybean or wheat plants, plant parts or seeds.

The plant cell or plant comprising any of the recombinant gene according to the invention can be a plant cell or a plant comprising a recombinant gene of which either the promoter, or the heterologous nucleic acid sequence operably linked to said promoter, are heterologous with respect to the plant cell. Such plant cells or plants may be transgenic plant in which the recombinant gene is introduced via transformation. Alternatively, the plant cell of plant may comprise the promoter according to the invention derived from the same species operably linked to a nucleic acid which is also derived from the same species, i.e. neither the promoter nor the operably linked nucleic acid is heterologous with respect to the plant cell, but the promoter is operably linked to a nucleic acid to which it is not linked in nature. A recombinant gene can be introduced in the plant or plant cell via transformation, such that both the promoter and the operably linked nucleotide are at a position in the genome in which they do not occur naturally. Alternatively, the promoter according to the invention can be integrated in a targeted manner in the genome of the plant or plant cell upstream of an endogenous nucleic acid encoding an expression product of interest, i.e. to modulate the expression pattern of an endogenous gene. The promoter that is integrated in a targeted manner upstream of an endogenous nucleic acid can be integrated in cells of a plant species from which it is originally derived, or in cells of a heterologous plant species. Alternatively, a heterologous nucleic acid can be integrated in a targeted manner in the genome of the plant or plant cell downstream of the promoter according to the invention, such that said heterologous nucleic acid is expressed root-preferentially and is stress-inducible. Said heterologous nucleic acid is a nucleic acid which is heterologous with respect to the promoter, i.e. the combination of the promoter with said heterologous nucleic acid is not normally found in nature. Said heterologous nucleic acid may be a nucleic acid which is heterologous to said plant species in which it is inserted, but it may also naturally occur in said plant species at a different location in the plant genome. Said promoter or said heterologous nucleic acid can be integrated in a targeted manner in the plant genome via targeted sequence insertion, using, for example, the methods as described in WO2005/049842.

"Plants" encompasses "monocotyledonous plants" and "dicotyledonous plants".

"Monocotyledonous plants", also known as "monocot plants" or "monocots" are well known in the art and are plants of which the seed typically has one cotyledon. Examples of monocotyledons plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

"Dicotyledonous plants", also known as "dicot plants" or "dicots" are well known in the art and are plants of which the seed typically has two cotyledons. Examples of families of dicotyledonous plants are Brassicaceae, Solanaceae, Fabaceae, Malvaceae.

"Malvaceae" as used herein refers to plants belonging to the family of Malvaceae plants, also called mallows family. Examples of Malvaceae are, but are not limited to, *Gossypium* species, such as *Gossypium hirsutum, Gossypium barbadense, Gossypium arboreum* and *Gossypium herbaceum* or progeny from crosses of such species with other species or crosses between such species.

"Cotton" or "cotton plant" as used herein can be any variety useful for growing cotton. The most commonly used cotton varieties are *Gossypium barbadense, G. hirsutum, G. arboreum* and *G. herbaceum*. Further varieties include *G. africanum* and *G. raimondii*. Also included are progeny from crosses of any of the above species with other species or crosses between such species.

The following is a non-limiting list of cotton genotypes which can be used for transformation: Coker 312, Coker310, Coker 5Acala SJ-5, GSC25110, Siokra 1-3, T25, GSA75, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala C1, Acala Royale, Acala Maxxa, Acala Prema, Acala B638, Acala B1810, Acala B2724, Acala B4894, Acala B5002, Acala 1517-88, Acala 1517-91, Acala 1517-95, non Acala "picker" Siokra, "stripper" variety FC2017, Coker 315, STONEVILLE 506, STONEVILLE 825, STONEVILLE 324, STONEVILLE 453, STONEVILLE 474, STONEVILLE KC 311, STONEVILLE LA 887, STONEVILLE 4145, STONEVILLE 4288, STONEVILLE 4498, STONEVILLE 4554, STONEVILLE 4747, STONEVILLE 4946, STONEVILLE 5032, STONEVILLE 5115, STONEVILLE 5289, STONEVILLE 5445, STONEVILLE 5458, STONEVILLE 6182, STONEVILLE 6448, Daytona, Cobalt, DP20, DP20B, DP NUCOTN 33B, DP NUCOTN 35B, DP41, DP50, DP51, DP61, DP90, DP77, DP161, DP340, DP357, DP358, DP360, DP744, DP0912, DP0920, DP0924, DP0935, DP0949, DP0920, DP1028, DP1034, DP1044, DP1050, DP1133, DP1137, DP1212, DP1219, DP1252, DP1311, DP1321, DP1359, DP1410, DP1441, DP1454, DP5409, DP5415, DP5461, DP5690, DP5816, MON/DP 09R303, MON/DP 09R549, MON/DP 09R550, MON/DP 09R555, MON/DP 09R573, MON/DP 09R605, MON/DP 09R615, MON/DP 09R619, MON/DP 09R621, MON/DP 09R623, MON/DP 09R627, MON/DP 09R643, MON/DP 09R796, MON/DP 09R999, MON/DP 10R013, MON/DP 10R020, MON/DP 10R030, MON/DP 10R051, MON/DP 10R052, MON/DP 11R112, MON/DP 11R124, MON/DP 11R130, MON/DP 11R136, MON/DP 11R154, MON/DP 11R158, MON/DP 11R159, MON/DP 12R224, MON/DP 12R242, MON/DP 12R244, MON/DP 12R249, MON/DP 12R251, 12R254, MON/DP 13R310, MON/DP 13R348, MON/DP 13R352, MON/DP 14R1455, MON/DP 14R1456, DP Suregrow, Suregrow 125, Suregrow 248, Suregrow 404, Suregrow 501, Suregrow 1001, DES119, McN235, HBX87, HBX191, HBX107, FC 3027, CHEMBRED A1, CHEMBRED A2, CHEMBRED A3, CHEMBRED A4, CHEMBRED B1, CHEMBRED B2, CHEMBRED B3, CHEMBRED C1, CHEMBRED C2, CHEMBRED C3, CHEMBRED C4, CHEMBRED CB407, PAYMASTER 145, HS26, HS46, Hyperformer 44, Hyperformer HS46, SICALA, PIMA S6 ORO BLANCO PIMA, PIMA S7, HA01, HA02, HA03, HA04, HA05, HA195, HA211, HA195, HA222, White PIMA, PHY72, PHY222, PHY333, PHY339, PHY367, PHY375, PHY417, PHY427, PHY495, PHY499, PHY565, PHY575, PHY725, PHY755, PHY800, PHY802, PHY804, PHY805, PHY811, PHY830, FM5013, FM5015, FM5017, FM989, FM832, FM966, FM958, FM989, FM958, FM832, FM991, FM819, FM800, FM960, FM966, FM981, FM1320, FM1740, FM1773, FM1830, FM1845, FM1880, FM1900, FM1944, FM2007, FM2011, FM2322, FM2324, FM2334, FM2484, FM2989, FM5035, FM5044, FM5045, FM5013, FM5015, FM5017, FM5024, FM8270, FM9058, FM9160, FM9170, FM9180, FM9250 and plants with genotypes derived thereof.

"Fabaceae" as used herein refers to the plant commonly known as the legume, pea, or bean family plants. Examples of Fabaceae are, but are not limited to, *Glycine max* (soybean), *Phaseolus* (beans), *Pisum sativum* (pea), *Cicer arietinum* (chickpeas), *Medicago sativa* (alfalfa), *Arachis hypogaea* (peanut), *Lathyrus odoratus* (sweet pea), *Ceratonia siliqua* (carob), and *Glycyrrhiza glabra* (liquorice).

"Plant parts" as used herein are parts of the plant, which can be cells, tissues or organs, such as seeds, severed parts such as roots, leaves, flowers, pollen, fibers etc.

The plants according to the invention may additionally contain an endogenous or a transgene, which confers herbicide resistance, such as the bar or pat gene, which confer resistance to glufosinate ammonium (Liberty®, Basta® or Ignite®) [EP 0 242 236 and EP 0 242 246 incorporated by reference]; or any modified EPSPS gene, such as the 2mEPSPS gene from maize [EP0 508 909 and EP 0 507 698 incorporated by reference], or glyphosate acetyltransferase, or glyphosate oxidoreductase, which confer resistance to glyphosate (RoundupReady®), or bromoxynitril nitrilase to confer bromoxynitril tolerance, or any modified AHAS gene, which confers tolerance to sulfonylureas, imidazolinones, sulfonylaminocarbonyltriazolinones, triazolopyrimidines or pyrimidyl(oxy/thio)benzoates, such as oilseed rape imidazolinone-tolerant mutants PM1 and PM2, currently marketed as Clearfield® canola. Further, the plants according to the invention may additionally contain an endogenous or a transgene which confers increased oil content or improved oil composition, such as a 12:0 ACP thioesteraseincrease to obtain high laureate, which confers pollination control, such as such as barnase under control of an anther-specific promoter to obtain male sterility, or barstar under control of an anther-specific promoter to confer restoration of male sterility, or such as the Ogura cytoplasmic male sterility and nuclear restorer of fertility.

The plants or seeds of the plants according to the invention may be further treated with a chemical compound, such as a chemical compound selected from the following lists: Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; cotton insecticides such as Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor; and cotton fungicides such as Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin, Clopyralid, Diclofop, Ethametsulfuron, Fluazifop, Metazachlor, Quinmerac, Quizalofop. Fungicides/PGRs: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Carboxin, Chlormequat-chloride, Coniothryrium minitans, Cyproconazole, Cyprodinil, Difenoconazole, Dimethomorph, Dimoxystrobin, Epoxiconazole, Famoxadone, Fluazinam, Fludioxonil, Fluopicolide, Fluopyram, Fluoxastrobin, Fluquinconazole, Flusilazole, Fluthianil, Flutriafol, Fluxapyroxad, Iprodione, Isopyrazam, Mefenoxam, Mepiquat-chloride, Metalaxyl, Metconazole, Metominostrobin, Paclobutrazole, Penflufen, Penthiopyrad, Picoxystrobin, Prochloraz, Prothioconazole, Pyraclostrobin, Sedaxane, Tebuconazole, Tetraconazole, Thiophanate-methyl, Thiram, Triadimenol, Trifloxystrobin, *Bacillus firmus, Bacillus firmus* strain 1-1582, *Bacillus subtilis, Bacillus subtilis* strain GB03, *Bacillus subtilis* strain QST 713, *Bacillus pumulis, Bacillus. pumulis* strain GB34. Insecticides: Acetamiprid, Aldicarb, Azadirachtin, Carbofuran, Chlorantraniliprole (Rynaxypyr), Clothianidin, Cyantraniliprole (Cyazypyr), (beta-)Cyfluthrin, gamma-Cyhalothrin, lambda-Cyhalothrin, Cypermethrin, Deltamethrin, Dimethoate, Dinetofuran, Ethiprole, Flonicamid, Flubendiamide, Fluensulfone, Fluopyram, Flupyradifurone, tau-Fluvalinate, Imicyafos, Imidacloprid, Metaflumizone, Methiocarb, Pymetrozine, Pyrifluquinazon, Spinetoram, Spinosad, Spirotetramate, Sulfoxaflor, Thiacloprid, Thiamethoxam, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluorethyl)sulfinyl]phenyl}-3-(trifluoromethyl)-1H-1,2,4-triazol-5-amine, (1E)-N-[(6-chloropyridin-3-yl)methyl]-N'-cyano-N-(2,2-difluoroethyl)ethanimidamide, *Bacillus firmus, Bacillus firmus* strain 1-1582, *Bacillus subtilis, Bacillus subtilis* strain GB03, *Bacillus subtilis* strain QST 713, Metarhizium anisopliae F52.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents, such as seed obtained by selfing or crossing, e.g. hybrid seed (obtained by crossing two inbred parental lines), hybrid plants and plant parts derived there from are encompassed herein, unless otherwise indicated.

In some embodiments, the plant cells of the invention as well as plant cells generated according to the methods of the invention, may be non-propagating cells.

The obtained plants according to the invention can be used in a conventional breeding scheme to produce more plants with the same characteristics or to introduce the same characteristic in other varieties of the same or related plant species, or in hybrid plants. The obtained plants can further be used for creating propagating material. Plants according to the invention can further be used to produce gametes, seeds (including crushed seeds and seed cakes), seed oil, fibers, yarn, embryos, either zygotic or somatic, progeny or hybrids of plants obtained by methods of the invention. Seeds obtained from the plants according to the invention are also encompassed by the invention.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

Methods and Uses

Yet other embodiments provide a method of producing a transgenic plant comprising the steps of (a) introducing or providing any of the recombinant genes according to the invention to a plant cell to create transgenic cells; and (b) regenerating transgenic plants from said transgenic cell.

"Introducing" in connection with the present application relates to the placing of genetic information in a plant cell or plant by artificial means. This can be effected by any method known in the art for introducing RNA or DNA into plant cells, protoplasts, calli, roots, tubers, seeds, stems, leaves, seedlings, embryos, pollen and microspores, other plant tissues, or whole plants. "Introducing" also comprises stably integrating into the plant's genome. Introducing the recombinant gene can be performed by transformation or by crossing with a plant obtained by transformation or its descendant (also referred to as "introgression").

The term "providing" may refer to introduction of an exogenous DNA molecule to a plant cell by transformation, optionally followed by regeneration of a plant from the transformed plant cell. The term may also refer to introduction of the recombinant DNA molecule by crossing of a transgenic plant comprising the recombinant DNA molecule with another plant and selecting progeny plants which have inherited the recombinant DNA molecule or transgene. Yet another alternative meaning of providing refers to introduction of the recombinant DNA molecule by techniques such as protoplast fusion, optionally followed by regeneration of a plant from the fused protoplasts.

The recombinant gene may be introduced into a plant cell by methods well-known in the art.

The term "transformation" herein refers to the introduction (or transfer) of nucleic acid into a recipient host such as a plant or any plant parts or tissues including plant cells, protoplasts, calli, roots, tubers, seeds, stems, leaves, fibers, seedlings, embryos and pollen. Plants containing the transformed nucleic acid sequence are referred to as "transgenic plants". Transformed, transgenic and recombinant refer to a host organism such as a plant into which a heterologous nucleic acid molecule (e.g. an expression cassette or a recombinant vector) has been introduced. The nucleic acid can be stably integrated into the genome of the plant.

As used herein, the phrase “transgenic plant” refers to a plant having a nucleic acid stably integrated into a genome of the plant, for example, the nuclear or plastid genomes. In other words, plants containing transformed nucleic acid sequence are referred to as “transgenic plants” and includes plants directly obtained from transformation and their descendants (Tx generations). Transgenic and recombinant refer to a host organism such as a plant into which a heterologous nucleic acid molecule (e.g. the promoter, the recombinant gene or the vector as described herein) has been introduced. The nucleic acid can be stably integrated into the genome of the plant.

It will be clear that the methods of transformation used are of minor relevance to the current invention. Transformation of plants is now a routine technique. Advantageously, any of several transformation methods may be used to introduce the nucleic acid/gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens et al. (1982) Nature 296: 72-74; Negrutiu et al. (1987) Plant. Mol. Biol. 8: 363-373); electroporation of protoplasts (Shillito et al. (1985) Bio/Technol. 3: 1099-1102); microinjection into plant material (Crossway et al. (1986) Mol. Gen. Genet. 202: 179-185); DNA or RNA-coated particle bombardment (Klein et al. (1987) Nature 327: 70) infection with (non-integrative) viruses and the like.

Methods to transform cotton plants are also well known in the art. *Agrobacterium*-mediated transformation of cotton has been described e.g. in U.S. Pat. No. 5,004,863 or in U.S. Pat. No. 6,483,013 and cotton transformation by particle bombardment is reported e.g. in WO 92/15675. Other suitable cotton transformation methods are disclosed e.g. in WO 00071733 and U.S. Pat. No. 5,159,135, which disclosures are incorporated by reference herein as if fully set forth. Methods to transform soybean are described e.g. in WO2014/150449.

Different transformation systems could be established for various cereals: the electroporation of tissue, the transformation of protoplasts and the DNA transfer by particle bombardment in regenerable tissue and cells (for an overview see Jane, Euphytica 85 (1995), 35-44). The transformation of wheat has been described several times in literature (for an overview see Maheshwari, Critical Reviews in Plant Science 14 (2) (1995), 149-178, Nehra et al., Plant J. 5 (1994), 285-297). Yuji Ishida et al. 2015, Methods in Molecular Biology, 1223: 189-198 describes a recent method to obtain transgenic wheat plants.

The recombinant DNA molecules according to the invention may be introduced into plants in a stable manner or in a transient manner using methods well known in the art. The recombinant genes may be introduced into plants, or may be generated inside the plant cell as described e.g. in EP 1339859.

Further provided are methods of effecting root-preferential, stress-inducible and stress-induced root-preferential expression of a nucleic acid comprising introducing a recombinant gene according to the invention that comprise a promoter having root-preferential, stress-inducible or stress-induced root-preferential promoter activity into the genome of a plant, or providing the plant according to the invention. Also provided is a method for altering biotic or abiotic stress tolerance, root architecture, nutrient use efficiency, nematode resistance or yield of a plant, comprising introducing the recombinant gene according to the invention into the genome of a plant, or providing the plant according to the invention. In another embodiment, said plant is a cotton, a soybean or a wheat plant.

Also provided is the use of the isolated nucleic acid according to the invention to regulate expression of an operably linked nucleic acid in a plant, and the use of the isolated nucleic acid according to the invention, or the recombinant gene comprising the nucleic acid having root-preferential, stress-inducible and stress-induced root-preferential promoter activity to alter biotic or abiotic stress tolerance, root architecture, nutrient use efficiency, or yield in a plant. In a further embodiment, said plant is a cotton, a soybean or a wheat plant. Also provided is the use of the isolated nucleic acid according to the invention to identify other nucleic acids comprising root-preferential, stress-inducible or stress-induced root-preferential promoter activity.

Yet another embodiment provides a method of producing food, feed, or an industrial product comprising (a) obtaining the plant or a part thereof, according to the invention; and (b) preparing the food, feed or industrial product from the plant or part thereof. In another embodiment, said food or feed is oil, meal, ground or crushed seeds, soybean flakes, grain, starch, flour or protein, or said industrial product is biofuel, fiber, industrial chemicals, a pharmaceutical or a nutraceutical. Such food, feed or industrial products contain the root-preferential, stress-inducible and stress-induced root-preferential promoter described herein.

In another embodiment, the invention provides a method to increase the yield, such as fiber yield and seed yield, of a plant, such as a cotton, a soybean plant and a wheat plant compared to a control plant under stress condition comprising (a) providing to cells of said plant a recombinant gene comprising (i) a heterologous plant expressible promoter, (ii) a nucleic acid sequence encoding an Annexin protein and (iii) optionally a transcription termination and polyadenylation sequence, preferably a transcription termination and polyadenylation region functional in plants, and (b) regenerating the plant.

In further embodiments, the stress is a drought stress, occurring during the plant reproductive stage, on field-grown plants.

The present invention provides a method to increase lint yield and a method to increase seed yield. In a further embodiment the increase yield compared to a control plant is at least 5%.

“Control plant” as used herein refers to a plant genetically resembling the tested plant but not carrying the recombinant gene, such as wild type plants or null segregant plants.

Furthermore, the disclosed method is expected to yield similar results in other plant species. Particularly, it is expected to increase yield in corn under drought stress under field conditions. It may also lead to a yield increase in *Brassica napus* under stress condition in the field.

According to the present invention, the method provided more consistently increased yield when said plant expressible promoter is a root-preferential, stress-inducible or stress-induced root-preferential promoter, preferentially the Pbtg-26GhD10 promoter, compared to when said plant expressible promoter is a constitutive promoter, preferentially the CaMV35S promoter.

The phrase “more consistently increase yield” as used in this application means that a larger proportion of the obtained plants display the increased yield when using the root-preferential, stress-inducible or stress-induced root-preferential promoter compared to the proportion of plants displaying an increased yield when using a constitutive promoter. For example the proportion may be increased by at least 10%, at least 20%, at least 30%, at least 40%, at least 50%, at least 60%, at least 70%, at least 80%, at least 90% or even 100%.

Furthermore, the disclosed method is expected to yield similar results in other plant species. Particularly, it is expected to more consistently increase yield in corn under drought stress under field conditions. It may also lead to a more consistent yield increase in *Brassica napus* under stress condition in the field.

The transformed plant cells and plants obtained by the methods described herein may be further used in breeding procedures well known in the art, such as crossing, selfing, and backcrossing. Breeding programs may involve crossing to generate an F1 (first filial) generation, followed by several generations of selfing (generating F2, F3, etc.). The breeding program may also involve backcrossing (BC) steps, whereby the offspring is backcrossed to one of the parental lines, termed the recurrent parent.

Accordingly, also disclosed herein is a method for producing plants comprising the recombinant gene disclosed herein comprising the step of crossing the plant disclosed herein with another plant or with itself and selecting for offspring comprising said recombinant gene.

The transformed plant cells and plants obtained by the methods disclosed herein may also be further used in subsequent transformation procedures, e.g. to introduce a further recombinant gene.

Stress and Yield Definitions

Yield as used herein can comprise yield of the plant or plant part which is harvested, such as lint, biomass, or seed, including seed oil content, seed weight, seed number. Increased yield can be increased yield per plant, and increased yield per surface unit of cultivated land, such as yield per hectare. Yield can be increased by modulating, for example, water uptake in the roots, or indirectly by increasing the tolerance to biotic and abiotic stress conditions.

"Stress" refers to non-optimal environmental conditions such as biotic stress and abiotic stress.

Abiotic stress tolerance as used herein can comprise resistance to environmental stress factors such as drought, flood, extreme (high or low) temperatures, soil salinity or heavy metals, hypoxia, anoxia, osmotic stress, oxidative stress, low nutrient levels such as nitrogen or phosphorus.

Biotic stress tolerance as used herein can comprise pest resistance, such as resistance or fungal, bacterial, bacterial or viral pathogens or nematodes or insects.

Drought as used in the present application relates to the shortage or absence of water available to a plant for a specified time. Such shortage or absence of water may last only a few days such as at least or up to 2, at least or up to 3, at least or up to 4, at least or up to 5, at least or up to 6, at least or up to 7, at least or up to 8, at least or up to 9, at least or up to 10, at least or up to 15 or at least or up to 20 days. It may as well be for a longer period such as at least or up to 3 weeks, at least or up to 4 weeks, at least or up to 5 weeks, at least or up to 6 weeks, at least or up to 2 months, at least or up to 3 months, at least or up to 4 months, at least or up to 5 months or at least or up to 6 months. In some areas of the world, drought may even last longer than 6 month, such as 7, 8, 9, 10, 11, 12, 15, 18 or 24 months.

Drought stress may be applied to the plant simply by depriving it of or reducing its water supply, either by placing them in a naturally drought exposed region or by reducing water supply in the field. For example, the water supply may be reduced by at least 10%, at least 20%, at least 30%, at least 40%, at least 50%, at least 60%, at least 70%, at least 80%, at least 90% or even 100% for a desired time falling within those described above in connection with drought stress.

General Definitions

"Isolated nucleic acid", used interchangeably with "isolated DNA" as used herein refers to a nucleic acid not occurring in its natural genomic context, irrespective of its length and sequence. Isolated DNA can, for example, refer to DNA which is physically separated from the genomic context, such as a fragment of genomic DNA. Isolated DNA can also be an artificially produced DNA, such as a chemically synthesized DNA, or such as DNA produced via amplification reactions, such as polymerase chain reaction (PCR) well-known in the art. Isolated DNA can further refer to DNA present in a context of DNA in which it does not occur naturally. For example, isolated DNA can refer to a piece of DNA present in a plasmid. Further, the isolated DNA can refer to a piece of DNA present in another chromosomal context than the context in which it occurs naturally, such as for example at another position in the genome than the natural position, in the genome of another species than the species in which it occurs naturally, or in an artificial chromosome.

Hybridization occurs when the two nucleic acid molecules anneal to one another under appropriate conditions. Nucleic acid hybridization is a technique well known to those of skill in the art of DNA manipulation. The hybridization property of a given pair of nucleic acids is an indication of their similarity or identity. Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence. "Stringent hybridization conditions" and "stringent hybridization wash conditions" in the context of nucleic acid hybridization experiments such as Southern and Northern hybridization are sequence dependent, and are different under different environmental parameters. An example of highly stringent wash conditions is 0.15 M NaCl at 72° C. for about 15 minutes. An example of stringent wash conditions is a 0.2×SSC wash at 65° C. for 15 minutes. Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The phrases "DNA", "DNA sequence," "nucleic acid sequence," "nucleic acid molecule" "nucleotide sequence" and "nucleic acid" refer to a physical structure comprising an orderly arrangement of nucleotides. The DNA sequence or nucleotide sequence may be contained within a larger nucleotide molecule, vector, or the like. In addition, the orderly arrangement of nucleic acids in these sequences may be depicted in the form of a sequence listing, figure, table, electronic medium, or the like.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A recombinant gene comprising a nucleic acid which is functionally or structurally defined, may comprise additional DNA regions etc. However, in context with the present disclosure, the term "comprising" also includes "consisting of".

The sequence listing contained in the file named "BCS15-2008WO_ST25.txt", which is 118 kilobytes (size as measured in Microsoft Windows®), contains 31 sequences SEQ ID NO: 1 through SEQ ID NO: 31 is filed herewith by electronic submission and is incorporated by reference herein.

In the description and examples, reference is made to the following sequences:

SEQUENCE LISTING

SEQ ID NO: 1 nucleotide sequence of the T-DNA Pbtg-26Bn::GUS.

SEQ ID NO: 2 nucleotide sequence of the KVA07-32 primer.

SEQ ID NO: 3 nucleotide sequence of the KVA07-34 primer.

SEQ ID NO: 4 nucleotide sequence of the A-genome variant of btg-26Gh.

SEQ ID NO: 5 nucleotide sequence of the D-genome variant of btg-26Gh.

SEQ ID NO: 6 nucleotide sequence of the ca. 1kb long promoter of the A-genome variant of Pbtg-26Gh.

SEQ ID NO: 7 nucleotide sequence of the ca. 1kb long promoter of the D-genome variant of Pbtg-26Gh.

SEQ ID NO: 8 nucleotide sequence of the T-DNA Pbtg-26GhA0.6::GUS.

SEQ ID NO: 9 nucleotide sequence of the T-DNA Pbtg-26GhA10::GUS.

SEQ ID NO: 10 nucleotide sequence of the T-DNA Pbtg-26GhD0.6::GUS.

SEQ ID NO: 11 nucleotide sequence of the T-DNA Pbtg-26GhD10::GUS.

SEQ ID NO: 12: nucleotide sequence of AnnBj1.

SEQ ID NO: 13: amino acid sequence of AnnBj1.

SEQ ID NO: 14: nucleotide sequence of GhAnn1.

SEQ ID NO: 15: amino acid sequence of GhAnn1.

SEQ ID NO: 16: nucleotide sequence of AtAnn1.

SEQ ID NO: 17: amino acid sequence of AtAnn1.

SEQ ID NO: 18: nucleotide sequence of the T-DNA P35S::AnnBj1.

SEQ ID NO: 19: nucleotide sequence of the T-DNA Pbtg-26GhD10::AnnBj1.

SEQ ID NO: 20: qRT-PCR forward primer AnnBj1.

SEQ ID NO: 21: qRT-PCR reverse primer AnnBj1.

SEQ ID NO: 22: qRT-PCR forward primer PP2A.

SEQ ID NO: 23: qRT-PCR reverse primer PP2A.

SEQ ID NO: 24: nucleotide sequence of Axmi196.

SEQ ID NO: 25: amino acid sequence of Axmi196.

SEQ ID NO: 26: nucleotide sequence of Axmi031.

SEQ ID NO: 27: amino acid sequence of Axmi031.

SEQ ID NO: 28: nucleotide sequence of Axmi277.

SEQ ID NO: 29: amino acid sequence of Axmi277.

SEQ ID NO: 30: nucleotide sequence of Axn-2.

SEQ ID NO: 31: amino acid sequence of Axn-2.

SEQ ID NO: 32: amino acid sequence of the characteristic motif of endonexin fold region.

SEQ ID NO: 33: amino acid sequence of the GXGTD motif.

EXAMPLES

Example 1—Generation of Expression Constructs with the Pbtg-26Bn Promoter of *Brassica napus* Operably Linked to the GUS Reporter Gene (Pbtg-26Bn::GUS)

The promoter sequence of the *Brassica napus* btg-26 promoter (EMBL accession number S77096, 5' to 3' position 4474 to 4148 of SEQ ID NO:1), the GUS gene (3-glucuronidase) with intron (5' to 3' position 4101 to 2101 of SEQ ID NO: 1) and a fragment of the 3' untranslated region (UTR) of the CaMV 35S gene (5' to 3' position 2031 to 1827 of SEQ ID NO: 1) were assembled in a vector which contains the bar selectable marker cassette (position 1720 to 56 of SEQ ID NO: 1) to result in the T-DNA Pbtg-26Bn::GUS (SEQ ID NO: 1).

Example 2—Generation of Transgenic Plants Comprising Pbtg-26Bn::GUS

In a next step the recombinant vector comprising the expression cassette of example 1, i.e. Pbtg-26Bn::GUS, was used to stably transform *Gossypium hirsutum* Coker 312 using the embryogenic callus transformation protocol.

Example 3—Expression Pattern of Pbtg-26Bn::GUS in *Gossypium hirsutum*

β-glucuronidase activity of plants transformed with btg-26Bn::GUS was monitored in planta with the chromogenic substrate X-Gluc (5-bromo-4-Chloro-3-indolyl-β-D-glucuronic acid) during corresponding activity assays (Jefferson R A et al (1987) EMBO J. 20; 6(13):3901-7). For determination of promoter activity plant tissue was dissected, embedded, stained and analyzed as described (e.g., Pien S. et al (2001) PNAS 98(20):11812-7). Thus, the activity of beta-glucuronidase in the transformed plants was witnessed by the presence of the blue color due to the enzymatic metabolism of the substrate X-Gluc.

After growing the progeny of independent TO plants under optimal growing conditions plants were examined for GUS expression. From these plants leaf samples from the first pair of leaves, root samples and stems were taken and tested for GUS reporter gene expression (e.g., Pien S. et al (2001) PNAS 98(20):11812-7).

Surprisingly, the *Brassica napus* promoter was unable to confer root-preferential expression in *Gossypium hirsutum* (see table 1 for result) although it was demonstrated in the prior art that this promoter retained its root preferential activity even in the more distant species barley and therefore suggested a high degree of conservation throughout dicotyledons and monocotyledons.

Example 4—Isolation of the *Gossypium hirsutum* a and D-Subgenome Specific Alleles Encoding the Orthologous Genes of Btg-26 from *Brassica napus*

The coding sequences of the btg-26 genes from *Brassica napus* (EMBL accession number S77096), rice (EMBL accession number AF32358) and *Arabidopsis thaliana* (At1g54100) were used to blast against a *Gossypium hirsutum* genomic sequence database. Based on the obtained result, a 656 bp probe was amplified using the primer KVA07-32 (SEQ ID NO:2) and KVA07-34 (SEQ ID NO:3) to screen a BAC library containing genomic DNA clones of *Gossypium hirsutum* FiberMax variety. The nucleotide sequence of genomic fragments for each of the allelic variants were identified and are represented in SEQ ID NO:4 (A genome) and SEQ ID NO:5 (D genome).

For the A-genome variant (SEQ ID NO:4), a TATA box could be identified at positions 1986 to 1999; a transcription initiation site at position 1219. The 5' untranslated leader extends from nucleotide 1219 to 1483; the translation initiation codon is located at positions 1484 to 1486.

For the D-genome variant (SEQ ID NO:5), a TATA box could be identified at positions 2789 to 2803; a transcription initiation site at position 2822. The 5' untranslated leader extends from nucleotide 2822 to 3089; the translation initiation codon is located at positions 3090 to 3092.

FIG. 1 shows an alignment of the nucleotide sequence of the first ca. 1kb of the A and D promoters. Strikingly the two promoter fragments share about 78% sequence identity while the first 600 bp are nearly identical, sharing about 94% sequence identity.

Example 5—Generation of Expression Constructs with the Pbtg-26Gh Promoters of *Gossypium hirsutum* Operably Linked to the GUS Reporter Gene (Pbtg-26GhA0.6::GUS, Pbtg-26GhA10::GUS, Pbtg-26GhD0.6::GUS, Pbtg-26GhD10::GUS)

The promoter short sequence (ca. 600 bp) of the *Gossypium hirsutum* btg-26 promoter from the A subgenome (Pbtg-26GhA0.6, 5' to 3' position 4650 to 4086 of SEQ ID NO:8), the GUS gene with intron (5' to 3' position 4082 to 2082 of SEQ ID NO: 8) and a fragment of the 3' untranslated region (UTR) of the CaMV 35S gene (5' to 3' position 2012 to 1808 of SEQ ID NO: 8) were assembled in a vector which contains the bar selectable marker cassette (position 1720 to 56 of SEQ ID NO: 8) to result in the T-DNA Pbtg-26GhA0.6::GUS (SEQ ID NO: 8).

The promoter long sequence (ca. 1 kb) of the *Gossypium hirsutum* btg-26 promoter from the A subgenome (Pbtg-26GhA10, 5' to 3' position 5094 to 4086 of SEQ ID NO:9), the GUS gene with intron (5' to 3' position 4082 to 2082 of SEQ ID NO: 9) and a fragment of the 3' untranslated region (UTR) of the CaMV 35S gene (5' to 3' position 2012 to 1808 of SEQ ID NO: 9) were assembled in a vector which contains the bar selectable marker cassette (position 1720 to 56 of SEQ ID NO: 9) to result in the T-DNA Pbtg-26GhA10::GUS (SEQ ID NO: 9).

The promoter short sequence (ca. 600 bp) of the *Gossypium hirsutum* btg-26 promoter from the D subgenome (Pbtg-26GhD0.6, 5' to 3' position 4654 to 4083 of SEQ ID NO:10), the GUS gene with intron (5' to 3' position 4082 to 2082 of SEQ ID NO: 10) and a fragment of the 3' untranslated region (UTR) of the CaMV 35S gene (5' to 3' position 2012 to 1808 of SEQ ID NO: 10) were assembled in a vector which contains the bar selectable marker cassette (position 1720 to 56 of SEQ ID NO: 10) to result in the T-DNA Pbtg-26GhD0.6::GUS (SEQ ID NO: 10).

The promoter long sequence (ca. 1 kb) of the *Gossypium hirsutum* btg-26 promoter from the D subgenome (Pbtg-26GhD10, 5' to 3' position 5104 to 4083 of SEQ ID NO:11), the GUS gene with intron (5' to 3' position 4082 to 2082 of SEQ ID NO: 11) and a fragment of the 3' untranslated region (UTR) of the CaMV 35S gene (5' to 3' position 2012 to 1808 of SEQ ID NO: 11) were assembled in a vector which contains the bar selectable marker cassette (position 1720 to 56 of SEQ ID NO: 11) to result in the T-DNA Pbtg-26GhD10::GUS (SEQ ID NO: 11).

Example 6—Generation of Transgenic Plants Comprising the Different Pbtg-26Gh::GUS Cassettes In a next step the recombinant vector comprising the expression cassettes of example 5, i.e. Pbtg-26GhA0.6::GUS, Pbtg-26GhA10::GUS, Pbtg-26GhD0.6::GUS and Pbtg-26GhD10::GUS, were used to stably transform *Gossypium hirsutum* coker 312 using the embryogenic callus transformation protocol.

The recombinant vector comprising the expression cassette Pbtg-26GhD10::GUS is used to stably transform wheat using the method described in Yuji Ishida et al. 2015, Methods in Molecular Biology, 1223: 189-198.

The recombinant vector comprising the expression cassette Pbtg-26GhD10::GUS is used to stably transform soybean using the method described in the patent application WO2014/150449.

Example 7—Expression Pattern of the Different Pbtg-26Gh::GUS in *Gossypium hirsutum*

β-glucuronidase activity of plants transformed with Pbtg-26GhA0.6::GUS, Pbtg-26GhA10::GUS, Pbtg-26GhD0.6::GUS and Pbtg-26GhD10::GUS was monitored as described in example 3.

Table 1 shows the average expression profile of all events produced per construct in the selected tissues (roots, leaves and stems). Intensity of the staining was quantified on a scale from 0 to 5, 0 corresponding to the absence of staining.

It was unexpectedly observed that only the long version of the pbtg-26D promoter lead to a preferential expression of GUS in the roots. Indeed the short and long promoter fragments from the A subgenome as well as the short promoter fragment from the D subgenome drive similar expression levels in all tissues tested, with the short D promoter and long A promoter driving a slightly lower expression in the roots.

TABLE 1

| Promoter | Nb of events tested | Expression level: Root tissues | Leaf tissues | Stem tissues |
|---|---|---|---|---|
| Pbtg-26GhA0.6 | 5 | 3.0 | 2.8 | 3.0 |
| Pbtg-26GhA10 | 7 | 2.7 | 3.7 | 3.3 |
| Pbtg-26GhD0.6 | 8 | 1.7 | 2.4 | 2.4 |
| Pbtg-26GhD10 | 16 | 4.6 | 1.3 | 2.2 |
| Pbtg-26Bn | 8 | 3.7 | 3.4 | 3.6 |

It can further be concluded from these results that the shorter promoter fragment of D does not influence the root-preferential activity of the longer promoter fragment (SEQID NO: 7) and may for example be replaced by the sequence of the short A promoter in the nucleotide sequence of SEQ ID NO: 7 without affecting its activity.

Example 8—Sequence Analysis of the Pbtg-26GhD10 Promoter

FIG. 1 shows the nucleotide sequence of the Pbtg-26 promoters from *Gossypium hirsutum* annotated with the predicted CIS elements relevant for stress-inducible expression as well as the position of the TATA box and the transcription initiation site.

Four ABA responsive-like motifs (ABRE-like) could be predicted from the btg-26 promoter of the D sub-genome but these motifs are not conserved in the promoter sequence from the A sub-genome. These motifs suggest that only the promoter sequence from the D sub-genome is capable to respond to stress.

Example 9—Stress Inducibility of the Cotton Endogenous BTG-26D Gene

*Gossypium hirsutum* plants from the Cocker variety were grown in a growth chamber and were watered until the 2-leaf developmental stage. Leaf samples were then collected in triplicates on the last day of watering (control samples) and after 7 days without watering (D7 samples).

RNA was extracted using the Sigma plant RNA extraction kit and analyzed by sequencing. Table 2 shows the expression values obtained for the BTG-26D endogenous gene in the different samples. BTG-26D is significantly induced by the drought stress and its expression level is ca. 1.9 times higher after 7 days of drought than in the control condition. As predicted the BTG26-D promoter therefore has stress-inducible activity as demonstrated with the application of drought stress. The functionality of the ABRE-like elements in the promoter is thus confirmed.

TABLE 2

| | Replicate 1 | Replicate 2 | Replicate 3 | Average | SD |
|---|---|---|---|---|---|
| control | 43.5 | 28.3 | 47.0 | 39.6 | 9.9 |
| D7 | 95.7 | 72 | 57 | 74.9 | 19.5 |

Example 10—Assessment of the Promoter Activity of the Pbtg-26GhD10 Promoter in Soybean and Wheat β-glucuronidase activity of soybean and wheat plants transformed with Pbtg-26GhD10::GUS is monitored as described in example 3.

Results indicate that the promoter Pbtg-26GhD10 has root-preferential promoter activity in soybean. They also indicate that the promoter has stress-inducible promoter activity in Soybean. Furthermore, the promoter has stress-induced root-preferential promoter activity in soybean.

Results indicate that the promoter Pbtg-26GhD10 has root-preferential promoter activity in wheat. They also indicate that the promoter has stress-inducible promoter activity in wheat. Furthermore, the promoter has stress-induced root-preferential promoter activity in wheat.

Example 11—Construction of a Recombinant Gene Encoding an Annexin for Root-Preferential and for Constitutive Expression in Cotton Cells A DNA molecule having the nucleic acid sequence according to SEQ ID NO: 12 was synthesized by Entelechon GmbH.

Using standard recombinant DNA techniques, the constitutive promoter region CaMV35S according to the sequence from nucleotide position 89 to 506 of SEQ ID NO: 18, the 5'UTR sequence including the leader sequence of the chlorophyll a/b binding protein gene of *Petunia* hybrid according to the sequence from nucleotide position 511 to 568 of SEQ ID NO: 18, the DNA fragment coding for AnnBj1 according to the sequence SEQ ID NO: 12 or to the sequence from nucleotide position 577 to 1530 of SEQ ID NO: 18, and the 3' untranslated sequence of the *Arabidopsis thaliana* histone H4 gene according to the sequence from nucleotide position 1542 to 2202 of SEQ ID NO: 18 were assembled in a vector which contains the 2mepsps selectable marker cassette (position 2252 to 6080 of SEQ ID NO: 18) to result in the T-DNA P35S::AnnBj1 (SEQ ID NO: 18).

Using standard recombinant DNA techniques, the root-preferential promoter region Pbtg-26GhD10 according to the sequence from nucleotide position 89 to 1107 of SEQ ID NO: 19, the DNA fragment coding for AnnBj1 according to the sequence SEQ ID NO: 12 or to the sequence from nucleotide position 1111 to 2064 of SEQ ID NO: 19, and the 3' untranslated sequence of the *Arabidopsis thaliana* histone H4 gene according to the sequence from nucleotide position 2076 to 2736 of SEQ ID NO: 19 were assembled in a vector which contains the 2mepsps selectable marker cassette (position 2786 to 6614 of SEQ ID NO: 19) to result in the T-DNA Pbtg-26GhD10::AnnBj1 (SEQ ID NO: 19).

Example 12—Generation of Transgenic Cotton Plants Expressing AnnBj1

The T-DNA vectors from the Example 11 were introduced into *Agrobacterium tumefaciens* strains containing a helper Ti-plasmid and used in cotton transformation essentially as described in WO00/71733. Homozygous plants and their null segregants were further analyzed as described in the following Examples.

Example 13—Seed and Lint Yield Assessment of Transgenic Cotton Plants Expressing AnnBj1 in Field Trial Field trials were performed in the United States on 12 events from the transformation with the T-DNA Pbtg-26GhD10::AnnBj1 and 15 events from the transformation with the T-DNA P35S::AnnBj1 using a split plot design with 3 blocks. The events were allocated to the whole-plot within a block and the zygosity (Homozygous and Null) were allocated to the sub-block within the whole-plot.

Deficient irrigation treatment was applied from squaring stage. Typical agronomic inputs for conventionally grown cotton for the area, following best local agronomic practices were applied.

The parameters scored were lint yield and seed cotton yield. The obtained data were analysed using linear mixed model and AsREML software (Gilmour et al. 1999). The fixed part of the model consists on the main effect of the event, main effect of the zygosity and their interaction. The random terms of the model were block, whole-plot and sub-block affects to adjust for field heterogeneity.

Under control condition, no seed yield nor lint yield was observed for the tested events. However, under drought stress, the expression of AnnBj1 lead to an increased seed and/or lint yield. The results for the drought condition are shown in Table 3.

Out of the 12 events tested for Pbtg-26GhD10::AnnBj1, 9 have an increased seed yield compared to their null segregant of at least 5%, meaning that the three quarters of the events produced display the positive effect of the transgene. In comparison, out of the 15 P35S::AnnBj1 events, only 8 have a yield increase of at least 5% compared to their null segregant, meaning that half of the events produced display the positive effect of the transgene. Expressing the AnnBj1 gene under control of the Pbtg-26GhD10 promoter as opposed to the constitutive promoter thus results in obtaining 50% more events with an at least 5% seed yield increase compare to their nulls.

Regarding the lint yield, 8 out of the 12 events produced with the transformation with the T-DNA Pbtg-26GhD10::AnnBj1 have an increased yield of at least 5% compared to their nulls, i.e. three quarter of the events display the positive effect of the transgene. In contrast, only 7 of the 15 events tested from the transformation with the T-DNA 35S::AnnBj1 have an increased yield of at least 5% compared to their nulls, i.e. half of the events display the positive effect of the transgene. Expressing the AnnBj1 gene under control of the Pbtg-26GhD10 promoter as opposed to the constitutive promoter thus results in obtaining 50% more events with an at least 5% seed yield increase compare to their nulls.

In conclusion, constitutive expression of AnnBj1 in cotton results in both a seed yield and a lint yield increase of at least 5% compared to the respective null segregants. Stress-induced root-preferential expression of AnnBj1 in cotton results in both a seed yield and a lint yield increase of at least 5% compared to the respective null segregants. Furthermore, when using the root-preferential promoter Pbtg-26GhD10 in cotton, the effect of the AnnBj1 overexpression is more penetrant with more events displaying the improved yield compared to when using the constitutive promoter 35S under drought stress conditions in the field.

TABLE 3

% yield increase of homozygous over their respective null segregant - drought stress condition.

| T-DNA | Independent Events | % seed yield increase | % lint yield increase |
|---|---|---|---|
| Pbtg-26GhD10::AnnBj1 | 1 | −5.69 | −5.09 |
| | 2 | 13.96 | 15.63 |
| | 3 | −15.75 | −15.67 |
| | 4 | 5.43 | 5.72 |
| | 5 | 7.68 | 7.87 |
| | 6 | 20.35 | 23.83 |
| | 7 | 20.24 | 25.84 |
| | 8 | 12.79 | 11.97 |
| | 9 | 8.52 | 9.87 |
| | 10 | 18.17 | −0.65 |
| | 11 | 13.51 | 15.52 |
| | 12 | −5.25 | −3.92 |
| P35S::AnnBj1 | 1 | −4.18 | −4.43 |
| | 2 | 18.59 | 20.41 |
| | 3 | −74.25 | −75.13 |
| | 4 | 13.98 | 15.82 |
| | 5 | −1.65 | −1.20 |
| | 6 | 12.72 | 12.72 |
| | 7 | 28.78 | 28.25 |
| | 8 | 5.74 | 6.26 |
| | 9 | 4.02 | 4.70 |
| | 10 | 9.33 | 9.56 |
| | 11 | 16.98 | 19.43 |
| | 12 | 6.20 | 4.74 |
| | 13 | −3.48 | −1.52 |
| | 14 | 1.16 | 4.69 |
| | 15 | 0.16 | 0.07 |

Example 14—Seed and Lint Yield Assessment of Selected Transgenic Cotton Plants from Example 13 in Field Trial Field trials were performed again on 6 events from the transformation with the T-DNA Pbtg-26GhD10::AnnBj1 and 4 events from the transformation with the T-DNA P35S::AnnBj1. Events were selected based on their performance in the previous field trial. The field trial was designed, run and the results analyzed as described in Example 13.

Under control condition, no significant yield penalty was observed for the tested events. However, under drought stress, the expression of AnnBj1 lead to an increased lint yield compared to the wild type Coker plants. The results for the drought condition are shown in Table 4.

TABLE 4

% lint yield increase of homozygous over the wild type Coker - drought stress condition. The result of the first year field trial are added as reference.

| T-DNA | Independent Events | % lint yield increase to wild type, year 1 | % lint yield increase to wild type, year 2 |
|---|---|---|---|
| Pbtg-26GhD10::AnnBj1 | 2 | 111% | 114% |
| | 4 | 103% | 113% |
| | 6 | 116% | 121% |
| | 8 | 121% | 123% |
| | 9 | 110% | 118% |
| | 11 | 116% | 118% |
| P35S::AnnBj1 | 2 | 111% | 115% |
| | 9 | 111% | 116% |
| | 11 | 118% | 118% |
| | 14 | 113% | 115% |

Example 15—Stress-Induced Root-Preferential Promoter Activity of the Pbtg-26GhD10 Promoter in Cotton To further confirm the expression pattern conferred by the Pbtg-26GhD10 promoter, cotton seeds from 8 events containing the Pbtg-26GhD10::AnnBj1 transgene and wild type cotton seeds were surface sterilized, sown and grown in vitro either on control media or media containing 250 mM mannitol (i.e. stress media). Mannitol is well known in the art to mimic drought stress. Root and leaf tissues were collected at respectively 16 and 27 days after sowing from the plants grown on control media and stress media.

RNA from the sampled root and leaf tissues were extracted using the Spectrum plant total RNA kit from Sigma with protocol A. The gene PP2A was used as a reference gene. Q-RT PCR were performed and analysed using the method described in the manual of Applied Biosystems with the primers SEQ ID NO: 20 and SEQ ID NO: 21 for the AnnBj1 transcript and SEQ ID NO: 22 and SEQ ID NO: 23 for the PP2A transcript. Table 5 shows the obtained results.

TABLE 5

| | | Control media | | Stress media | | Fold change |
|---|---|---|---|---|---|---|
| | Event number | 2-[deltaCt] value | stdev | 2-[deltaCt] value | stdev | stress over control media |
| Leaf | 2 | 0.91 | 0.31 | 0.29 | 0.03 | 0.32 |
| | 4 | 2.17 | 0.43 | 0.60 | 0.13 | 0.28 |
| | 6 | 0.75 | 0.20 | 0.25 | 0.06 | 0.33 |
| | 8 | 1.66 | 0.67 | 1.01 | 0.59 | 0.61 |
| | 9 | 2.32 | 0.64 | 1.38 | 0.50 | 0.60 |
| | 11 | 1.10 | 0.92 | 0.49 | 0.03 | 0.45 |
| root | 2 | 0.11 | 0.03 | 0.82 | 0.55 | 7.68 |
| | 4 | 0.22 | 0.08 | 1.09 | 0.29 | 4.89 |
| | 6 | 0.06 | 0.02 | 0.85 | 0.08 | 13.72 |
| | 8 | 0.10 | 0.01 | 4.35 | 1.73 | 45.08 |

TABLE 5-continued

| | Control media | | Stress media | | Fold change |
|---|---|---|---|---|---|
| Event number | 2-[deltaCt] value | stdev | 2-[deltaCt] value | stdev | stress over control media |
| 9 | 1.62 | 0.64 | 8.05 | 0.56 | 4.97 |
| 11 | 0.08 | 0.01 | 2.11 | 0.87 | 25.83 |

Although the expression level in the leaf was not increased by the stress treatment applied, the expression in the root is increased at least 4 fold in the stress condition compared to control condition. The Pbtg-26GhD10 promoter therefore has, under high stress, a stress-induced root-preferential promoter activity.

A similar experiment was performed with a lower concentration of mannitol (200 mM instead of 250 mM) on the same events. The events carrying two copies of the Pbtg-26GhD10::AnnBj1 transgene also confirmed the stress-induced root-preferential promoter activity of the Pbtg-26GhD10 promoter under milder stress condition.

Example 16—Construction of a Recombinant Gene Encoding Nematode Resistance Genes for Stress-Induced Root-Preferential Expression in Soybean Cells Using standard recombinant DNA techniques, the stress-induced root-preferential promoter region Pbtg-26GhD10 as described above, the DNA fragment coding for Axmi196 according to the sequence SEQ ID NO: 24 are assembled in a vector which contains a selectable marker cassette to result in the T-DNA Pbtg-26GhD10::Axmi196.

The stress-induced root-preferential promoter region Pbtg-26GhD10 as described above, the DNA fragment coding for Axmi031 according to the sequence SEQ ID NO: 26 are assembled in a vector which contains a selectable marker cassette to result in the T-DNA Pbtg-26GhD10::Axmi031.

The stress-induced root-preferential promoter region Pbtg-26GhD10 as described above, the DNA fragment coding for Axmi277 according to the sequence SEQ ID NO: 28 are assembled in a vector which contains a selectable marker cassette to result in the T-DNA Pbtg-26GhD10::Axmi277.

The stress-induced root-preferential promoter region Pbtg-26GhD10 as described above, the DNA fragment coding for Axn-2 according to the sequence SEQ ID NO: 30 are assembled in a vector which contains a selectable marker cassette to result in the T-DNA Pbtg-26GhD10::Axn-2.

Example 17—Generation of Transgenic Soybean Plants Expressing Nematode Resistance Genes The T-DNA vectors from the Example 16 are introduced into *Agrobacterium tumefaciens* strains containing a helper Ti-plasmid and used in soybean transformation essentially as described in the patent application WO2014/150449. Homozygous plants and their null segregants are further analyzed as described in the following Examples.

Example 18—Assessment of the Nematode Resistance of Transgenic Soybean Plants Expressing Axmi196, Axmi031, Axmi277 or Axn-2 Under Control of the Pbtg-26GhD10 Promoter The nematode resistance of the transgenic plants was assessed according to the method described in WO 2011/014749, WO 2007/147029, WO 2014/003769, WO 2010/077858.

In conclusion, the promoter Pbtg-26GhD10 can be used in soybean to confer biotic stress tolerance, like nematode resistance.

Preferred embodiments are summarized in the following paragraphs:

1. An isolated nucleic acid having root-preferential, stress-inducible or stress-induced root-preferential promoter activity selected from the group consisting of:
   a. a nucleic acid comprising a nucleotide sequence of SEQ ID NO: 7 or a functional fragment thereof comprising the nucleotide sequence of SEQ ID NO: 7 from nucleotide position 351 to nucleotide position 755;
   b. a nucleic acid comprising a nucleotide sequence having at least about 95% sequence identity to SEQ ID NO: 7, or a functional fragment thereof; and
   c. the nucleic acid of a functional promoter capable of hybridizing under stringent conditions to the nucleotide sequence of SEQ ID NO: 7, or a functional fragment thereof wherein said functional fragment comprises at least about 400 consecutive nucleotides upstream of the transcription start of SEQ ID NO: 7.
2. A recombinant gene comprising the nucleic acid according to paragraph 1 operably linked to a heterologous nucleic acid sequence encoding an expression product of interest, and optionally a transcription termination and polyadenylation sequence, preferably a transcription termination and polyadenylation region functional in plants.
3. The recombinant gene according to paragraph 2, wherein the expression product of interest is an RNA molecule capable of modulating the expression of a gene or is a protein.
4. A host cell comprising the isolated nucleic acid according to paragraph 1, or the recombinant gene according to paragraph 2 or 3.
5. The host cell of paragraph 4 which is an *E. coli* cell, an *Agrobacterium* cell, yeast cell, or a plant cell.
6. A plant comprising the recombinant gene of paragraph 2 or 3, preferably stably integrated in the genome of said plant.
7. Plant parts and seeds obtainable from the plant according to paragraph 6 which comprise the recombinant gene according to paragraph 2 or paragraph 3.
8. The plant or plant cell or plant part or seed according to any one of paragraphs 5 to 7, which is a cotton plant, or a cotton plant cell or cotton plant or cotton seed.
9. The plant or plant cell or plant part or seed according to any one of paragraphs 5 to 7, which is a soybean plant, or a soybean plant cell or soybean plant part or soybean seed.
10. The plant or plant cell or plant part or seed according to any one of paragraphs 5 to 7, which is a wheat plant, or a wheat plant cell or wheat plant part or wheat seed.
11. Method of producing a transgenic plant comprising the steps of:
    a. introducing or providing the recombinant gene according to paragraph 2 or 3 to a plant cell to create transgenic cells; and
    b. regenerating transgenic plants from said transgenic cell.
12. Method of effecting root-preferential expression of a nucleic acid comprising introducing the recombinant gene according to paragraph 2 or 3 into the genome of a plant, or providing the plant according to paragraph 6.
13. Method of effecting stress-inducible expression of a nucleic acid comprising introducing the recombinant gene according to paragraph 2 or 3 into the genome of a plant, or providing the plant according to paragraph 6.

14. Method of effecting stress-induced expression of a nucleic acid preferentially in the roots comprising introducing the recombinant gene according to paragraph 2 or 3 into the genome of a plant, or providing the plant according to paragraph 6.
15. Method for altering biotic or abiotic stress tolerance, root architecture, nutrient use efficiency, or yield of a plant, said method comprising introducing the recombinant gene according to paragraph 2 or 3 into the genome of a plant, or providing the plant according to paragraph 6.
16. Use of the isolated nucleic acid according to paragraph 1 to regulate expression of an operably linked nucleic acid in a plant.
17. Use of the isolated nucleic acid according to paragraph 1, or the recombinant gene according to paragraph 2 or 3 to alter biotic or abiotic stress tolerance, root architecture, nutrient use efficiency, or yield in a plant.
18. Use of the isolated nucleic acid according to paragraph 1 to identify other nucleic acids comprising root-preferential promoter activity.
19. Use of the isolated nucleic acid according to paragraph 1 to identify other nucleic acids comprising stress-inducible promoter activity.
20. Use of the isolated nucleic acid according to paragraph 1 to identify other nucleic acids comprising stress-induced root-preferential promoter activity.
21. The method according to any one of paragraphs 11 to 15, or the use according to paragraph 17 to 19, wherein said plant is a cotton plant.
22. The method according to any one of paragraphs 11 to 15, or the use according to paragraph 17 to 19, wherein said plant is a soybean plant.
23. The method according to any one of paragraphs 11 to 15, or the use according to paragraph 17 to 19, wherein said plant is a wheat plant.
24. A method of producing food, feed, or an industrial product comprising
  a) obtaining the plant or a part thereof, of any one of paragraphs 6 to 10; and
  b) preparing the food, feed or industrial product from the plant or part thereof.
25. The method of paragraph 24 wherein
  a) the food or feed is oil, meal, grain, starch, flour or protein; or
  b) the industrial product is biofuel, fiber, industrial chemicals, a pharmaceutical or a nutraceutical.
26. A recombinant gene comprising:
  (a) a plant expressible promoter selected from
    i. root-preferential promoter;
    ii. stress-inducible promoter; or
    iii. stress-induced root-preferential promoter;
  (b) a nucleic acid sequence encoding an Annexin protein;
  (c) and optionally, a transcription termination and polyadenylation sequence, preferably a transcription termination and polyadenylation region functional in plants;
27. The recombinant gene of paragraph 26, wherein said plant expressible promoter is the Pbtg-26GhD10 promoter.
28. The recombinant gene of paragraph 26 or 27, wherein said nucleic acid encoding an Annexin protein comprises:
  a. a nucleotide sequence of SEQ ID NO: 12 or SEQ ID NO: 14;
  b. a nucleotide sequence at least 80% identical to SEQ ID NO: 12 or SEQ ID NO: 14;
  c. a nucleotide sequence of a nucleic acid capable of hybridizing under stringent conditions to the nucleotide sequence of SEQ ID NO: 12 or SEQ ID NO: 14;
  d. a nucleotide sequence encoding the amino acid sequence of SEQ ID NO: 13 or SEQ ID NO: 15;
  e. a nucleotide sequence encoding an amino acid sequence having 80% identity with SEQ ID NO: 13 or SEQ ID NO: 15;
  f. a nucleotide sequence encoding a protein comprising four or more annexin-repeated domains.
29. A method to increase the yield of a plant under stress condition comprising:
  a. providing to cells of said plant a recombinant gene comprising:
    i. a heterologous plant expressible promoter;
    ii. a nucleic acid sequence encoding an Annexin protein;
    iii. and optionally, a transcription termination and polyadenylation sequence, preferably a transcription termination and polyadenylation region functional in plants;
  b. regenerating said plant;

wherein the increase in yield is compared to the yield in a control plant.

30. The method of paragraph 29, wherein said plant expressible promoter is selected from the group consisting of:
  a. a root-preferential promoter;
  b. a stress-inducible promoter; and
  c. a stress-induced root-preferential promoter.
31. The method of paragraph 29 or 30, wherein said plant expressible promoter is the Pbtg-26GhD10 promoter.
32. The method of paragraph 29, wherein said plant expressible promoter is a constitutive promoter.
33. The method of paragraph 29 or 32, wherein said plant expressible promoter is the CaMV35S promoter.
34. The method of any one of paragraphs 29 to 33, wherein said nucleic acid encoding an Annexin protein comprises:
  a. a nucleotide sequence of SEQ ID NO: 12 or SEQ ID NO: 14;
  b. a nucleotide sequence at least 80% identical to SEQ ID NO: 12 or SEQ ID NO: 14;
  c. a nucleotide sequence of a nucleic acid capable of hybridizing under stringent conditions to the nucleotide sequence of SEQ ID NO: 12 or SEQ ID NO 14;
  d. a nucleotide sequence encoding the amino acid sequence of SEQ ID NO: 13 or SEQ ID NO: 15;
  e. a nucleotide sequence encoding an amino acid sequence having 80% identity with SEQ ID NO: 13 or SEQ ID NO: 15;
  f. a nucleotide sequence encoding a protein comprising four or more annexin-repeated domains.
35. The method of any one of paragraphs 29 to 34, wherein said plant is cotton.
36. The method of any one of paragraphs 29 to 34, wherein said plant is soybean.
37. The method of any one of paragraphs 29 to 34, wherein said plant is wheat.
38. The method of any one of paragraphs 29 to 37, wherein said stress condition is drought stress.
39. The method of any one of paragraphs 29 to 37, wherein said stress condition is occurring during the plant reproductive stage.
40. The method of any one of paragraphs 29 to 37, wherein said stress condition is occurring on field-grown plants.
41. The method of any one of paragraphs 29 to 35, wherein said plant is cotton and said yield is lint yield.
42. The method of any one of paragraphs 29 to 37, wherein said yield is seed yield.
43. The method of any one of paragraphs 29 to 42, wherein said yield is increased by at least 5%.

44. The method of paragraph 43, wherein the yield increased is more consistently obtained with the method of paragraphs 30 or 31 compared to the method of paragraphs 32 or 33.
45. A plant cell comprising a recombinant gene as defined in any one of paragraphs 26 to 28.
46. A plant consisting essentially of the plant cells of paragraph 45.
47. Plant parts or seeds obtainable from the plant according to paragraph 46.
48. The plant, plant cell, plant part or seed according to any one of paragraphs 45 to 47, which is a cotton plant, cotton plant cell, cotton plant part or cotton seed.
49. The plant, plant cell, plant part or seed according to any one of paragraphs 45 to 47, which is a soybean plant, soybean plant cell, soybean plant part or soybean seed.
50. The plant, plant cell, plant part or seed according to any one of paragraphs 45 to 47, which is a wheat plant, wheat plant cell, wheat plant part or wheat seed.

The invention claimed is:

1. A recombinant gene comprising a nucleic acid having root-preferential, stress-inducible or stress-induced root-preferential promoter activity comprising:

a. a nucleic acid comprising the nucleotide sequence of SEQ ID NO: 7 or b. a nucleic acid comprising a nucleotide sequence having at least 95% sequence identity to SEQ ID NO: 7; and further comprising a heterologous sequence.

2. The recombinant gene according to claim 1, wherein said heterologous nucleic acid sequence encodes an expression product of interest, and optionally a transcription termination and polyadenylation sequence.

3. The recombinant gene according to claim 2, wherein the expression product of interest is an RNA molecule capable of modulating the expression of a gene or is a protein.

4. A plant cell comprising the recombinant gene according to claim 1.

5. A plant comprising the recombinant gene of claim 2.

6. Plant parts and seeds comprising the recombinant gene according to claim 2.

7. A method of producing a transgenic plant comprising: regenerating transgenic plants from transgenic cells comprising the recombinant gene according to claim 2.

8. A method of effecting root-preferential expression of a nucleic acid comprising introducing the recombinant gene according to claim 2 into the genome of a plant.

9. A method of effecting stress-inducible expression of a nucleic acid comprising introducing the recombinant gene according to claim 2 into the genome of a plant.

10. A method of effecting stress-induced expression of a nucleic acid preferentially in the roots comprising introducing the recombinant gene according to claim 2 into the genome of a plant.

11. A method for altering biotic or abiotic stress tolerance, root architecture, nutrient use efficiency, or yield of a plant, said method comprising introducing the recombinant gene according to claim 2 into the genome of a plant.

12. The method according to claim 7 wherein said plant is a cotton, soybean or wheat plant.

13. The recombinant gene of claim 2, wherein the transcription termination and polyadenylation sequence is functional in plants.

14. A method of effecting root-preferential expression of a nucleic acid comprising providing the plant according to claim 5.

15. A method of effecting stress-inducible expression of a nucleic acid comprising providing the plant according to claim 5.

16. A method of effecting stress-inducible expression of a nucleic acid preferentially in the roots comprising providing the plant according to claim 5.

17. A method for altering biotic or abiotic stress tolerance, root architecture, nutrient use efficiency, or yield of a plant, said method comprising providing the plant according to claim 5.

18. The method according to claim 8, wherein said plant is a cotton, soybean or wheat plant.

19. The method according to claim 9, wherein said plant is a cotton, soybean or wheat plant.

20. The method according to claim 10, wherein said plant is a cotton, soybean or wheat plant.

21. The recombinant gene of claim 1, comprising a nucleic acid comprising a nucleotide sequence having at least 98% sequence identity to SEQ ID NO: 7.

22. The recombinant gene of claim 1, comprising a nucleic acid comprising a nucleotide sequence having at least 99% sequence identity to SEQ ID NO: 7.

23. The recombinant gene of claim 1 comprising the nucleotide sequence of SEQ ID NO: 7.

* * * * *